(12) United States Patent
Cosgrove

(10) Patent No.: US 6,492,325 B1
(45) Date of Patent: Dec. 10, 2002

(54) USE OF α1β1 INTEGRIN RECEPTOR INHIBITORS AND TGF-β1 INHIBITORS IN THE TREATMENT OF KIDNEY DISEASE

(75) Inventor: Dominic Cosgrove, Omaha, NE (US)

(73) Assignee: Boys Town National Research Hospital, Omaha, NE (US)

( * ) Notice: Subject to any disclaimer, the term of this patent is extended or adjusted under 35 U.S.C. 154(b) by 0 days.

(21) Appl. No.: 09/292,534

(22) Filed: Apr. 15, 1999

Related U.S. Application Data

(63) Continuation-in-part of application No. 09/150,485, filed on Sep. 9, 1998, now abandoned, which is a continuation-in-part of application No. 09/088,766, filed on Jun. 2, 1998, now abandoned.
(60) Provisional application No. 60/086,587, filed on May 22, 1998.

(51) Int. Cl.$^7$ ...................... A61K 38/00; A61K 39/395
(52) U.S. Cl. ...................................... 514/2; 424/130.1
(58) Field of Search ........................... 424/130.1; 514/2

(56) References Cited

U.S. PATENT DOCUMENTS

| | | | |
|---|---|---|---|
| 5,260,301 A | 11/1993 | Nakanishi et al. | 514/291 |
| 5,391,481 A | 2/1995 | Chess et al. | 424/144.1 |
| 5,788,966 A | 8/1998 | Chess et al. | 435/7.24 |

FOREIGN PATENT DOCUMENTS

| | | |
|---|---|---|
| WO | WO 97/11718 | 4/1997 |
| WO | WO 98/48024 | 10/1998 |

OTHER PUBLICATIONS

Hillis, G.S., Roy–Chaudhury, P., Duthie, L.A., Stewart, K.N., Brown, P.A., Simpson, J.G. & MacLeod, A.M. (1997). Expression of β1 integrins in IgA nephropathy. *Nephrol. Dial. Transplant* 12, 1137–1142.
Kagami, S., Kondo, S., Urushihara, M., Löster, K., Reutter, W., Saijo, T., Kutamura, A., Kobayashi, S. & Kuroda, Y. (2000). Overexpression of α1β1 integrin directly affects rats mesangial cell behavior. *Kidney Int.* 58, 1088–1097.
Kagami, S. et al., (1997). Intervention of anti–thymocyte antibody–induced glomerulonephritis (anti–Thy1 GN) by monoclonal antibody (MAB) to a1–integrin subunit S. *Journal of the American Society of Nephrology*, vol. 9, 518A (Abstract No. A2409).
Kagami, S., Kuhara, T., Yasutomo, K., Okada, K., Löster, K., Reutter, W. & Kuroda, Y. (1996). Transforming growth factor–β (TGF–β) stimulates the expression of β1 integrins and adhesion by rat mesangial cells. *Exp. Cell Res.* 229, 106.
Kapasi, A.A., Gibbons, N., Mattana, J. & Singhal, P.C. (2000). Morphine stimulates mesangial cell TNF–α and nitrite production. *Inflammation* 24, 463–476.
Korhonen, M., Ylänne, J., Laitinen, L. & Virtanen, I. (1990). The $\alpha_1$–$\alpha_6$ subunits of integrins are characteristically expressed in distinct segments of development and adult human nephron. *J. Cell Biology* 111, 1245–1254.
Kriz, W., Elger, S., Lemley, K.B. & Sakai, T. (1990). Mesangial cell–glomerular basement membrane connections counteract glomerular capillary and mesangium expansion. *Am. J. Nephrol.* 10, 4–13.
Kriz, W., Gretz, N. & Lemley, K.V. (1998). Progression of glomerular diseases: Is the podocyte the culprit? *Kidney Int.* 54, 687–697.
Pagtalunan, M.E., Miller, P.L., Jumping–Eagle, S., Nelson, R.G., Myers, B.D., Rennke, H.G., Coplon, N.S., Sun, L. & Meyer, T.W. (1997). Podocyte loss and progressive glomerular injury in type II diabetes. *J. Clin. Invest.* 99, 342–348.
Patey, N., Halbwachs–Mecarelli, L., Droz, D., LeSavre, P. & Noel, L.H. (1994). Distribution of Integrin subunits in normal human kidney. *Cell Adhesion and Communication* 2, 159–167.
Schocklmann, H., Lang, S. & Sterzel, R.B. (1999). Regulation of mesangial cell proliferation. *Kidney Int.* 56, 1199–1207.
Waldherr, R., Cuzic, S. & Noronha, I.L. (1992). Pathology of the Human mesangium in situ. *Clin. Investig.* 70, 865–874.
Yamanaka, N. & Shimizu, A. (1999). Role of glomerular endothelial damage in progressive renal disease. *Kidney Blood Press Res.* 22, 13–20.
Kagami et al. *Exp. Cell Res.*, 229, 1–6, Jan. 1996.*
Border, W.A., Okuda, S., Languino, L.R., Sporn, M.B. & Ruoslahti, E. (1990). Suppression of experimental glomerulonephritis by antiserum against transforming growth factor b1. *Nature* 346, 371–374.
Cosgrove, C., Rodgers, K., Meehan, D., Miller, C., Bovard, K., Gilroy, A., Gardner, H., Kotelianski, V., Gotwals, P., Amatucci, A. & Kalluri, R. (2000). Integrin a1b1 and transforming growth factor–β1 play distinct roles in Alport glomerular pathogenesis and serve as dual targets for metabolic therapy. *Am. J. Path.* 157, 1649–1659.
Ellis, E.N., Warady, B.A., Wood, E.G., Hassanein, R., Richardson, W.P., Lane, P.H., Howard, C., Kemp, S.F., Aceto, T., Garibaldi, L., Wiegmann, T.B. & Savin, V.J. (1997). Renal structural–functional relationships in early diabetes mellitus. *Pediatr. Nephrol.* 11, 584–591.

(List continued on next page.)

*Primary Examiner*—Michael Borin
(74) *Attorney, Agent, or Firm*—Mueting, Raasch & Gebhardt, P.A.

(57) ABSTRACT

The present invention provides methods for treating (i.e., delaying the onset of, slowing the progression of, and/or reversing) kidney disorders (e.g., renal glomerulonephritis and/or renal fibrosis). Certain of these methods involve administering an α1β1 integrin receptor inhibitor optionally in combination with a TGF-β1 inhibitor. The present invention also provides a mouse model for kidney disease wherein the mouse does not express a normal collagen type 4 composition in the GBM (i.e., it does not incorporate collagen α3(IV), α4(IV), and α5(IV) chains into its glomerular basement membrane) and does not express the α1β1 integrin receptor.

16 Claims, 24 Drawing Sheets

(1 of 24 Drawing Sheet(s) Filed in Color)-

OTHER PUBLICATIONS

Gardner, H., Kreidberg, J., Koteliansky, V. & Jaenisch, R. (1996). Deletion of Integrin α1 by homologous recombination permits normal murine development but gives rise to specific deficit in cell adhesion. *Dev. Bio.*, 175, 301–313.

Gilbert, R.E., Kelly, D.J., McKay, T., Chadban, S., Hill, P.A., Cooper, M.E., Atkins, R.C. & Nikolic–Paterson, D.J. (2001). PDGF signal transduction inhibition ameliorates experimental mesangial proliferative glomerulonephritis. *Kidney Int.* 59, 1324–1332.

Haas, C.S., Schocklmann, H.O., Lang, S., Kralewski, M. & Sterzel, R.B. (1999). Regulatory mechanism in glomerular mesangial cell proliferation. *J. Nephrol.* 12, 405–415.

Setty et al., "Glucose–Induced Alteration of Integrin Expression and Function in Cultured Human Mesangial Cells," *Cell Adhesion and Communication*, 3:187–200 (1995).

Burns and Bretschschneider, *Thin is in: plastic embedding of tissue for light microscopy*, Educational Products Division, American Society of Clinical Pathologists, Chicago, IL, pp. 24–25, 1981.

Miner et al., "The Laminin α Chains: Expression, Developmental Transitions, and Chromosomal Locations of α1–5, Identification of Heterotrimeric Laminins 8–11, and Cloning of a Novel α3 Isoform," *J. Cell Biol.*, 137:65–701 (1997).

Adler, "Characterization of Glomerular Epithelial Cell Matrix Receptors," *Am. J. Pathol.*, 141:571–578 (1992).

Akagi et al., "Inhibition of TGF–β1 expression by antisense oligonucleotides suppressed extracellular matrix accumulation in experimental glomerulonephritis," *Kidney Int.*, 50:148–155 (1996).

Apte et al., "Gene Encoding a Novel Murine Tissue Inhibitor of Metalloproteinases (TIMP), TIMP–3, is Expressed in Developing Mouse Epithelia, Cartilage, and Muscle, and is Located on Mouse Chromosome 10", *Developmental Dynamics*, 200:177–197 (1994).

Atkins et al., "Alport Syndrome," *Diseases of the Kidney*, 4th ed., Little, Brown, and Company, Boston, MA, Chap. 19, pp.617–641 (1988).

Baraldi et al., "Beta–1 Integrins in the Normal Human Glomerular Capillary Wall: An Immunoelectron Microscopy Study," *Nephron*, 66:295–301 (1994).

Barker et al., "Identification of Mutations in the COL4A5 Collagen Gene in Alport Syndrome," *Science*, 248:1224–1227 (1990).

Border et al., "Suppression of experimental glomerulonephritis by antiserum against transforming growth factor β1," *Nature*, 346:371–374 (1990).

Border et al., "Transforming Growth Factor–β in Disease: The Dark Side of Tissue Repair", *J. Clin. Invest.*, 90:1–7 (1992).

Bradley, "Production and analysis of chimaeric mice," *Teratocarcinomas and embryonic stem cells, a practical approach*, ed. E.J. Robertson, IRL Press Limited, Oxford, England, Chapter 5, pp. 113–151 (1987).

Butkowski et al., "Localization of the Goodpasture Epitope to a Novel Chain of Basement Membrane Collagen," *J. Biol. Chem.*, 262:7874–7877 (1987).

Callis et al., "Effect of cyclosporin A on proteinuria in patients with Alport's syndrome," *Pediatr. Nephrol.*, 6:140–144 (1992).

Cangiotti et al., "Evolution of glomerular basement membrane lesions in a male patient with Alport syndrome: ultrastructural and morphometric study," *Nephrol. Dial. Transplant.*, 11:1829–1834 (1996).

Cheng et al., "Self–assembly of Laminin Isoforms," *J. Biol. Chem.*, 272:31525–31532 (1997).

Cosgrove et al. "Expression of basement membrane type IV collagen chains during postnatal development in the murine cochlea," *Hearing Research*, 100:21–32 (1996).

Cosgrove et al., "Collagen COL4A3 knockout: a mouse model for autosomal Alport syndrom," *Genes and Development*, 10:2981–2992 (1996).

Crabtree, "Genetic Signals and Specific Outcomes: Signaling through $Ca^{2+}$, Calcineurin, and NF–AT," *Cell*, 96:611–614 (1999).

Daha et al., "Synthesis and Degradation of Glomerular Basement Membrane in Rats with Nephrotoxic Nephritis," *Nephron*, 22:522–528 (1978).

Delcommenne et al., "Control of Integrin Expression by Extracellular Matrix," *J. of Biological Chemistry*, 270:26794–26801 (1995).

DeSimone, "Adhesion and matrix in vertebrate development," *Curr. Opin. Cell Biol.*, 6:747–751 (1994).

Desjardins et al, "Ontogenesis of Glomerular Basement Membrane: Structural and Functional Properties," *J. Cell. Biol.*, 113:689–700 (1991).

Ding et al., "A monoclonal antibody marker for Alport syndrome identifies the Alport antigen as the α5 chain of type IV collagen," *Kidney Int.*, 46:1504–1506 (1994).

Doi et al., "Receptor–specific increase in extracellular matrix production in mouse mesangial cells by advanced glycosylation end products in mediated via platelet–derived growth factor," *Proc. Natl. Acad. Sci. USA*, 89:2873–2877 (1992).

Deutzmann et al., "Structural study of long arm fragments of laminin," *Eur. J. Biochem.*, 177:35–45 (1988).

Eble et al., "Recombinant Soluble Human $\alpha_3\beta_1$ Integrin: Purification, Processing, Regulation, and Specific Binding to Laminin–5 and Invasin in a Mutually Exclusive Manner," *Biochemistry*, 37:10945–10955 (1998).

Elliot et al., "Pentosan Polysulfate Decreases Proliferation and Net Extracellular Matrix Production in Mouse Mesangial Cells," *J. Am. Soc. Nephrol.*, 10:62–68 (1999).

Esposito et al., "Inhibition of diabetic nephropathy by a GH antagonist: A molecular analysis," *Kidney Internationa*, 50:506–514 (1996).

Fabbri et al., "A functional monoclonal antibody recognizing the human alpha1–integrin I–domain," *Tissue Antigens*, 48:47–51 (1996).

Gardner et al., "Deletion of Integrin α1 by Homologous Recombination Permits Normal Murine Development but Gives Rise to a Specific Deficit in Cell Adhesion," *Development Biology*, 175:301–313 (1996).

Goldberg et al., "Human 72–kilodalton type IV collagenase forms a complex with a tissue inhibitor of metalloproteases designated TIMP–2," *Proc. Natl. Acad. Sci. USA*, 86:8207–8211 (1989).

Goyal et al., "Fibronectin mRNA and Protein Accumulation, Distribution, and Breakdown in Rabbit Anti–Glomerular Basement Membrane Disease," *J. Am. Soc. Nephrol.*, 1:1334–1342 (1991).

Gunwar et al., "Glomerular Basement Membrane," *J. Biol. Chem.*, 266:15318–15324 (1991).

Horiguchi et al., "Distribution, Ultrastructural Localization, and Ontogeny of the Core Protein of a Heparan Sulfate Proteoglycan in Human Skin and Other Basement Membranes," *J. Histochem. Cytochem.*, 37:961–970 (1989).

Horwitz, "Integrins and Health," *Scientific American*, 68–75 (May 1997).

Hostikka et al., "Indentification of a distinct type IV collagen α chain with restricted kidney distribution and assignment of its gene to the locus of X chromosome–linked Alport syndrome," *Proc. Natl. Acad. Sci. USA*, 87:1606–1610 (1990).

Hudson et al., "Molecular characteristics of the Goodpasture autoantigen," *Kidney Int.*, 43:135–139 (1993).

Hudson et al., "Pathology of glomerular basement membrane nephropathy," *Curr. Opin. In Nephrology and Hypertension*, 3:334–339 (1994).

Hunter et al., "A laminin–like adhesive protein concentrated in the synaptic cleft of the neuromuscular junction," *Nature*, 338:229–234 (1989).

Hynes, "Integrins: Versatility, Modulation, and Signaling in Cell Adhesion," *Cell*, 69:11–25 (1992).

Kashtan et al., "Nephritogenic Antigen Determinants in Epidermal and Renal Basement Membranes of Kindreds with Alport–type Familial Nephritis," *J. Clin. Invest.*, 78:1035–1044 (1986).

Klahr et al., "The Progression of Renal Disease," *N. Engl. J. Med.*, 318:1657–1666 (1988).

Kleppel et al., "Evidence for Separate Networks of Classical and Novel Basement Membrane Collagen: Characterization of α3(IV)–Alport Heterodimer," *J. Biol. Chem.*, 267:4137–4142 (1992).

Kleppel et al., "Human Tissue Distribution of Novel Basement Membrane Collagen," *Am. J. Pathol.*, 134:813–825 (1989).

Koller et al., "Inactivating the β2–microglobulin locus in mouse embryonic stem cells by homologous recombination," *Proc. Natl. Acad. Sci. USA*, 86:8932–8935 (1989).

Korhonen et al., "Distribution of $\beta_1$ and $\beta_3$ Integrins in Human Fetal and Adult Kidney," *Lab. Invest.*, 62:616–625 (1990).

Koya et al., "Characterization of Protein Kinase Cβ Isoform Activation on the Gene Expression of Transforming Growth Factor–β, Extracellular Matrix Components, and Prostanoids in the Glomeruli of Diabetic Rats," *J. Clin. Invest.*, 100:115–126 (1997).

Kreidberg et al., "Alpha 3 beta 1 integrin has a crucial role in kidney and lung organogenesis," *Development*, 122:3537–3547 (1996).

Krishnamurti et al., "Integrin–Mediated Interactions between Primary/T–sv40 Immortalized Human Glomerular Epithelial Cells and Type IV Collagen," *Lab. Invest.*, 74:650–657 (1996).

Lemmink et al., "Mutations in the type IV collagen α3 (COL4A3) gene in autosomal recessive Alport syndrome," *Hum. Mol. Gene.*, 3:1269–1273 (1994).

Ljubimov et al., "Basement Membrane Components Produced by a Mouse Ascites Teratocarcinoma TB 24," *Exp. Cell Res.*, 165:530–540 (1986).

Mann et al., "Amino acid sequence of mouse nidogen, a multidomain basement membrane protein with binding activity for laminin, collagen IV and cells," *EMBO Journal*, 8:65–72 (1989).

Miller et al., "Complementary DNA Cloning of the Murine Transforming Growth Factor–β3 (TGFβ3) Precursor and the Comparative Expression of TGFβ3 and TGFβ1 Messenger RNA in Murine Embryos and Adult Tissues," *Molecular Endocrinology*, 3:1926–1934 (1989).

Miner et al., "Collagen IV α3, α4, and α5 Chains in Rodent Basal Laminae: Sequence, Distribution, Association with Laminins, and Developmental Switches," *J. Cell. Biol.*, 127:879–891 (1994).

Mochizuki et al., "Identification of mutations in the α3(IV) and α4(IV) collagen genes in autosomal recessive Alport syndrome," *Nature Genet.*, 8:77–81 (1994).

Muthukumaran et al., "The Complete Primary Structure for the α1–Chain of Mouse Collagen IV," *J. Biol. Chem.*, 264:6310–6317 (1989).

Noonan et al., "Identification of cDNA Clones Encoding Different Domains of the Basement Membrane Heparan Sulfate Proteoglycan," *J. Biol. Chem.*, 263:16379–16387 (1988).

Palmiter et al., "Cell Lineage Ablation in Transgenic Mice by Cell–Specific Expression of a Toxin Gene," *Cell*, 50:435–443 (1987).

Park et al., "Expression of Transforming Growth Factor–β and Type IV Collagen in Early Streptozotocin–Induced Diabetes," *Diabetes*, 46:473–480 (1997).

Patey et al., "Distribution of Integrin Subunits in Normal Human Kidney," *Cell Adhesion and Communication*, 2:159–167 (1994).

Razzaque et al., "Distribution and cellular origin of type III, type IV and type VI collagens in tubulointerstitial damage in various renal diseases," *Clin. Nephrol.*, 46:213–215 (1996).

Regoli et al., "Alterations in the expression of the $\alpha_3\beta_1$ integrin in certain membrane domains of the glomerular epithelial cells (podocytes) in diabetes mellitus," *Diabetologia* 40:15–22 (1997).

Reponen et al., "Molecular Cloning of Murine 72–kDa Type IV Collagenase and Its Expression during Mouse Development," *J. Biol. Chem.*, 267:7856–7862 (1992).

Rohrback et al., "Molecular Aspects of Basement Membrane Pathology," in *Molecular and Cellular Aspects of Basement Membranes*, pp. 385–419, Academic Press (1993).

Roy et al., "Increased Expression of Basement Membrane Collagen in Human Diabetic Retinopathy," *J. Clin. Invest.*, 93: 438–442 (1994).

Rupprecht et al., "Cell–matrix interactions in the glomerular mesangium," *Kidney Int.*, 49:1575–1582 (1996).

Sasaki et al., "Sequence of the cDNA encoding the laminin B1 chain reveals a multidomain protein containing cysteine–rich repeats," *Proc. Natl. Acad. Sci. USA*, 84:935–939 (1987).

Sasaki et al., "The Laminin B2 Chain Has a Multidomain Structure Homologous to the B1 Chain," *J. Biol. Chem.*, 262:17111–17117 (1987).

Saus et al., "The Complete Primary Structure of Mouse α2(IV) Collagen," *The Journal of Biological Chemistry*, 264:6318–6324 (1989).

Shimizu et al., "Cloning and sequencing of the cDNA encoding a mouse tissue inhibitor of metalloproteinase–2," *Gene*, 114:291–292 (1992).

Smoyer et al., "Regulation of podocyte structure during the development of nephrotic syndrome," *J. Mol. Med.*, 76:172–183 (1998).

Solez et al., "Histopathologic Findings From 2–Year Protocol Biopsies From a U.S. Multicenter Kidney Transplant Trial Comparing Tacrolimus Versus Cyclosporine," *Transplantation*, 66:1736–1740 (1998).

Staskus et al., "The 21–kDa Protein Is a Transformation–sensitive Metalloproteinase Inhibitor of Chicken Fibroblasts," *J. Biol. Chem.*, 266:499–454 (1991).

Stetler–Stevenson et al., "Tissue Inhibitor of Metalloproteinase (TIMP–2): A New Member of the Metalloproteinase Inhibitor Family," *J. Biol. Chem.*, 264:17374–17378 (1989).

Timpl, "Structure and biological activity of basement membrane proteins," *Eur. J. Biochem.*, 180:487–502 (1989).

Tryggvason et al., "Molecular genetics of Alport syndrome," *Kidney Int.*, 43:38–44 (1993).

Wada et al., "Cloning of Mouse Integrin $\alpha_v$ cDNA and Role of the $\alpha_v$–related Matrix Receptors in Metanephric Development," *J. Cell. Biol.*, 132:1161–1176 (1996).

Wang et al., "The Immunophilin FKBP12 Functions as a Common Inhibitor of the TGFβ Family Type I Receptors," *Cell*, 86:435–444 (1996).

Wilson et al., "Abnormalities in Extracellular Matrix Regulation in Autosomal Dominant Polycystic Kidney Disease," *Contrib. Nephrol.*, 118:126–134 (1996).

Yagi et al., "Homologous recombination at c–fyn locus of mouse embryonic stem cells with use of diphtheria toxin A–fragment gene in negative selection," *Proc. Natl. Acad. Sci. USA*, 87:9918–9922 (1990).

Yamada et al., "Differential mRNA Regulation of Integrin Subunits $\alpha_v$, $\beta_1$, $\beta_3$, and $\beta_5$ during Mouse Embryonic Organogenesis," *Cell Adhesion and Communication*, 3:311–325 (1995).

Yamamoto et al., "Sustained expression of TGF–β1 underlies development of progressive kidney fibrosis," *Kidney Int.*, 45:916–927 (1994).

Yang et al., "Overexpression of Transforming Growth Factor–β1 mRNA Is Associated With Up–Regulation of Glomerular Tenascin and Laminin Gene Expression in Nonobese Diabetic Mice," *J. Am. Soc. Nephrol.*, 5:1610–1617 (1995).

Yoshioka et al., "Glomerular localization of type III collagen in human kidney disease," *Kidney Int.*, 35:1203–1211 (1989).

Zhou et al., "Deletion of the Paired α5(IV) and α6(IV) Collagen Genes in Inherited Smooth Muscle Tremors," *Science*, 261:1167–1169 (1993).

* cited by examiner

7wk SV/J α1 integrin nAb

USE OF α1β1 INTEGRIN RECEPTOR INHIBITORS AND TGF-β1 INHIBITORS IN THE TREATMENT OF KIDNEY DISEASE

CROSS-REFERENCE TO RELATED APPLICATIONS

The present application is a Continuation-In-Part of U.S. patent application Ser. No. 09/150,485, filed on Sep. 9, 1998 now abandoned, which is a Continuation-In-Part of U.S. patent application Ser. No. 09/088,766, filed on Jun. 2, 1998 now abandoned, which claims the benefit of U.S. Provisional Application Serial No. 60/086,587, filed on May 22, 1998.

"STATEMENT OF GOVERNMENT RIGHTS

This invention was made with government support under a grant from the National Institutes of Health, Grant No. RO1DK55000. The U.S. Government may have certain rights in this invention."

FIELD OF THE INVENTION

This invention relates to the field of kidney disease (i.e., kidney disorder) characterized by glomerulonephritis and/or fibrosis. In particular, this invention relates to the use of α1β1 integrin receptor inhibitors in kidney disorders. Further, this invention relates to the use of α1β1 integrin inhibitors in combination with TGF-β1 inhibitors in kidney disorders.

BACKGROUND OF THE INVENTION

In the United States, approximately 12,000 people currently live with Alport syndrome. This inherited disorder results in progressive renal disease that is only treatable by dialysis and kidney transplant. Transplanted kidneys are usually rejected. Thus, alternative treatments are needed. However, there is currently no treatment that addresses the mechanism of the disease onset or progression. Thus, what is needed is a treatment method that attacks the mechanism of disease onset and/or progression, one that could substantially slow disease conditions, such as renal glomerulonephritis and renal fibrosis.

A number of kidney diseases are associated with alterations in matrix homeostasis, where the delicate balance of synthesis and turnover of structural molecules is interrupted. As one example, Alport syndrome is a disease resulting in progressive renal failure and is associated with sensorineural hearing loss. Male carriers are most affected and ultrastructural studies reveal abnormalities in the glomerular basement membrane (GBM) of affected individuals. About one in 20,000 people have Alport syndrome, making the disease one of the more prevalent known genetic disorders. See, for example, Atkin et al., "Alport Syndrome" In R. W. Schrier & C. W. Gottschalk (Eds.), *Diseases of the Kidney*, 4th ed., Chap. 19, Little Brown, Boston, pp. 617–641, 1988. X-linked Alport syndrome is caused by any of a series of mutations in the collagen 4A5 gene (Barker et al., *Science*, 248:1224–1227, 1990). At least 60 different mutations in the gene have been identified. The autosomal form of Alport syndrome displays the same range of phenotypes as the X-linked form and results from mutations in either basement membrane collagen gene 4A3 (COL4A3) or 4A4 (COL4A4). See, for example, Lemmink et al., *Hum. Mol. Gen.*, 3:1269–1273, 1994, and Mochizuki et al., *Nature Genet.*, 8:77–81, 1994. Other diseases of the basement membrane include Goodpasture syndrome, which is due to an acute autoimmune response directed against an epitope on the NCl domain of collagen 4A3 (Hudson et al., *Kidney Int.*, 43:135–139, 1993), and diffuse leiomyomatosis, a benign smooth muscle tumor that is associated with a deletion of both collagen 4A5 and 4A6 (Zhou et al., *Science*, 261:1167–1169, 1993).

Basement membranes are specialized extracellular structures associated with nearly every organ and tissue in the body. They are usually found at the boundary between cells and connective tissue, but may also be found between epithelial and endothelial cells, as is the case in a kidney glomerulus (i.e., cluster of capillaries). The predominant building blocks of basement membranes include type IV collagen, laminin, heparin sulfate proteoglycan, entactin, and sometimes fibronectin and type V collagen. The most highly represented component in all basement membranes is type IV collagen, a distinct collagen type found only in basement membranes. In its native form, type IV, like all collagens, is composed of three collagen molecules assembled in a triple helix consisting of distinct combinations of the six alpha chains (4A1–4A6). The 4A1 and 4A2 chains (also referred to as the α1(IV) and α2(IV) chains) are the most common (Timp1, *Eur. J. Biochem.*, 180:487–502, 1989). Type IV collagens differ from interstitial collagens in a number of ways. The helical structure of the alpha chain association does not strictly adhere to the glycine-X-Y motif observed in other collagens; it contains 3-hydroxyproline rather than 4-hydroxyproline, and is rich in carbohydrate. The resulting superstructure of collagen is a chicken wire-like network of basement membrane collagen. This network is the foundation onto which the accessory molecules (laminin, heparin sulfate, etc.) bind.

Basement membranes are very heterogeneous structures, which accounts for their diverse functional properties. The complexity of these structures is still poorly understood. Several novel basement membrane collagen chains (alpha 3, 4, 5, and 6 chains) were only recently discovered. See, for example, Gunwar et al., *J. Biol. Chem.*, 266:15318–15324, 1991; Hostikka et al., *Proc. Natl. Acad. Sci. USA*, 87:1606–1610, 1990; Butkowski et al., *J. Biol. Chem.*, 262:7874–7877, 1987; and Zhou et al., *Science*, 261:1167–1169, 1993. Interestingly, the novel chains have been found only in certain tissues (e.g., the glomerulus of the kidney, the Decimet's membrane of the eye, the lens, the skin, the lung, the testis, and the cochlea). See, for example, Kleppel et al., *Am. J. Pathol.*, 134:813–825, 1989, and Tryggvason et al., *Kidney Int.*, 43:38–44, 1993. The role of these novel chains in basement membrane assembly and function is currently unknown. It is believed that these novel basement membrane collagens form separate networks distinct from the networks of collagen types 4A1 (α1(IV)) and 4A2 (α2(IV)).

Kidney glomerular basement membranes (GBMs) are integral to the ultrafiltration process (i.e., in which blood is filtered to remove metabolites for excretion in the form of urine, for example). Alport syndrome results in a massive accumulation of extracellular matrix and a compromised basement membrane, resulting in focal and segmental glomerulonephritis (i.e., inflammation of the capillary loops in the glomeruli of the kidney), which ultimately results in fatal uremia (i.e., excess urea in the blood as a result of kidney failure). Many of the same extracellular matrix molecules (e.g., collagen type I, fibronectin, laminin, and collagen type IV) also progressively accumulate in the GBM of patients with IDDM (insulin dependent diabetes mellitus) nephritis. In this disease, however, the GBM thickens, but lacks the focal thinning and splitting (segmenting) of the GBM, which is characteristic of Alport syndrome.

The integrins are a family of heterodimeric transmembrane glycoprotein receptors that bind to components of basal lamina and extracellular matrix. They function as adhesion molecules involved in cell aggregation and in anchoring cells to basal lamina. They also transduce signals to the nucleus, and are involved in modulating gene expression, particularly gene expression for cell migration and cell differentiation (Hynes, *Cell,* 69:11–25, 1992). Over 20 different integrin receptors are known, which include about 14 different alpha subunits and about 8 different beta subunits (DeSimone, *Curr. Opin. Cell Biol.,* 6:747–751, 1994).

In the renal (kidney) glomerulus, there are distinct sets of integrin receptors. These are associated with either the mesangial matrix (i.e., a membrane that helps support the capillary loops in a kidney glomerulus) or visceral epithelial cells (Patey et al., *Cell Adhesion Commun.,* 2:159–167, 1994). The most prevalent integrin receptor on adult glomerular visceral epithelial cells is the $\alpha 3\beta 1$ heterodimer (Adler, *Am. J. Pathol.,* 141:571–578, 1992; and Patey et al., *Cell Adhesion Commun.,* 2:159–167, 1994). The $\beta 5$ subunit has been shown to be expressed in adult visceral epithelial cells (Yamada et al., *Cell Adhesion Communic.,* 3:311–325, 1995), and the $\alpha 1$, $\alpha 3$, $\alpha 5$, $\alpha V$, $\beta 1$, and $\beta 3$ integrin receptors are expressed developmentally during kidney morphogenesis (Korhonen et al., *Lab. Invest.,* 62:616–625, 1990; Wada et al., *J. Cell. Biol.,* 132:1161–1176, 1996; and Yamada et al., *Cell Adhesion Communic.,* 3:311–325, 1995). The $\alpha 1\beta 1$ heterodimeric integrin receptor is the only integrin receptor identified on the surface of mesangial cells in the renal glomerulus.

A gene knockout mouse at the $\alpha 3$ integrin receptor subunit has been produced. The offspring die of kidney dysfunction shortly after birth (Kreidberg et al., *Dev.,* 122:3537–3547, 1996). The ultrastructural pathology of the GBM in the neonates of this model is remarkably similar to that observed in advanced Alport syndrome. The basement membrane appears rarefied (i.e., irregularly thickened, thinned, and split) and the foot processes of the visceral epithelial cells appear fused. Since one ligand for the $\alpha 3\beta 1$ receptor is type IV collagen (Krishnamurti et al., *Lab. Invest.,* 74:650–657, 1996; and Rupprecht et al., *Kidney Int.,* 49:1575–1582, 1996), and since this receptor localizes along the plane of contact between visceral epithelial cells and the GBM (Baraldi et al., *Nephron,* 66:295–301, 1994), the observations listed above for the $\alpha 3$ integrin knockout support a model where such integrin/ligand interactions play an important role in basement membrane development.

In a normal animal, the type IV collagen in embryonic glomerular basement membrane (GBM) up to the time of birth is comprised entirely of the $\alpha 1(IV)$ and $\alpha 2(IV)$ chains (referred to as the classical collagen chains). Shortly after birth, a developmental switch occurs where the $\alpha 3(IV)$, $\alpha 4(IV)$, and $\alpha 5(IV)$ chains (referred to as the novel collagen chains) are clearly detectable in the GBM, and the $\alpha 1(IV)$ and $\alpha 2(IV)$ chains become predominantly localized to the mesangial matrix (Miner & Sanes, *J. Cell. Biol.,* 127:879–891, 1994).

In the adult kidney a thin layer of GBM comprised of the $\alpha 1(IV)$ and $\alpha 2(IV)$ chains lies adjacent to the endothelial cell layer, while the majority of the full thickness of the GBM is comprised of the $\alpha 3(IV)$, $\alpha 4(IV)$, and $\alpha 5(IV)$ chains (Desjardins & Bendayan, *J. Cell. Biol.,* 113:689–700, 1991; and Kashtan et al., *J. Clin. Invest.,* 78:1035–1044, 1986). There is biochemical evidence suggesting that the two different sets of collagen chains form separate networks (Kleppel et al., *J. Biol. Chem.,* 267:4137–4142, 1992). In familial nephritis, null mutations (i.e., mutations that destroy gene expression) in either the $\alpha 3(IV)$, the $\alpha 4(IV)$, or the $\alpha 5(IV)$ genes results in the absence of all three chains in the GBM, presumably due to obligatory associations in macromolecular assembly of the GBM suprastructure. This results in the presence of $\alpha 1(IV)$ and $\alpha 2(IV)$ chains throughout the full thickness of the GBM. Thus, type IV collagen receptors on the surface of visceral epithelial cells in the Alport kidney (i.e., the kidney of an individual with Alport syndrome) are in direct contact with a GBM of uncharacteristic type IV collagen chain composition. At least one study has addressed the relative ability of the visceral epithelial cells to adhere to type IV collagen with these different compositions, and found that they adhere significantly better to basement membrane comprised of the novel chains when compared directly with the classical chains $\alpha 1(IV)$ and $\alpha 2(IV)$. This adhesion could be blocked with antibodies against the $\alpha 3$ integrin receptor.

A mouse model for the autosomal form of Alport syndrome was created by targeted mutagenesis of the COL4A3 procollagen gene (Cosgrove et al., *Genes Dev.,* 10:2981–2992, 1996). The animal model develops a progressive glomerulonephritis with the onset of proteinuria at about four weeks of age and a mean age of death from renal failure at about 8.5 weeks in the inbred 129 Sv/J background. Ultrastructural changes in the GBM are observed as early as one week of age, and throughout the GBM of most glomeruli by 3 weeks of age, long before the onset of proteinuria. Extracellular matrix components including laminin-1, heparin sulfate proteoglycan, fibronectin, and entactin accumulate in the GBM. This mouse is referred to herein as the "Alport" mouse.

The accumulation of extracellular matrix in the GBM and the mesangium as a function of renal disease progression is a feature shared by a variety of glomerular diseases, both in patients and in experimental animal systems. See, for example, Goyal & Wiggins, *Am. Soc. Nephrol.,* 1:1334–1342, 1991; Wilson et al., *Contrib. Nephrol. Basel, Karger,* 118:126–134, 1996; Razzaque et al., *Clin. Nephrol.,* 46:213–215, 1996; Yoshioka et al., *Kidney Int.,* 35:1203–1211, 1989; and Klahr et al., *N. Engl. J. Med.,* 318:1657–1666, 1988. In diabetes, the primary mediator of this effect is thought to be prolonged exposure to non-enzymatically glucosylated serum proteins resulting from chronic high glucose levels (Doi et al., *Proc. Natl. Acad. Sci. USA,* 89:2873–2877, 1992; and Roy et al., *J. Clin. Invest.,* 93: 483–442, 1994).

For the majority of progressive glomerular disorders, over-production of the transforming growth factor TGF-$\beta 1$ seems to be closely associated with the accumulation of extracellular matrix leading to fibrosis (i.e., the formation of fibrous tissue). See, for example, Border & Ruoslahti, *Nature* (London), 346:371–374, 1990; Yang et al., *J. Am. Soc. Nephrol.,* 5:1610–1617, 1995; and Yamamoto et al., *Kidney Int.,* 45:916–927, 1994. In an animal model for autoimmune nephritis, injection with either antibodies to TGF-$\beta 1$, or antisense oligonucleotides to the corresponding mRNA inhibited the progressive glomerulonephritis and the accumulation of extracellular matrix (Border et al., *Nature* (London), 346:371–374, 1990; and Akagi et al., *Kidney Int.,* 50:148–155, 1996).

The half-life of basement membrane collagen in the GBM of the rat has been estimated at between 16 and 40 days based on pulse-chase studies with $^3$H-proline (Daha et al., *Nephron.* 22:522–528, 1978). This is very slow in relation with the turnover of heparin sulfate proteoglycans ($t_{1/2}$=20 hours) or other sulfated macromolecules in the GBM ($t_{1/2}$=

20–60 hours). The accumulation of basement membrane proteins in the GBM of the Alport mouse model (Cosgrove et al., *Genes Dev.*, 10:2981–2992, 1996) is likely the net effect of changes in both the synthesis and the degradation of these proteins. Of the proteases involved in the turnover of both GBM and mesangial matrix, the most characterized are the metalloproteinases MMP-2 (72 kD collagenase) and MMP-9 (92 kD collagenase), as well as MMP-3 (stromolysin-1). These enzymes will degrade type IV collagen, in addition to a variety of other extracellular matrix components.

Mesangial cells (and probably other glomerular cell types) also produce natural inhibitors to the metalloproteinases. These are called TIMP's (for Tissue Inhibitors of MetalloProteinases). These are relatively low molecular weight glycoproteins. Of these, TIMP-1 is specific for stromolysin-1 and MMP-9, while TIMP-2 and TIMP-3 will inhibit MMP-2 (Goldberg et al., *Proc. Natl. Acad. Sci. USA*, 86:8207–8211, 1989; Staskus et al., *J. Biol. Chem.*, 266:449–454, 1991; and Stetler-Stevenson et al., *J. Biol. Chem.*, 264:17374–17378, 1989).

Modulation of the metalloproteinases and their corresponding inhibitors likely play a role in maintaining appropriate levels of GBM turnover. While little is known regarding the regulation of the genes encoding these proteins in the glomerulus, signal transduction via integrin receptor/ECM (extracellular matrix) interaction may be a key aspect in this process.

There remains a need for animal models for Alport syndrome, particularly one in which the disease progression is slowed significantly. There also remains a need for new therapies to treat kidney diseases associated with mesangial matrix expansion, and progressive matrix accumulation in the glomerular basement membrane and the tubulointerstitium, including Alport syndrome and insulin dependent diabetes mellitus, for example.

SUMMARY

The present invention provides various treatment methods for treating or limiting (i.e., delaying the onset of, slowing the progression of, and/or reversing) a kidney disorder in a patient (preferably, a mammal, and more preferably, a human). The kidney disorder preferably includes renal glomerulonephritis, renal fibrosis, or both. These conditions can be associated with, for example, Alport syndrome, IDDM nephritis, mesangial proliferative glomerulonephritis, membrano proliferative glomerulonephritis, crescentic glomerulonephritis, diabetic nephropathy, and renal insterstitial fibrosis.

In one embodiment, the method involves administering to the patient an effective amount of an $\alpha 1\beta 1$ integrin receptor inhibitor. This $\alpha 1\beta 1$ integrin receptor inhibitor can be a blocking agent that binds to the $\alpha 1\beta 1$ integrin receptor binding site on the surface of a kidney cell. The blocking agent can be an at least 9-mer peptide fragment of a protein selected from the group consisting of laminin, fibronectin, entactin, and collagen type 4. Alternatively, the blocking agent can be an antibody. Other agents that inhibit (i.e., inactivate) the $\alpha 1\beta 1$ integrin receptor by other mechanisms can also be used.

In another embodiment, the method involves administering to the patient an effective amount of a TGF-$\beta 1$ hibitor in addition to the $\alpha 1\beta 1$ integrin receptor inhibitor. These inhibitors can be administered simultaneously (e.g., as in a mixture) or sequentially. The TGF-$\beta 1$ inhibitor can be an agent that irreversibly binds to TGF-$\beta 1$ and inhibits its ability to bind with its receptor. Alternatively, the TGF-$\beta 1$ inhibitor can be an agent that inhibits the ability of TGF-$\beta 1$ to transduce signals to the nucleus of a kidney cell. The latter type of inhibitor is preferably a calcineurin inhibitor, such as tacrolimus (commercially available as FK506). Other agents that inhibit (i.e., inactivate) TGF-$\beta 1$ by other mechanisms can also be used.

Preferably, the present invention provides methods for delaying the onset of and/or slowing the progression of Alport syndrome in a patient. In one embodiment, this method involves administering an effective amount of an agent that inhibits signal transduction through an $\alpha 1\beta 1$ integrin receptor of a kidney cell. In another embodiment, this method involves blocking an $\alpha 1\beta 1$ integrin receptor binding site on the surface of a kidney cell of the patient. These methods can be further enhanced by administering to the patient an effective amount of a TGF-$\beta 1$ inhibitor.

Preferably, the present invention also provides methods for delaying the onset of and/or slowing the progression of kidney disease in insulin dependent diabetes mellitus in a patient. In one embodiment, this method involves administering an effective amount of an agent that inhibits signal transduction through an $\alpha 1\beta 1$ integrin receptor of a kidney cell. In another embodiment, this method involves blocking an $\alpha 1\beta 1$ integrin receptor binding site on the surface of a kidney cell. These methods can be further enhanced by administering to the patient a TGF-$\beta 1$ inhibitor.

Further, methods are provided for limiting renal fibrosis in a patient. In one embodiment, the method involves reducing TGF-$\beta 1$ activity in the patient while inhibiting $\alpha 1\beta 1$ integrin receptors of the patent's kidney cells. This activity can be reduced by administering to the patient an agent that irreversibly binds to TGF-$\beta 1$ and inhibits its ability to bind with its receptor. Alternatively, this activity can be reduced by administering to the patient an agent capable of inhibiting the ability of TGF-$\beta 1$ to transduce signals to the nucleus of a kidney cell.

In yet another embodiment, methods are provided for limiting matrix accumulation in the GBM of a patient with Alport Syndrome. In one embodiment, the method involves reducing TGF-$\beta 1$ activity in the patient. This can be accomplished by administering TGF-$\beta 1$ inhibitors as described herein.

In a particularly preferred embodiment, a method is provided for limiting renal fibroses by administering to a patient a calcineurin inhibitor, preferably tacrolimus.

Further, the present invention provides a mouse model for kidney disease wherein the mouse does not express a normal collagen type 4 composition in the GBM as a result of knocking out the collagen $\alpha 3$(IV) gene. That is, the mouse does not incorporate the collagen $\alpha 3$(IV), $\alpha 4$(IV), or $\alpha 5$(IV) chains into the glomerular basement membrane (thus the GBM is comprised entirely of collagen $\alpha 1$(IV) and $\alpha 2$(IV) chains, with respect to its type IV collagen chain composition). Furthermore, it does not express the $\alpha 1\beta 1$ integrin receptor a result of knocking out the $\alpha 1$ subunit gene.

In the double knockout mouse there is delayed onset of proteinuria as compared to the prior art Alport mouse model. Furthermore, the animal lives nearly twice as long as Alport littermates. At about 8 weeks of age, which is the average age of death in Alport mice, the double knockout shows markedly reduced glomerular pathology. That is, as compared to Alport mice of the same age, the double knockout mouse has markedly reduced ultrastructural damage with far less GBM rarefication and very little effacement of the podocyte foot processes. Also, attenuated accumulation of fibronectin, laminin-1, and heparan sulfate proteoglycan in the GBM occur, while accumulation of entactin and type IV collagen are unchanged, relative to Alport mice. These results indicate that there is a specific role for the α1β1 integrin receptor in Alport renal disease pathogenesis. This is remarkable, considering that the single α1 integrin knockout has no obvious effect on renal physiology or function.

This mouse can be used for studying Alport syndrome, insulin dependent diabetes mellitus, and other disorders that are characterized by glomerulone phritis and/or fibrosis. This mouse can also be used for screening for agents that can be used to treat Alport syndrome and insulin dependent diabetes mellitus and other disorders that are characterized by deposition of extracellular matrix and/or fibrosis.

BRIEF DESCRIPTION OF THE FIGURES

"The patent or application file contains at least one drawing executed in color. Copies of this patent or patent application publication with color drawing(s) will be provided by the Office upon request and payment of the necessary fee."

Figure 1:
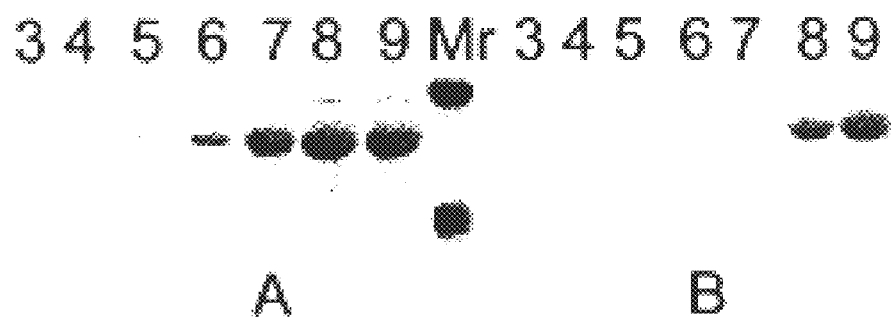
FIG. 1 illustrates the onset of proteinuria in Alport versus double mutant mice, which was studied by collecting urine from the mice at weekly intervals. Numbers indicated the age (in weeks) of the mice at the time of urine collection. A=Alport mouse; B=double mutant mouse; Mr=molecular weight standards.

"The patent or application file contains at least one drawing executed in color. Copies of this patent or patent application publication with color drawing(s) will be provided by the Office upon request and payment of the necessary fee."

DETAILED DESCRIPTION OF THE PREFERRED EMBODIMENTS

The present invention provides treatment methods that attack the mechanism of renal disease (i.e., kidney disease), one that could substantially slow the onset of and/or progression of disease conditions, such as glomerulonephritis and renal fibrosis. It is believed that the methods of the present invention could even reverse such conditions. In particular, the invention provides methods for the treatment of kidney disease associated with the presence of or an increased risk for developing glomerulonephritis and renal fibrosis in the kidney glomeruli, such as occurs in mesangial proliferative glomerulonephritis, membrano proliferative glomerulonephritis, crescentic glomerulonephritis, diabetic nephropathy, and renal insterstitial fibrosis. Glomerulonephritis involves glomerular damage typically associated with thickening, thinning, and/or splitting irregularities in the GBM. This can culminate in the common pathway of tubulointerstitial fibrosis. These conditions are typically characterized by the appearance of myofibroblasts and the accumulation of matrix (including collagen type I, fibronectin, laminin, and collagne type IV) in the tubulointerstitium. The effectiveness of the therapeutic agents used in the methods of the present invention can be determined by evaluating one or more of these characteristics.

The invention also provides a mouse model for the study of methods and the screening of agents for treating patients with kidney disease associated with the presence of, or an increased risk for, developing an accumulation of extracellular matrix generally, and particularly within the kidney glomeruli and the tubulointerstitium. Thus, in one embodiment, the present invention provides a mouse model for Alport syndrome. This mouse model includes an inactivated α1β1 integrin receptor in combination with an inactivated collagen (type IV) molecule. In a preferred embodiment, the collagen (type IV) molecule is inactivated through disruption of expression of the α3 subunit of collagen (type IV). As a result, the mouse does not incorporate the collagen α3(IV), α4(IV), or α5(IV) chains into the GBM.

This mouse model can be used in methods for testing agents to treat renal dysfunction, as it occurs in Alport syndrome, insulin dependent diabetes mellitus, and other renal diseases where early disease is characterized by the expansion of the mesangial matrix and mesangial cell proliferation in association with glomerular basement membrane damage, characterized by basement membrane thickening, thinning, splitting, and effacement of the podocyte foot processes, or any combination thereof.

In a preferred embodiment, the invention provides inhibitors to block or otherwise inactivate the function of the α1β1 integrin receptor as a method for delaying the onset of (as measured by the appearance of albumin in the urine) or slowing the progression of (as measured by the rate at which the level of serum albumin in the urine increases) or even reversing (as measured by the rate at which the level of serum albumin in the urine increases) glomerulonephritis and/or fibrosis (as manifest by the appearance of myofibroblasts and the accumulation of extracellular matrix, including laminin, fibronectin, collagen type I, and collagen type IV in the tubulointerstitium) in the progression of glomerular disease. A variety of agents, synthetic or natural, can be used, which are described in greater detail below.

In yet another embodiment, the invention is directed to the role of TGF-β1 in Alport renal disease pathogenesis and other such kidney diseases. A pronounced increase in mRNA levels for TGB-β1 following the onset of proteinuria is observed on in the mouse models used herein. In situ hybridization indicates that the podocytes, which produce little to no mRNA for TGF-β1 prior to the onset of proteinuria, express an abundance of mRNA for TGF-β1 following the onset of proteinuria up until end stage renal failure. Activation of mRNAs encoding fibronectin, COL4A1 and COL4A2, and entactin are observed at about the same time. Therefore, methods for diminishing the level of TGF-β1 is another mechanism for treating renal conditions such as glomerulonephritis and/or fibrosis. The effects of inhibiting TGF-β1 activity can be measured by determining the time point of appearance (the onset) and rate of increase of albumin in urine and/or appearance of myofibroblasts (in the tubulointerstitium) and/or accumulation of extracellular matrix molecules in the GBM and tubulointerstitium.

In another embodiment, through the use of TGF-β1 inhibitors in Alport mice deficient in α1 integrin, the invention is directed to the synergism of a combination treatment of α1β1 integrin inhibitors and TGF-β1 inhibitors at slowing the onset and progression of glomerulonephritis, and/or preventing fibrosis.

Mouse Model

An important aspect of managing patients with Alport syndrome and other diseases associated with progressive glomerular damage associated with thickening, thinning, or splitting irregularities in the GBM and culminating in the common pathway of tubulointerstitial fibrosis as characterized by the appearance of myofibroblasts and the accumulation of matrix (including collagen type I, fibronectin, laminin, and collagne type IV) in the tubulointerstitium is determining the cause and/or mechanism of the disease progression. For example, while mutations in the collagen α3(IV) or α4(IV) genes result in autosomal recessive forms of Alport syndrome, and mutations in the α5(IV) gene results in the X-linked form of the disease, these mutations themselves do not "cause" progressive renal failure. Instead, the absence of collagen α3(IV), α4(IV) or α5(IV) appears to result in the persistence of the embryonic-like GBM comprised of the α1(IV) and α2(IV) collagen chains. This embryonic-like GBM is a suitable glomerular filter for about the first decade of life in humans (or about the first three weeks in the mouse model). However, after this time the embryonic-like GBM does not appear to function effectively. For example, in one patient with Alport syndrome, ultrastructural studies of the GBM of a 9-year old patient with Alport syndrome revealed a relatively normal ultrastructure (Cangiotti et al., *Nephrol. Dial. Transplant.*, 11:1829–1834, 1996). At age 18, however, the GBM ultrastructure of the same patient indicated advanced Alport glomerulonephritis.

In Alport syndrome the basement membrane in humans is relatively normal until between five and ten years of age when the loss of basement membrane integrity can be monitored by a progressive increase in albumin in the urine. Biopsy studies have confirmed that the basement membrane ultrastructure is normal in pre-proteinuric Alport patients. Ultrastructurally, GBM disease is evidenced by an irregular thickening and thinning of the GBM. Splitting of the membrane is thought to account for microhematuria (i.e., small numbers of erythrocytes detectable in the urine) observed along with proteinuria.

Little is known regarding the mechanism of Alport renal disease onset and progression; however, it has been speculated that the accumulation of GBM components and rarefication of the GBM might be due to increased susceptibility of the membrane to proteolysis, and/or increased synthesis of matrix molecules due to alterations in the normal regulatory pathways.

Thus, there has been a need for a model for Alport syndrome because of the limitations inherent to the study of human specimen. Humans display a range of severity in the progression of the disease, presumably due to differences in genetic backgrounds. Meaningful studies that address the molecular nature of disease onset and progression are logistically impossible in humans, hampering progress in Alport renal disease research.

A mouse model for autosomal Alport syndrome was produced by targeted mutagenesis of the gene encoding the type IV collagen α3(IV) chain (Cosgrove et al., *Genes Devel.*, 10:2981–2992, 1996). The animal model developed a progressive glomerulonephritis. Ultrastructural changes in the GBM were observed as early as one week of age. This mouse is referred to herein as the "Alport" mouse.

Also, a mouse was produced by targeted mutagenesis of the gene encoding the α1 integrin receptor subunit (Gardner et al., *Dev. Biol.*, 175: 301–313, 1996). This integrin subunit forms a heterodimer with the integrin β1 subunit to form the biologically active α1β1 integrin heterodimer, which is found on the surface of mesangial cells in the renal glomerulus. The integrin α1β1 receptor is the only integrin receptor found in the mesangial matrix, where it is exclusively localized. Aside from altered adhesion of fibrocytes to collagen matrices, the knockout mouse has no obvious phenotype. It develops normally, is fertile, and lives a normal life span. There is no renal insufficiency, and no apparent differences in molecular composition or ultrastructure of the glomerulus in these mice. Because the α1β1 heterodimeric integrin receptor is the only integrin receptor identified on the surface of mesangial cells in the renal glomerulus, it was surprising that the absence of this receptor had no affect on normal renal development and/or function. This suggests that it is either not required, or that redundant pathways can compensate for its absence.

The present invention provides a new double knockout (i.e., double mutant) mouse model. This was developed by crossing the α1 knockout mouse strain with the collagen α3(IV) knockout strain (Alport mouse) to produce mutants defective in both the integrin α1 receptor subunit gene and the collagen α3(IV) gene. Although the absence of the α1β1 integrin receptor apparently does not play a role in normal renal development and function, because the mesangial matrix is the site of synthesis for the metalloproteinases and cytokines such as TGF-β1 and the early stages of Alport glomerulonephritis involve mesangial cell proliferation and expansion of the mesangial matrix, it is believed that the α1β1 integrin receptor might have a specific role in renal pathogenesis. Indeed, studies of the integrin α1 collagen α3(IV) double knockout are particularly unique and important. The following discussion describes many of the characteristics of the double knockout mouse of the present invention.

A good overall assessment of the integrity of the renal filter is proteinuria (i.e., the presence of an excess of serum proteins in the urine). As illustrated in FIG. 1, the onset of proteinuria in the double knockout was delayed by at least a week, and peaked at about 9 weeks to about 9.5 weeks versus about 6 weeks to about 6.5 weeks in littermates that were Alport (i.e., lacking the collagen α3(IV) gene, but containing the α1 integrin subunit gene). The onset and rate of increase of proteinuria (i.e., the presence of serum albumin in the urine) is a good measure for evaluating the effectiveness of the methods of the present invention. The serum albumin levels can be measured by either by gel electrophoresis and coomassie blue staining (running the equivalent of 1 microliter of urine) or commercially available stick tests. The mean age of death due to renal failure is about 8 to about 9 weeks in Alport mice regardless of whether these mice are of the 129 Sv/J or 129 Sv backgrounds (at least ten mice were allowed to progress to end stage for each genetiv background to establish this point). The double knockouts live to an average of about 15 weeks to about 16.5 weeks of age.

Therefore, removing the α1β1 integrin receptor had a marked affect on Alport renal disease onset and progression. Further, mice without the α1β1 receptor had improved glomerular function as compared to the other mice tested. In animals that did not express the α3(IV) gene and were heterozygous for the α1 knockout mutation, there was an intermediate improvement in glomerular function and disease progression illustrating that the α1 integrin had a dose dependent effect on Alport renal disease progression (i.e., reducing the α1 integrin expression by half provided a protective effect that is in between the Alport mouse and the double knockout). This intermediate protective effect in Alport animals heterozygous for the α1 integrin mutation illustrates that partially inhibiting the α1β1 integrin receptor provides useful benefits. This is a significant finding as it applies to therapies involving inhibition of the α1β1 integrin receptor when used in humans.

Figure 2:
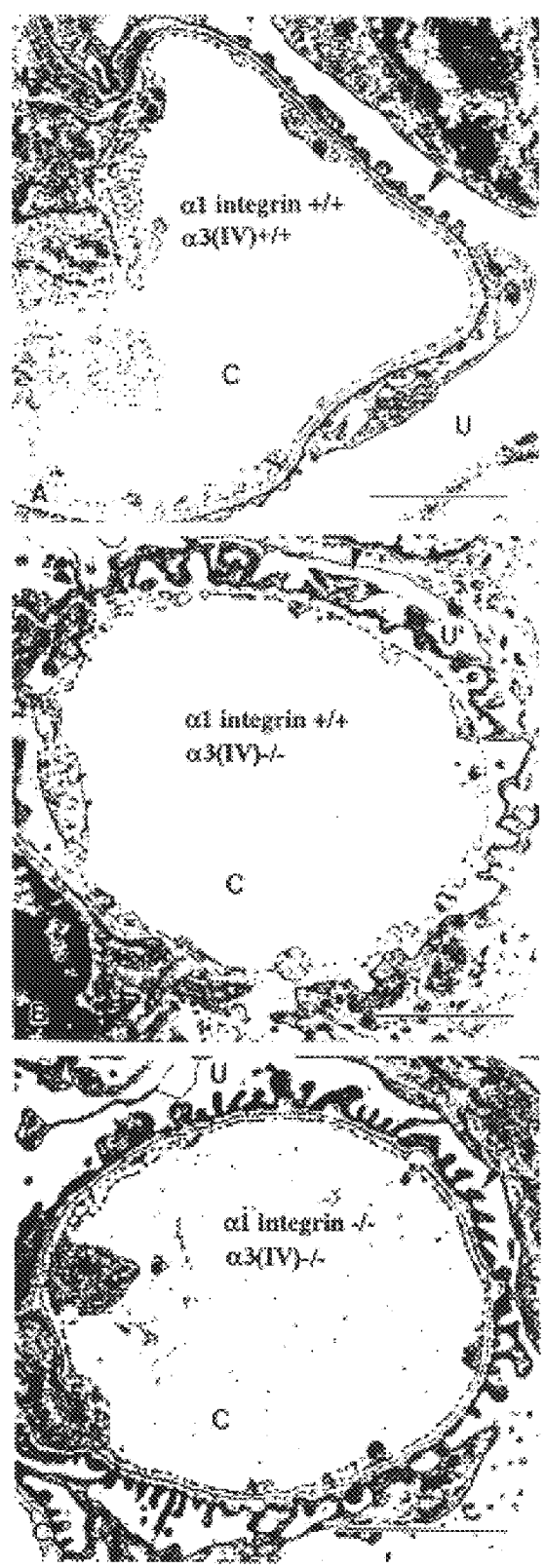
FIG. 2 illustrates the ultrastructural damage to the glomerular capillary loop in control and double mutant mice. Renal cortex from normal (A), Alport (B), and double mutant (C) mice was harvested at 7 weeks, embedded in epoxy resin. Ultrathin sections were stained and analyzed by transmission electron microscopy. Arrows denote foot processes. C=capillary lumen; U=urinary space. Magnification bars represent 0.5 μm.

Transmission electron microscopic analysis was performed on kidneys from 7 week old mice that were either normal at both alleles (control), null at collagen α3(IV) and normal at α1 integrin (Alport), or null at both collagen α3(IV) and α1 integrin (double knockout). This time point was chosen since the Alport mice at this age are approaching end stage. The panels chosen for FIG. 2 are representative of at least 5 different glomerular fields. As illustrated in FIG. 2, the glomerular capillary loop of the normal mouse (FIG. 2A) had a trilaminar basement membrane with uniform thickness and regular foot processes (the foot processes in all three panels are denoted by arrows). The capillary loop of the Alport mouse (FIG. 2B) showed rarefied basement membrane with focal thickening and thinning (characteristic of advanced disease). The foot processes were swollen, appearing fused, a property believed to affect renal filtration efficiency. In the double knockout (FIG. 2C), the basement membrane was markedly less affected than that of the Alport mouse (FIG. 2B). While the basement membrane was thinner than that of the control, it was much less rarefied, and the foot processes of the podocytes appeared largely normal. In the Alport mouse, about 40% of the glomeruli were fibrotic, while only 5% were fibrotic in the double mutant.

Figure 3:
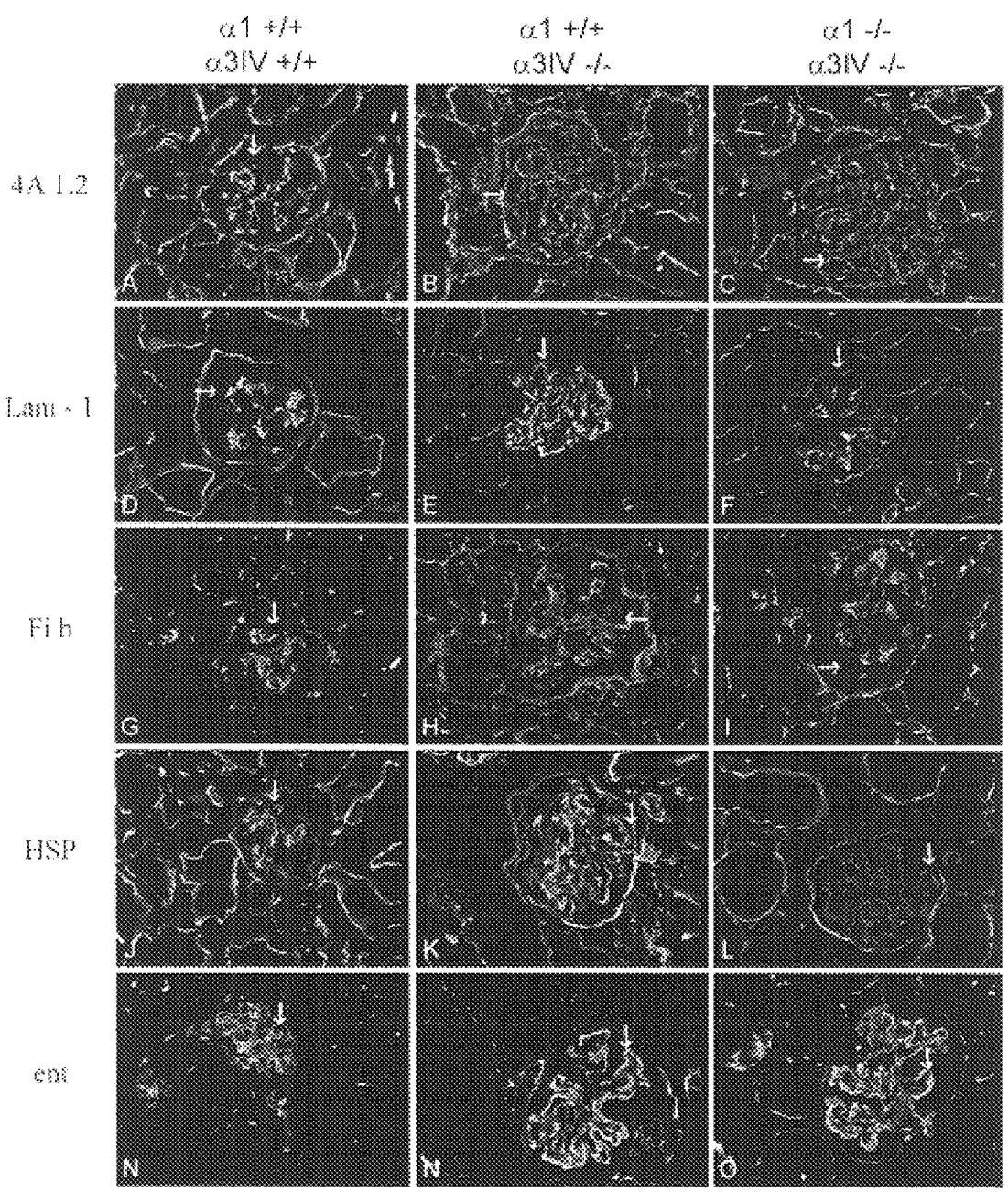
FIG. 3 provides the results of immunofluorescence analysis of extracellular matrix proteins in normal, Alport, and double mutant mice. Frozen cryosections of renal cortex were reacted with antibodies specific for the extracellular matrix proteins indicated on the Y-axis labels. Signal was developed using the appropriate fluoresceine-conjugated secondary antibody, and images collected digitally and processed using the Cytovision Ultra software (Applied Imaging, Inc.). Arrows denote glomerular capillary loops. 4A1,2=collagen α1(IV) and α2(IV) chains; Lam-1=laminin-1; Fib=fibronectin; HSP=heparin sulfate proteoglycan; ent= entactin. α1 +/+=homozygous normal at the α1 integrin gene; α1 −/−=homozygous mutant at the α1 integrin gene; α3(IV) +/+=homozygous normal at the α3(IV) collagen gene; α3(IV) −/−=homozygous mutant at the α3(IV) collagen gene.

Immunofluorescence analysis was performed using frozen renal cortex taken from the same animals used in FIG. 2. The tissue was reacted with antibodies specific for proteins known to accumulate in the GBM as a function of Alport renal disease progression. The results in FIG. 3 illustrate that the distribution of collagen COL 4A1 (α1(IV)) and 4A2 (α2(IV)) chains was the same for both the Alport glomerulus and that of the double mutant. In both cases, the capillary loops (denoted in all panels of FIG. 3 by arrows) and the mesangial matrix were positive (FIGS. 3B, C). Laminin-1 showed marked accumulation in the GBM of the Alport mouse compared to the control (Compare FIG. 3D with FIG. 3E), however in the double mutant (FIG. 3F), accumulation of laminin-1 was markedly attenuated relative to that in Alport glomeruli (FIG. 3E). Fibronectin normally localizes exclusively in the mesangial matrix, but it was found to localize to the GBM as well as the mesangial matrix in the Alport mice (FIG. 3H). Surprisingly, in the double mutant, accumulation of fibronectin in the capillary loops is not observed (FIG. 3I). This result was highly reproducible. In contrast, staining for heparin sulfate proteoglycan showed attenuated staining in the mesangial matrix of the double mutant (FIG. 3L) when compared to either the control (FIG. 3J) or the Alport mouse (FIG. 3K). Accumulation of entactin in the GBM was observed in both the Alport and double mutant samples, with no discernible difference between the two (FIGS. 3N and 3O).

Combined, these data illustrate that the α1 null mutation in the double mutant results in slowing Alport renal disease progression. This is clear at both the physiologic (delayed onset of proteinuria as shown in FIG. 1) and ultrastructural (reduced GBM damage and foot process effacement as shown in FIG. 2) levels. The immunofluorescence studies provided in FIG. 3 illustrate that elimination of the α1β1 integrin receptor results in specific changes in the accumulation of extracellular matrix components in both the GBM and the mesangial matrix. Thus, the present invention involves treatment methods wherein the α1β1 integrin receptor binding site on the surface of a kidney cell is blocked. Such treatment methods are described in greater detail below.

Figure 9:
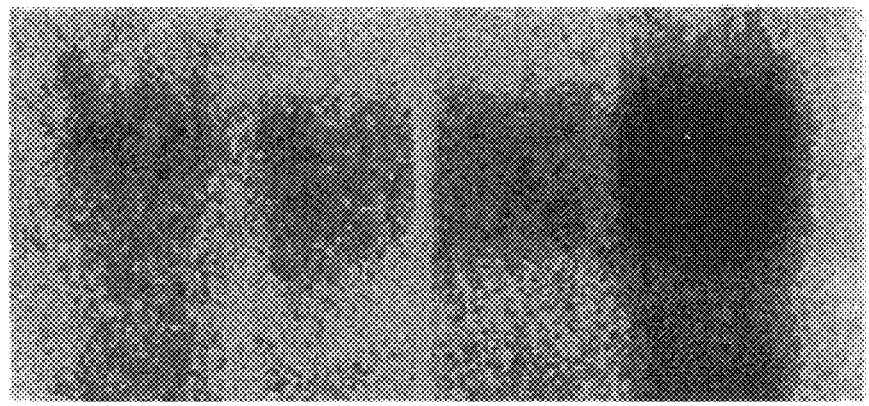
FIG. 9 illustrates northern blot of RNA from renal cortex of normal, Alport, α1 integrin deficient, and mice deficient in both α1 integrin and collagen α3(IV). Total RNA was isolated from the renal cortex of 7 week-old mice (littermates) with the indicated genotypes: +/+=normal at both alleles; −/−=mutant at both alleles.

Furthermore, FIG. 9 shows that, while the cytokine TGF-β1 is induced in the Alport mouse, it is not induced in Alport mice that harbor the α1 integrin mutation as well. Thus, in the absence of α1β1 integrin, TGF-β1 induction is not observed, which accounts for a decrease in accumulation of matrix in the glomerular basement membrane, and thus, a significant decrease in the rate at which the renal disease progresses. This role of TGF-β1 in renal disease is discussed in greater detail in the following section.

Role of TGF-β1

The data herein clearly establishes that TGF-β1 is induced in a specific glomerular cell type (the podocytes) in the mouse models used herein. The induction of TGF-β1 mRNA is mirrored by the induction of the genes encoding the matrix molecules known to accumulate in the glomerular basement membrane as a function of progressive glomerulonephritis in the model (e.g., laminin, fibronectin, entactin, and type IV collagen). Furthermore, the data herein shows that TGF-β1 is induced in human Alport renal cortex. This supports the validity of the animal model in its ability to mimic what is happening in the human Alport kidney.

Figure 4:
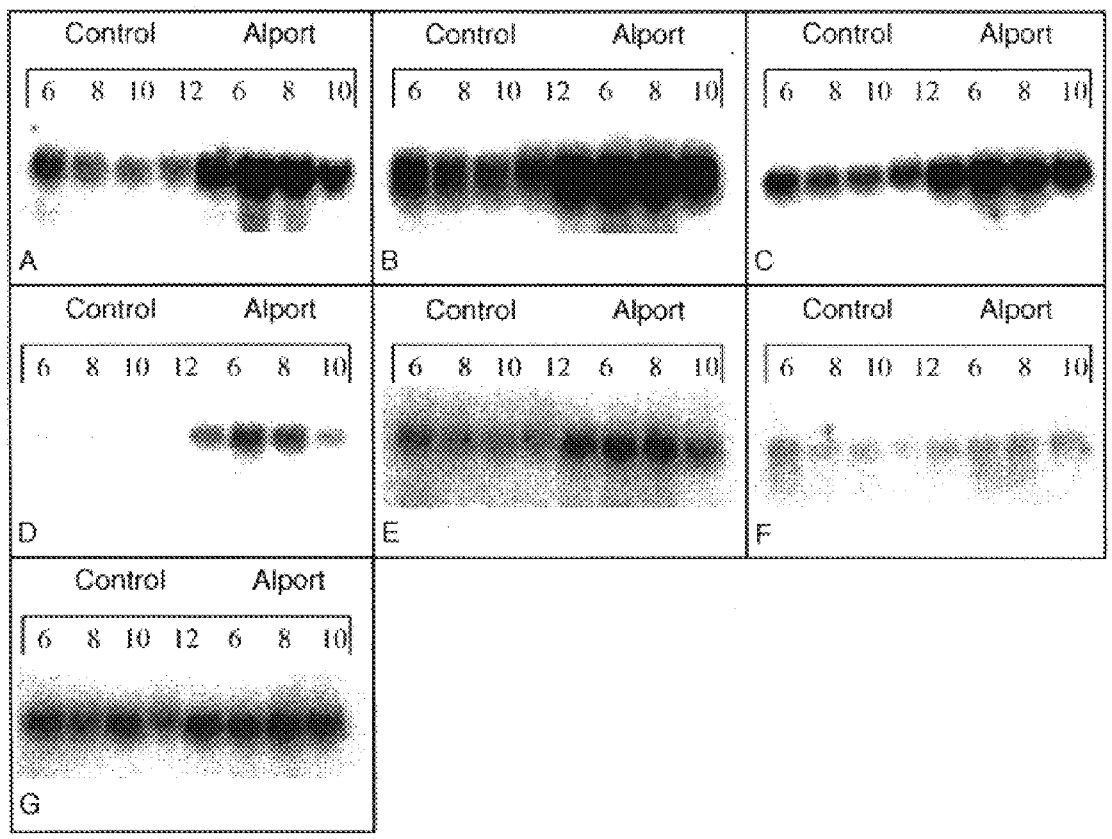
FIG. 4 shows the results of northern analysis of mRNAs from total kidney during a timecourse of Alport renal disease progression. Total RNA isolated from kidneys harvested at the indicated timepoints (in weeks) was fractionated on denaturing agarose gels, blotted onto nylon, and probed with murine cDNAs encoding either TGF-β1, or various components of the glomerular basement membrane and/or the extracellular matrix. The probes used to generate data illustrated in the panels are as follows: A, TGF-β1; B, Collagen α1(IV); C, Collagen α2(IV); D, Fibronectin; E, Entactin; F, Laminin β1 chain; G, Laminin β2 chain.

To demonstrate the role of TGF-β1, total RNA was isolated from kidneys of Alport animals and probed with radiolabeled probes specific for either the α1(IV) or α2(IV) collagen chains, entactin, the laminin β1 or β2 chain, fibronectin, or TGF-β1. The results in FIG. 4 illustrate that the mRNAs for all of these proteins with the exception of laminin β1 are induced following the onset of proteinuria in the Alport mouse model. Northern blots for this same timecourse were also performed for laminin α1, laminin β2, laminin γ1, heparin sulfate proteoglycan core protein, and the collagen α4(IV), and α5(IV) chains. No significant differences in mRNA levels for these other basement membrane proteins were apparent when comparing the control to the mutant.

Figure 5:
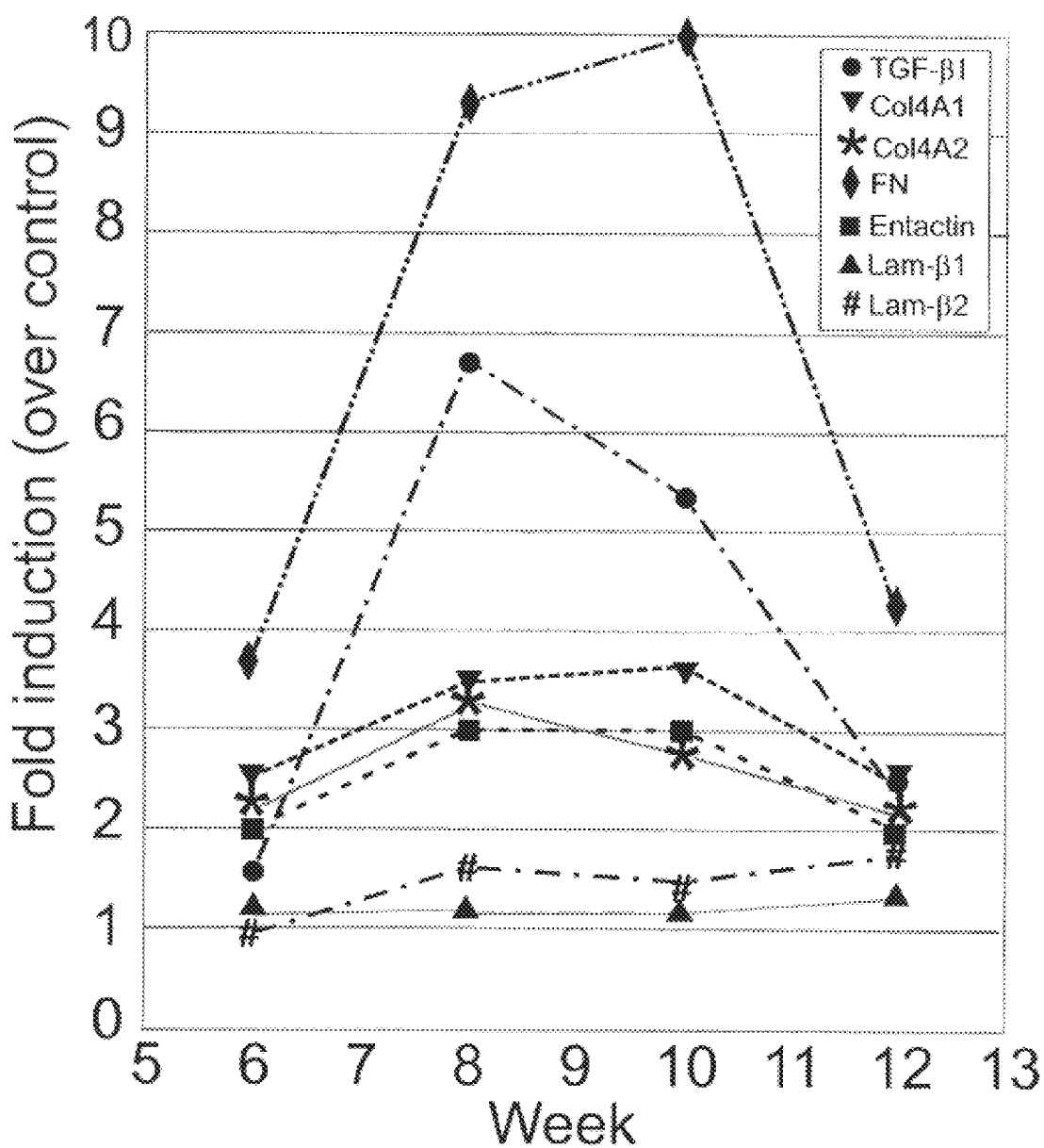
FIG. 5 illustrates the quantitative analysis of mRNA induction during Alport renal disease progression. Following exposure to X-ray film, the membranes used to produce FIG. 4 were analyzed using a BioRad GS-525 phosphorimager. Plotted values indicate fold induction of the specific mRNA in the Alport sample over those observed in the normal littermate. All bands were subtracted against the background. The specific mRNA species analyzed are denoted in the inset.

The results of the northern analyses were analyzed to directly quantify the relative changes in specific mRNA expression during the timecourse. FIG. 5 illustrates that induction of the specific mRNA levels is first apparent at six weeks of age. By 8 weeks, mRNA levels peak, with the mRNAs encoding TGF-β1 and fibronectin induced 6.6- and 9.4-fold over that of control mice, respectively. The mRNA levels for collagen α1(IV), α2(IV), and entactin were all about 3-fold induced by week 8. In contrast, no significant changes in mRNAs encoding the laminin β1 and β2 chains, as determined by these same total RNA northern blots, were observed at any point in renal disease progression.

Figure 6:
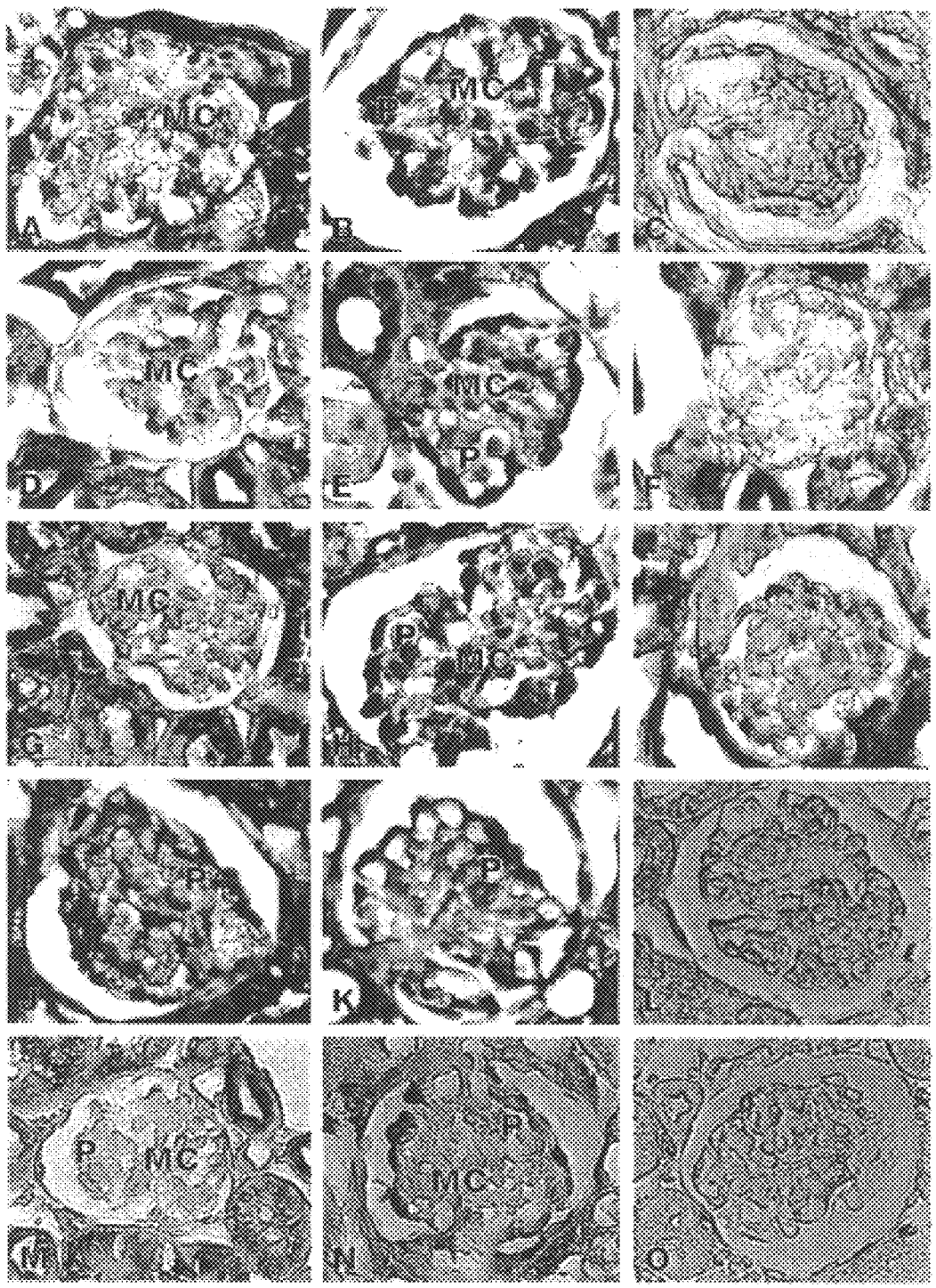
FIG. 6 illustrates in situ hybridization analysis of specific transcripts in post-proteinuric Alport mice. Kidneys from normal littermates (A, D, G, and J) were analyzed along side those from Alport mice (B, E, H, and K). Antisense probes were specific for the NCl domain of collagen α1(IV) (A and B), TGF-β1 (D and E), Fibronectin (G and H), entactin (J and K), or the laminin β1 chain (M and N). A probe specific for bacterial β-galactosidase was used as a control for non-specific binding (C, F, I, L, and O).

The glomeruli comprise only a small percentage of the total mass of the kidney. Individual cell types within the glomeruli comprise an even lesser percentage. Northern blots of total kidney RNA is therefore not likely to detect induction of messages that might be specific to glomeruli, or to a particular glomerular cell type. To examine whether the mRNAs encoding TGF-β1, or the different basement membrane components were induced in a particular glomerular cell type, in situ hybridization was performed using digoxygenin-labeled antisense probes specific for the mRNAs. The results are shown in FIG. 6. In normal mice, the transcripts for TGF-β1 (FIG. 6D), fibronectin (FIG. 6G) and laminin β1 (FIG. 6M) localize exclusively to the mesangial cells, while in the Alport mice, these same transcripts (FIGS. 6 E, H, and N, respectively) clearly localize to the podocytes (the ring of cells on the outside of the glomerulus) illustrating gene activation in this glomerular cell type. Podocyte activation of collagen α1(IV) is also evident (compare FIG. 6B with 6A). Activation of genes encoding matrix proteins in glomerular podocytes could result in changes in GBM composition.

Figure 7:
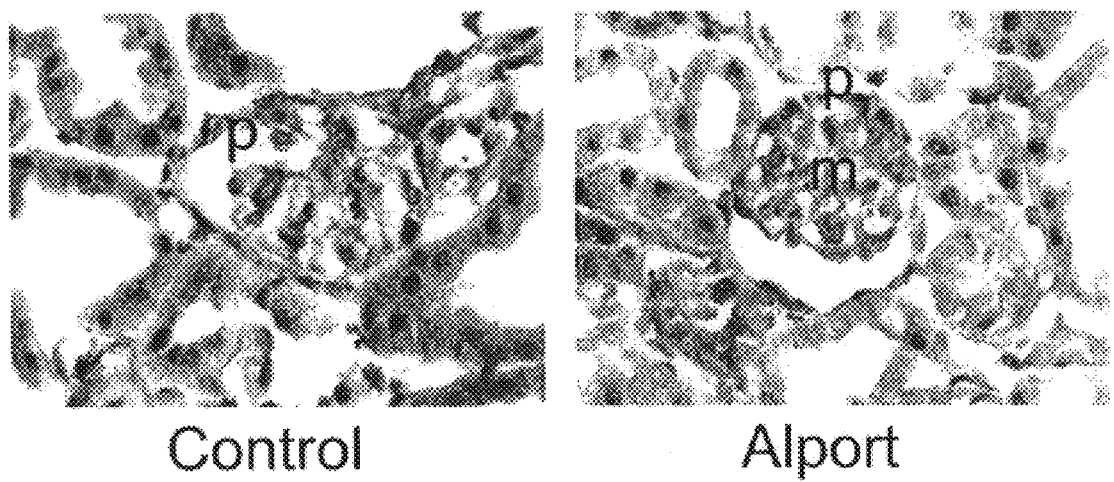
FIG. 7 illustrates immunoperoxidase staining for TGF-β1 in tissue sections from normal and Alport mice. Paraffin embedded sections stained for the active form of TGF-β1 using the immunoperoxidase detection. P=podocytes; M=mesangial cells.

TGF-β1 protein data based on immunoperoxidase detection using antibodies specific for the active isoform of the cytokine corroberate data obtained by in situ hybridization analysis for TGF-β1 messenger RNA. The data shown in FIG. 7 illustrates that elevated expression of TGF-β1 messenger RNA in the podocytes translates into elevated protein.

Figure 8:
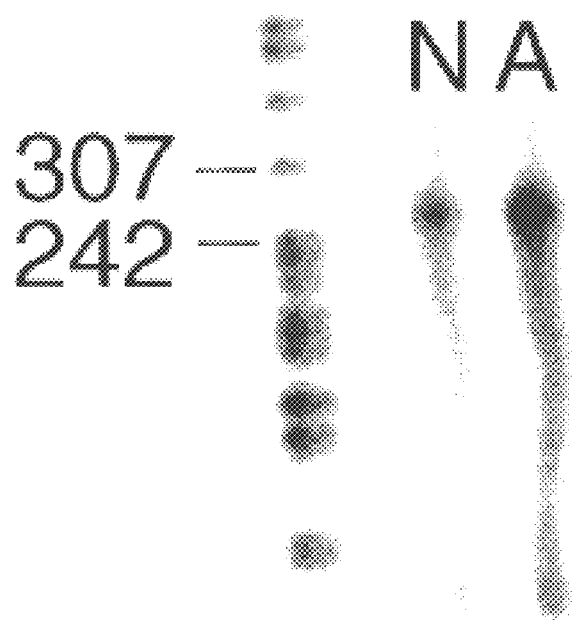
FIG. 8 illustrates RNase detection analysis for TGF-β1 mRNA in normal and Alport human renal cortex. Total RNA was isolated from normal and Alport human renal cortex, and 10 μg of each was subjected to RNase protection analysis using a radiolabeled portion of the human TGF-β1 antisense message as a probe. The assay results in a 264 bp protected fragment. Molecular size markers are radiolabeled MSP1 cut PBR322, and appropriate fragments are denoted for comparison. N=normal; A=Alport.

Since the data for TGF-β1 was acquired using a mouse model RNase protection analysis was performed to determine if mRNA levels for the cytokine are also elevated in human renal cortex from Alport versus control patients. Data in FIG. 8 illustrate a 3–4 fold elevation of TGF-β1 messenger RNA in human Alport renal cortex relative to control. This proves that the cytokine is also overexpressed in human Alport kidneys. Thus, inhibiting the activity of TGF-β1 provides a reasonable treatment protocol for Alport Syndrome, particularly for limiting, and preferably even preventing, matrix accumulation in the GBM.

As discussed above, FIG. 9 shows that, while TGF-β1 is induced in the Alport mouse, it is not induced in double knockout mice that harbor the α1 integrin mutation as well. Thus, in the absence of α1β1 integrin, TGF-β1 induction is not observed, which accounts for a decrease in accumulation of matrix in the glomerular basement membrane, and thus, a significant decrease in the rate at which the renal disease progresses.

Significantly, blocking (or otherwise inactivating) both the integrin α1β1 receptor and inhibiting TGF-β1 is synergistic in attenuating renal disease (particularly Alport renal disease) onset, progression, and/or reversal. This synergistic effect is demonstrated using, as examples, two different agents that block TGF-β1 activity in three different ways. Both were studied to assure that the results were due to inhibiting TGF-β1 activity, rather than a side effect of drug treatment.

The first example is a drug produced by Fujisawa Pharmaceutical Co., Ltd., Osaka, Japan, referred to as tacrolimus or FK506. This drug is commonly used as an immunosupressant to prevent rejection following organ transplantation. It works by inhibiting a critical subunit of the T-cell receptor called calcineurin, which is a serine threonine phosphatase, and a critical part of T-cell receptor signal transduction. As reviewed recently (Crabtree, *Cell*, 96:611–614, 1999), calcineurin is a subunit of a variety of receptors. One of these receptors was recently reported to be that for TGF-β1 (Wang et al., *Cell*, 86:435–444, 1996). The drug FK506 was tested as a TGF-β1 inhibitor. Thus, treating mice with the appropriate dose of FK506 will inhibit TGF-β1 type I/type II receptor signal transduction.

Since FK506 has other biological effects besides inhibiting TGF-β1 (potent immunosupression via T-cell receptor inhibition being the most notable), a second TGF-β1 inhibitor was evaluated. This second inhibitor is an experimental drug under development by Biogen Inc., Cambridge, Mass. This drug is a competitive inhibitor of the cytokine, soaking up the active cytokine as an inactive soluble receptor complex. It is a soluble chimeric TGF-βRII/IgG1 murine fusion protein (see, International Publication WO 98/48024). Twenty five micrograms of the inhibitor were injected into mice through the tail vein twice weekly in the described experiments.

Since the mode of activity and the potential side effects of FK506 and the soluble TGF-β1 inhibitor of Biogen are so different, observations made using the animal model systems that are consistent with both drugs are concluded to be due to the inhibition of TGF-β1 activity.

Two types of experiments were performed. Both agents were tested using the 129 Sv/J mouse model (the Alport mouse) to examine the biological effects of TGF-β1 inhibition by itself. Second, both agents were tested in the double knockout mouse model to examine the biological effects of α1β1 integrin inhibition combined with TGF-β1 inhibition. In all cases, the data presented herein was repeated at least three times with a high degree of consistency.

When TGF-β1 is inhibited in the Alport mouse model, there are some beneficial effects. There is overall improvement of basement membrane morphology, however, significant foot process effacement is still observed. Thus, TGF-β1 can improve GBM morphology by reducing the rate of matrix accumulation, but it has no significant affect on the mechanisms underlying foot process effacement. This means that TGF-β1 inhibitors given alone, although provide improvement, are not likely to succeed in improving all characteristics of Alport Syndrome or other such disorders. In double knockout mice, by 10 weeks of age, most of the foot processes look normal, however there is significant matrix accumulation in the GBM. If you treat these same animals with any of the TGF-β1 inhibitors used starting at 4 weeks of age, and harvest tissues at 10 weeks of age, about 30% of glomeruli are ultrastructurally indistinguishable from those of normal mice. Thus, significant improvement in treatment protocols described herein can be achieved using TGF-β1 inhibitors in combination with α1β1 integrin receptor inhibitors.

Figure 21:
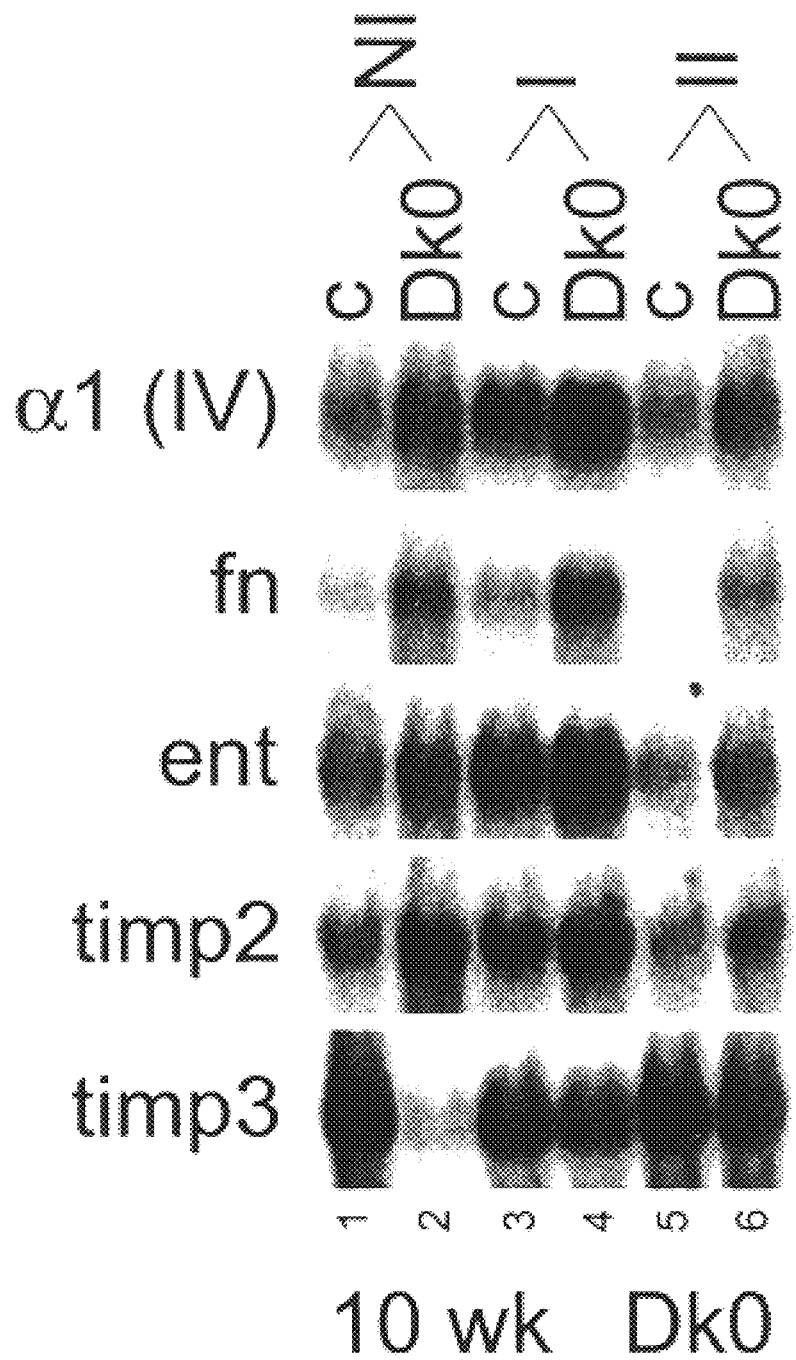
FIG. 21 demonstrates the effect of TGF-β1 inhibitors on expression, in the kidney, of RNAs encoding cell matrix molecules or metalloproteinase inhibitors in normal versus double knockout mice. Total RNA was isolated from kidneys of 10 week old normal (C) or double knockout (Dko) mice, that were either treated with FK506 (I), the TGF-β1 soluble receptor (II), or not treated (NI). RNA's were fractionated on denaturing agarose gels, and analyzed by hybridization to radiolabeled probes encoding either extra-cellular matrix molecules or metalloproteinase inhibitors. Following hybridization, membranes were washed and exposed to X-ray film. Probes used are indicated to the left of the panels. α1(IV)=collagen α1(IV); fn=fibronectin; ent=entactin; Timp2=metalloproteinase inhibitor Timp-2; Timp3=metalloproteinase inhibitor Timp-3.

Northern blot data on specific mRNAs from kidneys taken from either Alport mice or double knockouts treated with either of the TGF-β1 inhibitors, demonstrate that there are distinct differences between how either TGF-β1 or the α1β1 integrin knockout mutation affects expression of these messages that encode either matrix molecules that accumulate in the GBM. The mRNAs encoding metalloproteinases (including matrix metalloproteinase 2(MMP-2)) and their corresponding inhibitors (including TIMP-2 and TIMP-3), that are believed to modulate the rate of turnover of molecules that comprise the GBM, are also differentially affected in Alport mice versus double knockout mice treated with either of the TGF-β1 inhibitors. Specifically, Timp-3, which is expressed at very high levels in normal mice is suppressed in the both Alport mice and double knockouts. Treatment with double knockout mice with TGF-β1 inhibitors prevents suppression of TIMP-3, restoring the mRNA to levels comparable to those observed in control mice (FIG. 21).

Figure 18:
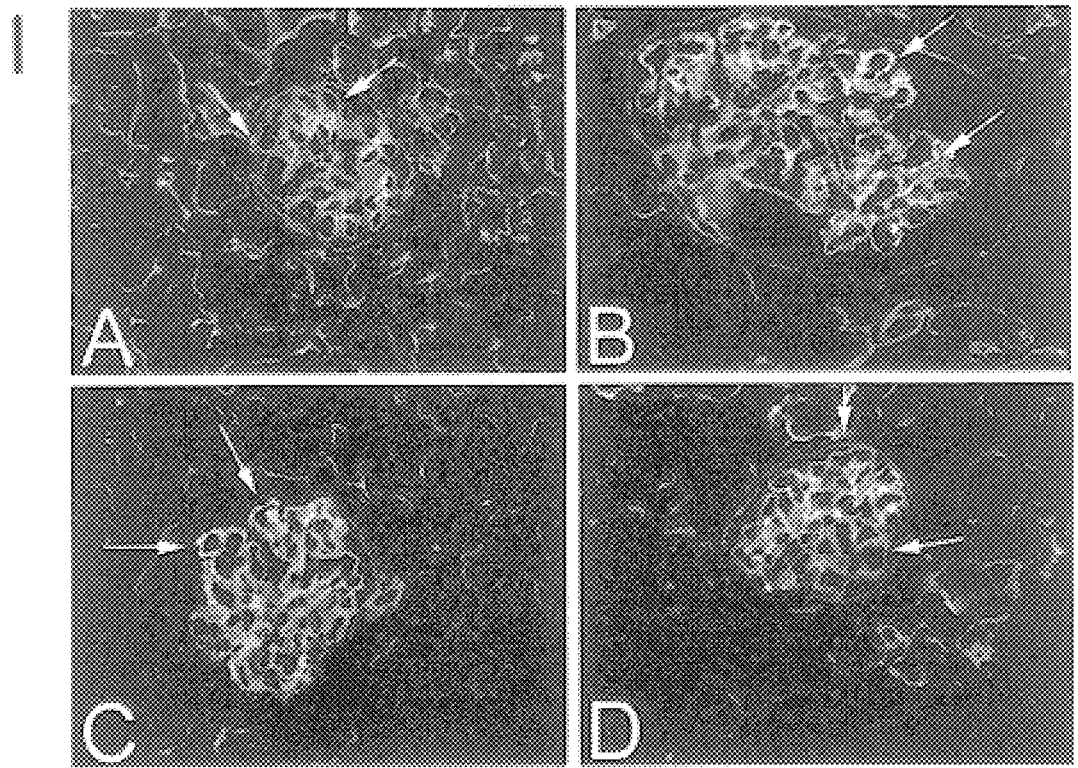
FIG. 18 shows dual immunofluorescence staining for the laminin α2 chain in normal and mutant mice. The glomerular basement membrane was stained in green using an entactin-specific primary antibody and an FITC-conjugated secondary antibody. Laminin α2 chain was stained in red using a Texas red-conjugated secondary antibody. Co-localization in the capillary loops results in yellow staining. Group I are glomeruli from 7 week old mice; A=uninjected control; B=uninjected Alport; C=Alport injected with the soluble receptor; D=uninjected double knockout. Group II are glomeruli from 2 week old mice; A=control; B=Alport. The arrows denote immunostaining in the capillary loops of the glomeruli.
Figure 18:
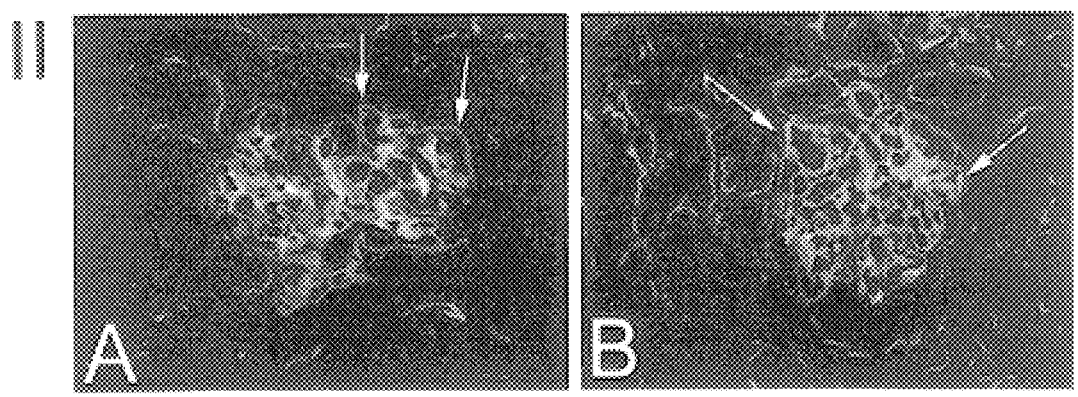

Along these same lines, laminin α2 expression is normally tightly restricted to the mesangial matrix. The deposition of laminin α2 is the earliest molecular change identified in association with Alport GBM disease onset, showing up at the same time as basement membrane thickening is first detected. Deposition of laminin α2 in the GBM of double knockout mice is not observed even at 7 weeks of age (FIG. 18, Group 1D). Administration of TGF-β1 inhibitors to the SV/J Alport mice does not inhibit deposition of laminin α2 (FIG. 18, Group 1C). This underscores another difference in how α1β1 integrin versus TGF-β1 functions in slowing disease progression, substantiating with hard evidence why a combination treatment provides synergistic benefits.

It is believed that the failure of TGF-β1 to inhibit effacement of the podocyte foot processes is directly linked to the observations regarding laminin α2. The laminins form heterotrimers consisting of an alpha, beta, and gamma chain. In the basement membrane, they crosslink with one another to form a sheet-like superstructure that is an integral part of the basement membrane. The laminins are known to interact with integrin receptors, and play important roles in differentiation and maintenance of tissue function. In normal mice, the GBM contains predominantly laminin-11, a heterotrimer of α5, β2, and γ1 chains. This laminin is known to bind with high affinity to the integrin α3β1 receptor on the surface of podocytes. Many believe that this interaction plays a key role in maintaining the complex cytoskeletal architecture that forms the foot processes. Laminin heterotrimers that contain the α2 chain (laminin-2 and laminin-4) do not bind to α3β1 integrin. Thus the presence of the laminin-2 chain in the GBM might result in the observed foot process effacement by inhibiting the binding of the α3β1 integrin to its normal substrate (laminin-11). As mentioned, in the double knockout, the deposition of laminin α2 is inhibited, which correlates well with the maintenance of foot processes in this mouse strain.

Additional observations relate to the issue of interstitial fibrosis. Interstitial fibrosis occurs late in Alport syndrome progression. In the 129 Sv/J Alport mouse model, little fibrosis is observed prior to 7 weeks, with a mean age of death at 8 weeks. In the double knockout, however, onset of fibrosis is at 8 to 9 weeks, and progresses until the mean age of death at 15 weeks. Thus, the double knockout is an excellent model for the study of fibrosis. There is a significant course of fibrosis in the double knockout mouse, and this can be largely prevented by using TGF-β1 inhibitors.

Treatment Methods

In one aspect, the invention relates to the use of inhibitors (e.g., blocking agents) to block or otherwise inactivate the function of the α1β1 integrin receptor as a method for delaying the onset (as measured by the appearance of detectable levels of serum albumin in the urine, using either a commercially available stick test or gel electrophoresis and gel staining procedure) slowing the progression of (as determined by measuring the rate at which albumin levels increase in the urine as a function of time, as measured above), or even reversing glomerular disease, particularly progressive glomerular nephritis and/or fibrosis. These include, for example, at least 9-mer peptides from proteins that bind to the α1β1 integrin receptor, such as, but not limited to, laminin, type IV collagen, fibronectin, and entactin. Small molecules binding within the receptor/ligand site of the α1β1 receptor can be created based on protein/α1β1 integrin receptor studies. Antibodies and antibody fragments that specifically bind to the binding site of the α1β1 integrin receptor can be used in this invention. These antibodies or antibody fragments include polyclonal, monoclonal, anti-idiotype, animal-derived, humanized and chimeric antibodies.

An agent (artificial ligand) that blocks the binding site for the α1β1 integrin receptor can be used in the methods of the present invention. Examples of such agents include, but are not limited to, a neutralizing antibody, peptide, proteolytic fragment, or the like. Such agents are believed to block signal transduction through the receptor. Effectiveness of such treatments can be determined by evaluating the downstream effects on gene expression of, for example, TGF-β1, fibronectin, laminin chains, etc., by the morphometric changes in the glomerular basement membranes, and/or by improvement in the glomerular seive as evidenced by a decrease in the rate of onset and progression of proteinuria.

Figure 10:
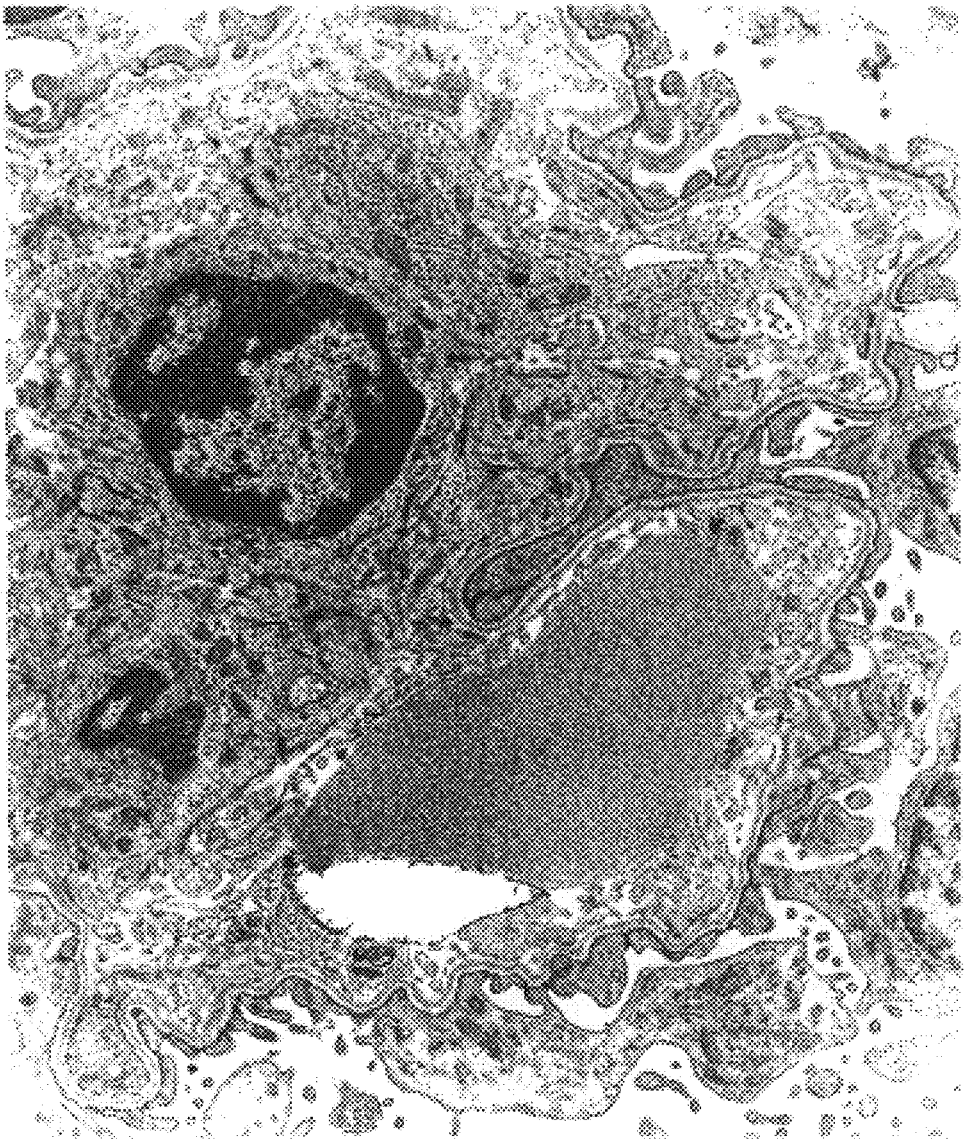
FIG. 10 is a transmission electron micrograph of the GBM of a 7 week old Alport animal injected with a neutralizing antibody specific for α1 integrin. Note the regular trilaminar appearance of the GBM and the absence of focally thickened regions. Magnification is 10,500×.

An antibody that neutralizes α1β1 integrin function as is provided in the examples and in FIG. 10. As an example to illustrate that a soluble agent capable of blocking the interaction of α1β1 integrin with its ligand would produce the same effects on renal disease pathogenesis as the α1 gene knockout mutation, the antibody described in Fabbri et al., *Tissue Antigens,* 48:47–51, 1996 was obtained. This antibody was injected (400 ng/injection, three times weekly, intraperitonealy), and shown to inhibit glomerular basement damage in the Alport mouse model, in much the same manner as was observed in the double mutant.

In another aspect, the invention relates to the use of agents that decrease the level of TGF-β1 as a method for slowing the accumulation of matrix in the progression of glomerular disease, particularly progressive glomerulonephritis. Thus, such agents can be used to treat Alport syndrome patients and patients with insulin dependent diabetes mellitus, as well as others suffering from particularly progressive glomerulonephritis, or any such disorder characterized by expansion of the mesangial matris, proliferation of the mesangial cells, deposition of matrix in the glomerular basement membrane resulting in thickening, thinning, splitting, or some such irregularity, effacement of the podocytes foot processes, or some combination of the above listed manifestations, all of which culminate in the common pathway of renal fibrosis (the prevention for which the combination therapy of α1β1 integrin inhibitors and TGF-β1 inhibitors is particularly effective). To this end, antisense therapies, as described in the art, can be used to block expression of TGF-β1 or α1β1 integrin receptor protein. A variety of agents, synthetic or natural, can be used.

An agent that neutralizes the ability of TGF-β1 cytokine to interact with its receptor can be used in the methods of the present invention. Examples of such agents include, but are not limited to, a neutralizing antibody, a calcineurin inhibitor (i.e., microlide) such as those disclosed in U.S. Pat. No. 5,260,301 (Nakanishi et al.) (e.g., FK506 or tacrolimus and structurally related compounds), a soluble receptor such as the soluble recombinant TGF-β1 receptor disclosed in International Publication WO 98/48024 (Biogen Inc.) (e.g., a soluble chimeric TGF-βRII/IgG1 fusion protein), a peptide fragment of the receptor, or some such fragment that has the ability to irreversibly (or stably) bind with the cytokine and inhibit its ability to bind with its receptor. In addition, an agent that inhibits the ability of TGF-β1 to transduce signals to the nucleus can be used. Effectiveness of such treatments can be determined by evaluating the downstream effects on gene expression of, for example, fibronectin, laminin chains, etc., by the morphometric changes in the glomerular basement membranes, and/or by improvement in the glomerular seive as evidenced by a decrease in the rate of onset and progression of proteinuria.

In one example, FK506 or cyclosporin A can be used to inhibit the calcineurin portion of the TGF-β1 receptor, inhibiting signal transduction through the receptor complex, as has been disclosed for some other kidney diseases (Wang et al., *Cell* 86:435–444, 1996 and Miller et al., *Endocrinol,* 3:1926–1934, 1989), and thereby inhibiting (through an unknown mechanism) the onset of proteinuria, as has been described for the same kidney diseases (Callis et al., *Pediatr. Nephrol.,* 6:140–144, 1992). No such recommendations have been made for Alport syndrome, diabetes mellitus or for diseases associated with an increase in extracellular matrix in the kidney glomeruli, prior to the present invention.

In particular, the present invention illustrates the effect of a combination therapy of inhibiting the α1β1 integrin receptor and TGF-β1 having a synergistic effect at preventing both the glomerular disease and the fibrosis associated with Alport syndrome. It would follow that other diseases that involve the expansion of the mesangial matrix, the proliferation of mesangial cells, progressive basement membrane damage as manifest by one or more of GBM thickening, thinning, splitting, effacement of the podocyte foot processes, or any combination of the above will also benefit from this treatment. In addition, we illustrate the effectiveness of the combination treatment in preventing fibrosis of the tubulointerstitium in Alport syndrome. Fibrosis is a common pathway, the mechanism for which is believed to be identical for all renal diseases for which fibrosis becomes involved. The effectiveness of this combination therapy in treating fibrosis, therefore, should be applicable to all forms of renal fibrosis, regardless of the underlying cause that initiated the pathway leading to fibrosis.

The agents used in the methods of the present invention can be administered in combination with a pharmaceutically acceptable carrier. The agents of the present invention are formulated in pharmaceutical compositions (i.e., formulations) and then, in accordance with the method of the invention, administered to a mammal, such as a human patient, in a variety of forms adapted to the chosen route of administration. The formulations typically include those suitable for parental (including subcutaneous, intramuscular, intraperitoneal, and intravenous) administration or other methods that allow for stability of the agents.

Suitable pharmaceutically acceptable carriers can be in the form of liquids, semisolids, finely divided solids, or combinations thereof. Formulations suitable for parenteral administration conveniently comprise a sterile aqueous preparation of the agent, or dispersions of sterile powders comprising the agent, which are preferably isotonic with the blood of the recipient. Isotonic agents that can be included in the liquid preparation include sugars, buffers, and sodium chloride. Solutions of the agent can be prepared in water, optionally mixed with a nontoxic surfactant. Dispersions of the agent can be prepared in water, ethanol, a polyol (such as glycerol, propylene glycol, liquid polyethylene glycols, and the like), vegetable oils, glycerol esters, and mixtures thereof. The ultimate dosage form is sterile and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the agents over a prolonged period can be achieved by including agents for delaying, for example, aluminum monostearate and gelatin.

In addition to the aforementioned ingredients, the formulations of this invention may further include one or more accessory ingredients including diluents, buffers, binders, disintegrants, surface active agents, thickeners, lubricants, preservatives (including antioxidants) and the like. The formulations may be conveniently presented in unit dosage form and may be prepared by any of the methods well known in the art of pharmacy.

Useful dosages (i.e., effective amounts that provide a desired effect) of the agents described herein can be determined by comparing their in vitro activity and the in vivo activity in animal models. Methods for extrapolation of effective dosages in mice, and other animals, to humans are known in the art. For example, doses of about 150 mg per kg to about 300 mg per kg twice daily of agent for intravenous injection. Suitable doses to be administered are, in general, those which are sufficient to produce a desired effect, such as by inducing a demonstrable increase of phase II enzyme expression, or other characteristic described herein.

EXAMPLES

In the examples a description of two different animal models is provided. The first is an "Alport" mouse model which does not express collagen α3(IV) and is normal for α1 integrin and is described in Cosgrove et al., *Genes Dev.*, 10:2981–2992, 1996, and the second, which is referred to as the "double knockout" mouse, which was derived by crossing the Alport mouse with a mouse that was null for the α1 integrin gene. There are differences between the Alport mouse and the double knockout that serve to illustrate the efficacy of blocking α1β1 integrin function on slowing glomerular disease. These effects are described in detail.

The Alport mouse is in a 129 Sv/J pure genetic background, and the double knockout mouse is in a 97.5% pure 129 Sv background. An exception for this are the animals that were used to generate FIGS. 4, 5, and 6. These experiments were performed early in the history of the Alport mouse model, and thus were generated by crossing the chimeric males with C57 B1/6 females, and then crossing the resulting heterozygotes to generate homozygote Alport mice that would be the F2 generation. This is the same generation of animals used in the original description of the Alport mouse model (Cosgrove et al., *Genes Devel.,* 10:2981–2992, 1996). This is customary for early gene knockout studies, since it speeds identification of the knockout phenotype. The results obtained from these F2's, with respect to specific mRNA induction, are consistent with results obtained for the pure 129 Sv/J knockout. It should be noted that all of the experiments that provide comparative analysis of Alport mice versus double knockout mice were performed on the inbred strains.

The role of TGF-β1 on renal disease progression, as well as on the development of fibrosis in both animal models was examined. This was done by examining two different inhibitors of TGF-β1 that work in very different ways. Using two different inhibitors (FK506 and a soluble TGF-β1 receptor) provides proof that the effect is due to TGF-β1 inhibition rather than a side effect of the agent used. FK506 may be therapeutic in treating progressive fibrosis related to overexpression of TGF-β1.

In the course of analyzing the different animal models and drug treatments described, there is a specific course of evaluation that has remained constant throughout. Three different areas were evaluated. First, renal function was examined, which provides an assessment of overall integrity of the glomerular filter. This was done by examining the urinary output of serum albumin. Second, the structural integrity of the tissue at both light and electron microscopic levels was examined. Both transmission and scanning electron microscopic procedures were used. These procedures were designed to determine the degree of renal histopathology under these different conditions. Finally, molecular analysis experiments were performed to examine what changes take place in specific genes and there corresponding proteins as a result of these different conditions. These were examined by looking at the specific RNAs using northern blots, in situ hybridization, and RNase protection, and by using immunohistochemical detection for specific proteins. As the specific procedures are repeated for the analysis of different animal models and different drug treatments in different animal models, for the sake of avoiding redundancy it is now stated that the procedures were performed identically (as nearly as can be expected in day to day practice) in all cases, and are thus described once and then referred to in latter specific examples.

There are a variety of alternative techniques and procedures available to those of skill in the art, which would similarly permit one to successfully perform the intended invention. All reagents were obtained from Sigma Chemical Co., St. Louis, Mo., unless otherwise specified. PBS used in all of the studies described herein was purchased in tablet form, each tablet reconstituted in 200 ml of water to make pH 7.4 PBS, from Sigma Chemical Co, St. Louis Mo., Product number P-4417.

Methods

I. Renal Function

A. Protein Analysis: Initial measurements of urinary protein were carried out using Albustix (Miles Laboratories, Elkhart, Ind.), and reading the relative amounts from the color chart provided with the kit..

Urine samples were collected at weekly intervals and 0.5 μl fractionated by electrophoresis through 10% denaturing acrylamide gels. The protein in the gels was stained with coomassie blue and photographed. Bovine serum albumin was used as a molecular weight standard.

II. Structural Integrity

A. Transmission Electron Microscopy: Fresh external renal cortex was minced in 4% paraformaldehyde, allowed to fix for 2 hours, and stored at 5° C. in PBS (pH 7.4). The tissue was washed extensively (5 times for 10 minutes each at 4° C.) with 0.1M Sorenson's buffer (Sorenson's buffer was made by combining 100 ml of 200 mM monobasic sodium phosphate and 400 ml of 200 mM dibasic sodium phosphate with 500 ml of water, and adjusted to pH 7.4), and postfixed in 1% osmium tetroxide in Sorenson's buffer for 1 hour. The tissue was then dehydrated in graded ethanol (70%, then 80%, then 90%, then 100% for ten minutes each), and finally in propylene oxide and embedded in Poly/Bed 812 epoxy resin (Polysciences, Inc., Warrington, Pa.) following the procedures described by the manufacturer. In short, 42 ml of polybed 812 was mixed with 26 ml of dodecylsuccinic anhydride (DDSA, Polysciences, Inc.) and 24 ml of nadic methyl anhydride (Polysciences Inc.). One and a half mls of 2,4,6 tri(dimethly aminomethyl) phenol was added as a catalyst, and the activated resin frozen in 10 ml aliquots until needed for embedding specimen. Glomeruli were identified in 1 μm (micron) sections stained with toluidine blue, and thin sections were cut at 70 nm (nanometer) thickness using a Reichert Jung Ultracut E ultramicrotome (Cambridge Instrument Co, Vienna, Austria). Sections were mounted onto grids and stained with uranyl acetate and lead citrate using well known procedures. Grid-mounted sections were examined and photographed using a Phillips CM10 electron microscope.

B. Scanning Electron Microscopy: Small pieces (approximately 2 mm cubes) of kidney cortex were fixed in 3% phosphate buffered glutaraldehyde, then postfixed in 1% phosphate buffered osmium tetroxide. Samples were then dehydrated in graded ethanols, and critical point dried in carbon dioxide. The cubes were then cracked in pieces by stressing them with the edge of a razor blade, and mounted with glue onto stubs with the cracked surface facing upward. The surface was sputter coated with gold/palladium using well known procedures and visualized with a scanning electron microscope.

C. Jones Silver Methenamine Stain: Jones stain was performed on paraffin embedded kidneys using the method described by Burns and Bretschschneider, *Thin is in: plastic embedding of tissue for light microscopy*, Educational Products Division, American Society of Clinical Pathologists, Chicago, Ill., pp. 24–25, 1981.

III. Molecular Analysis

A. Northern Blot Analysis: Kidneys were removed and snap frozen in liquid nitrogen and ground to a powder in liquid nitrogen using a mortar and pestle. The powder was solubilized in TRIZOL reagent (GibCo/BRL, Grand Island, N.Y.) using 5 ml of reagent per kidney. Total cellular RNA was extracted according to the manufacturer's instructions. Twenty micrograms (20 μg) of RNA was fractionated on a 1.0% agarose/formaldehyde/MOPS (3-(N-morpholino) propanesulfonic acid) gel by electrophoresis at 80V for 4 hours. Gels were soaked in water for 45 minutes, and transferred to Hybond N (uncharged nylon, New England Nuclear, Inc., Boston, Mass.) by capillary blot overnight using 750 mM ammonium acetate (in water) as a transfer buffer. The RNA was UV crosslinked to the blot using a Stratalinker (Stratagene, Inc., LaJolla, Calif.). Blots were prehybridized in a solution comprised of 50% formamide, 10X Denhardt's solution, 1M NaCl, 50 mM Tris-HCl, pH 7.4, 1% SDS, and 200 μg/ml sonicated and denatured salmon sperm DNA (Sigma Chemical Co., St. Louis, Mo.). Probes ($^{32}$P-labeled cDNA probe fragments) were labeled by random priming to a concentration of $10^9$ cpm/μg using a random priming DNA labeling kit (Boeringer Mannheim, Indianapolis, Ind.). Prehybridization and hybridization buffers consisted of 5X saline-sodium citrate buffer (SSC), 5X Denhardt's solution, 0.5% sodium dodecyl sulfate (SDS), and 200 μg/ml sonicated and denatured salmon sperm DNA. Filters were prehybridized for at least 5 hours and then hybridized overnight using 1 million DPM (disintigrations per minute) of probe per ml of hybridization solution. The filters were then washed at high stringency (two times for 30 minutes each at 65° C. in a solution comprised of 300 mM NaCl, 30 mM sodium citrate, and 0.2% sodium dodecyl sulfate in water) and exposed to X-ray film. The quality of the RNA preparations and the consistency of loading was assessed by staining gels with ethidium bromide and scanning the 18S and 28S ribosomal RNA bands using a Gel Imager 2000 digital imaging system instrument and software package (Applied Imaging, Santa Clara, Calif.). Appropriate ratios of ribosomal bands confirmed that the RNA preparations were of high and consistent quality. Quantitative densitometric scanning confirmed no more than a 10% variance in sample loading. These tools were used rather than a control probe because of concerns that changes in cell physiology concomitant with progressive fibrosis makes such control probes unreliable. Quantitative differences in expression were assessed by phosphorimage analysis using a BioRad GS-525 phosphorimager (Bio Rad, Inc., Hercules, Calif.), and subtracted for background hybridization.

Probes were isolated from a murine kidney 5' stretch cDNA library (Clonetech) by PCR amplification using published sequence for the different basement membrane collagen cDNAs and those for the associated proteins. For the basement membrane collagen probes, sequence encoding the conserved NCl domain was amplified. The primers and conditions used were identical to those employed by Miner and Sanes, *J. Cell Biol.*, 127:879–891, 1994. For collagen COL4A1, the primers were (Muthukumaran et al., *J. Biol. Chem.*, 264:6310–6317, 1989): sense, 5'TCTGTGGAC-CATGGCTTC3' (SEQ ID NO:1); antisense, 5'TTCTCATG-CACACTTGGC3' (SEQ ID NO:2). For collagen COL4A2, the primers were (Saus et al., *J. Biol. Chem.*, 264:6318–6324, 1989): sense, 5'GGCTACCTCCTGGT-GAAG3' (SEQ ID NO:3); antisense, 5'TTCATGCACACT-TGGCAG3' (SEQ ID NO:4). Both COL4A1 and COL4A2 were amplified under the same conditions. Virions (a×10$^6$) were subjected to 35 cycles of PCR using a hot start (10 minutes at 95° C.), then 95° C. for 30 seconds, 55° C. for 30 seconds, and 72° C. for one minute. Probes were subcloned and verified by DNA sequence analysis.

Probes for the basement membrane associated proteins were amplified from the same library as the basement membrane collagens. Primers were taken from the 3' sequence. For the HSPG core protein, the primers were (Noonan et al., *J. Biol. Chem.*, 263:16379–16387, 1988): sense, 5'CGGGCCACATTCTCC3' (SEQ ID NO:5); antisense, 5'GGAGTGGCCGTTGCATT3' (SEQ ID NO:6). For laminin B2, the primers were (Sasaki and Yamada, *J. Biol. Chem.*, 262:17111–17117, 1987): sense 5'ACCAG-TACCAAGGCGGA3' (SEQ ID NO:7); antisense, 5'TCAT-TGAGCTTGTTCAGG3' (SEQ ID NO:8). For laminin B1, the primers were (Sasaki et al., *Proc. Natl. Acad. Sci. USA*, 84:935–939, 1987): sense 5'TAGAGGTTATTTTGCAG-CAGA3' (SEQ ID NO:9); antisense 5'TTGGATATCCT-CATCAGCTTG3' (SEQ ID NO:10). For entactin, the primers were (Mann et al., *EMBO Journal*, 8:65–72, 1989): sense 5'GTGGTTTACTGGACAGACATC3' (SEQ ID NO:11), antisense, 5'CCAATCTGTCCAATAAAGG3' (SEQ ID NO:12). For laminin A chain, the primers were (Duetzmann et al., *Eur. J. Biochem.*, 177:35–45, 1988): sense 5'ACA-CACTCCAAGCCCACAAAAGCAAG3' (SEQ ID NO:13); antisense 5'GAGGGAAGACTCCTTGTAGGTCAA3' (SEQ ID NO:14). For S-laminin, the primers were (Hunter et al., *Nature*, 338:229–234, 1989): sense, 5'GCA-GAGCGGGCACGGAGC3' (SEQ ID NO:15), antisense 5'TGTACCTGCCATCCTCTCCTG3' (SEQ ID NO:16). PCR conditions were identical to those used for the type IV collagen chains above.

The probes for MMP-2, Timp2, and Timp3 were isolated using total RNA from day 13 mouse embryos by RT-PCR. The primer set for MMP-2 amplifies a 237 bp fragment from the mRNA (Reponen et al., *J. Biol. Chem.*, 267:7856–7862, 1992), and included upstream primer 5'CCC CTA TCT ACA CCT ACA CCA3' (SEQ ID NO:17) and downstream primer 5'TGT CAC TGT CCG CCA AAT AAA3' (SEQ ID NO:18). The primer set for Timp-2 amplifies a 195 bp fragment of the mRNA (Shimizu et al., *Gene*, 114:291–292, 1992), and included upstream primer 5'CAG AAG AAG AGC CTG AAC CAC A3' (SEQ ID NO:19) and downstream primer 5'GTA CCA CGC GCA AGA ACC3' (SEQ ID NO:20). The primer set for Timp-3 amplifies a 337 bp fragment from the mRNA (Apte et al., *Developmental Dynamics*, 200:177–197, 1994), and included upstream primer 5'GGT CTA CAC TAT TAA GCA GAT GAA G3' (SEQ ID NO:21) and downstream primer 5'AAA ATT GGA GAG CAT GTC GGT (SEQ ID NO:22). For all three probes, one microgram of total RNA was reverse transcribed using GibCo Superscript plus reverse transcriptase and the downstream primer, according to the protocols described by the manufacturer. One tenth of the reaction was subjected to 40 cycles of hot-start PCR using PFU polymerase (Stratagene, Inc.).

TGF-β1 probe was a gift from H. L. Moses (Miller et al., *Mol. Endocrinol.*, 3:1926–1934, 1989), except for RNAse protection which required a human probe. For this probe, a 24 base pair fragment of TGF-β1 was amplified by PCR from a human kidney cDNA library (Clonetech, Palo Alto, Calif.). The primer sets used were GCA GAA GTT GGC ATG GTA G (SEQ ID NO:23) (lower) and GGA CAT CAA CGG GTT CAC TA (SEQ ID NO:24) (upper). The fragment was reamplified with PFU polymerase (Stratagene) and blunt-end ligated into the pBluescript SK+ plasmid.

B. In situ hybridization: Kidneys were initially fixed by slow transcardiac perfusion (using 4% paraformaldehyde in PBS). The animals were first deeply anaesthetized using Avertin (2,2,2-tribromoethanol, Aldrich Chemical Co., Milwalkee, Wis.). The chest cavity was opened, and a small hole was made in the right ventricle by puncturing with a tuburculin needle to allow exit of the perfusate. A second tuberculin needle connected to a 30-ml syringe containing perfusion buffer was inserted into the apex of the left ventricle. One milliliter of fixative was perfused per gram body weight at a rate of about 3 milliliters per minute. Properly fixed kidneys were firm and had a marbled appearance. Following perfusion, the renal capsule was removed with iris forceps, kidneys were cut in half longitudinally (bisecting the pelvis, medulla and cortex), and placed in fixative at 4° C. for an additional hour. The fixed halves were embedded in paraffin, cut at 6 µm, and transferred onto SUPERFROST PLUS microscope slides (Fisher Scientific, Inc., Pittsburg, Pa.). Slides were baked on a slide warmer at 60° C. for 20 minutes, and stored at 4° C. until used (slides are useful for up to six weeks). Kidneys from control and Alport littermates were embedded side by side to control for subtle differences that might be incurred during the hybridization procedure.

Slides were baked in a vacuum oven at 60° C. for 1 hour, then dewaxed by 3 successive 2-minute washes in xylenes. The tissue was dehydrated in ethanol, deproteinated by incubating in 0.2N HCl for 15 minutes, washed with PBS and digested with 3 µg/ml proteinase K (Boehringer Mannheim, Indianapolis, Ind.) for 10 minutes at 37° C. The digestion was stopped by washing in 2 mg/ml glycine in PBS. Following dehydration of the tissue in graded ethanol solutions (70%, 80%, 90%, 100% for 10 minutes each at room temperature), the tissue was prehybridized, hybridized, and washed according to the protocols described with the Genius in situ Hybridization Kit (Boehringer Mannheim, Indianapolis, Ind.) with the following modifications. In both prehybridization and hybridization solutions, 10 mg/ml phenol/chloroform-extracted bakers yeast tRNA was included. This step significantly reduced non-specific signal. Following the hybridization, the tissue was washed twice in 2X SSC at 50° C., then digested with RNase A for 6 minutes at room temperature. The amount of RNase A was determined for each probe (range from 200 ng/ml to 5 µg/ml). Negative control probes include the coding sequence for bacterial β-galactosidase or neomycin phosphotransferase. All probes were approximately 200 bases in length, cloned into the SacI site of BlueScript SK+ (Stratagene, Inc., LaJolla, Calif.), and transcribed (after linearization) from the T3 side. The only exception was TGF-β1, which was 974 bases and cloned into a pmT vector.

C. RNase Protection Assay: Experiments were carried out using a RPAII kit (Ambion, Inc., Austin, Tex.) following the protocols provided with the kit. For a probe, a 264 base pair fragment of TGF-β1 was amplified by PCR from a human kidney cDNA library (Clonetech, Palo Alto, Calif.). The primer sets used were GCA GAA GTT GGC ATG GTA G (SEQ ID NO:25) (lower) and GGA CAT CAA CGG GTT CAC TA (SEQ ID NO:26) (upper). The fragment was reamplified with PFU polymerase (Stratagene) and blunt-end ligated into the pBluescript SK+ plasmid (Stratagene). The antisense probe was generated from the T7 promoter.

D. Immunofluorescence Analysis: Fresh kidney was removed, cut into 3-mm thick cross sections, embedded in Tissue Tek OCT aqueous compound (product number 4583, Miles Laboratories, Elkhart, Ind.), and frozen by placing in a −150° C. freezer. Sections were cut at 3 microns using a Microm type HM505N (Zeiss, Inc., Walldorf, Germany) cryostat, and thawed onto poly-L-lysine-coated slides. Slides were fixed for 15 minutes by soaking either in cold (−20° C.) 95% ethanol, if to be used for staining with the basement membrane collagen-specific antibodies, or with cold (20° C.) acetone for staining with antibodies specific for the basement membrane associated proteins. Slides were allowed to air dry overnight, and stored desiccated at −80° C. until used.

Samples were allowed to reach ambient temperature, then washed three times in PBS (pH 7.4) at room temperature. For staining with the antibodies against the type IV collagens, the tissue was pretreated with 0.1M glycine and 6M urea (pH 3.5) to denature the protein and expose the antigenic sites. The appropriate dilutions (determined empirically) of the primary antibodies were applied to the sample and allowed to react for 3 hours at 5° C. in a humidified box. Antibodies were diluted into a solution of 5% nonfat dry milk in PBS (pH 7.4). The use of nonfat dry milk substantially reduced background fluorescence. Samples were washed four times in PBS (pH 7.4) for 10 minutes each at room temperature to remove the primary antibody, and then reacted with the appropriate FITC-conjugated secondary reagent. All secondary reagents were used at a 1:100 dilution, using 7% nonfat dry milk in PBS as the diluent. Secondary reagents were allowed to react for 2 hours at 4° C. The slides were then washed four times with cold PBS (pH 7.4) followed by the application of anti-fade mounting media (Vector Laboratories, Inc., Burlingame, Calif.). Samples were sealed under glass cover slips using clear nail polish. Slides were photographed at 1000× magnification. Jones silver methenamine staining was performed on plastic embedded specimen.

Goat antisera against the COL4A1 and COL4A2 chains was purchased from Southern Biotechnology, Inc., Birmingham, Ala. This antibody was tested for cross reactivity by the manufacturer, and produced a staining pattern in the glomerulus that is consistent with that observed for other antibody preparations against these chains (Miner and Sanes, *J. Cell. Biol.*, 127:879–891, 1994). Anti-heparin sulfate proteoglycan (HSPG) antibody is a rat monoclonal raised against the HSPG core protein purified from EHS mouse tumor. The antibody was tested for cross-reactivity with laminin, collagen type IV, fibronectin, and entactin by western blot and dot blot immunoassay by the manufacturer (Chemicon International, Temecula, Calif.) and as described elsewhere (Horiguchi et al., *J. Histochem. Cytochem.*, 37:961–970, 1989). Anti-laminin-1 antibodies are a rabbit antisera. The immunogen was purified from EHS basement membrane and purchased from Sigma Immunochemicals (St. Louis, Mo.). Dot blot immunoassay, performed by the manufacturer (Sigma), confirmed the absence of cross-reactivity to collagen IV, fibronectin, vitronectin, and chondroitin sulfate types A, B, and C. Anti-fibronectin is a rabbit antisera raised against fibronectin purified from human plasma. It was tested by the manufacturer (Sigma Immunochemicals) against cross-reactivity to collagen IV, laminin, vitronectin, and chondroitin sulfate A, B, and C using dot blot immunoassay. Anti-entactin is a rat monoclonal antibody produced using EHS-derived entactin as immunogen. This reagent was purchased from Upstate Biotechnology Incorporated, Lake Placid, N.Y., and was tested for appropriate immunoreactivity as well as for the absence of cross-reactivity with other major basement membrane components by western blot analysis (Ljubimov et al., *Exp. Cell Res.*, 165:530–540, 1986).

Immunofluorescence and Jones stained images were recorded and processed using an Olympus BH2 RFLA fluorescence microscope interfaced with an Applied Imaging Cytovision Ultra image analysis system (Applied Imaging Inc.). Images were captured using a high resolution black and white video camera. These images were modified using the system software. In processing the images, care was taken to closely approximate the fluorescence observed directly on the microscope.

E. Immunoperoxidase Detection: The immunoperoxidase detection method was used in immunostaining for TGF-$\beta$1 in glomeruli as well as fibronectin and collagen type I in tubunointerstitium. The collagen type I antibody is rabbit anti-mouse, and was purchased from Biogenesis, Inc. (Sandown, N.H.). The antisera was used at a 1:100 dilution for immunoperoxidase staining. The fibronectin antibody used was the same as for immunfluorescence staining (a rabbit anti-human fibronectin antisera from Sigma Chemical Company, St. Louis, Mo.), and was used at a 1:100 dilution. Secondary reagents were biotinylated anti-rabbit antibodies purchased from Vector laboratories (Burlingame, Calif.) and used at a dilution of 1:100. The tissue was embedded in paraffin (using the same procedure as described for in situ hybridization) and sectioned at 3 microns. Deparrifinized sections were pretreated with 5 $\mu$g of proteinase K (Boehringer Mannheim, Indianapolis, Ind.) in 100 mM Tris-HCl (pH 7.4) to expose epitopes. The proteinase digestion was stopped by incubating in 2 mg/ml glycine in PBS for 30 seconds. Dewaxed proteinase K-treated tissue was washed three times with PBS and reacted with the primary antibody for 1 hour at room temperature, washed 3 times with PBS then reacted with a biotinylated secondary antibody for 1 hour at room temperature. After washing three times with PBS (pH 7.4), slides were incubated with streptavidin horse radish peroxidase (3 $\mu$g/ml, Vector Laboratories) for 30 minutes at room temperature. Following three washes with PBS, antibody binding was developed with the AEC substrate system (Vector AEC SK-4200, Vector Laboratories) following the procedures described by the manufacturer For TGF-$\beta$1, the primary antibody was chicken $\alpha$-human TGF-$\beta$1 (R&D Systems, Minneapolis, Minn.) used at a 1:15 dilution in 7% non-fat dry milk in PBS (which was used as diluent for all antibodies). This was allowed to react for at least 3 hours at room temperature. The secondary antibody was a biotinylated goat anti-chicken for TGF-$\beta$1 (Vector Laboratories Burlingame, Calif.) was applied at a 1:100 dilution and allowed to react for at least 1 hour. Following three washes, Immunoperoxidase detection was performed using an AEC kit (Vector Laboratories, Burlingame, Calif.).

Example 1

Production of an Alport/$\alpha$1 Integrin Double Mutant

A mouse model for the autosomal form of Alport syndrome was created by targeted mutagenesis of the COL4A3 procollagen gene as described previously (Cosgrove et al., *Genes Dev.*, 10:2981–2992, 1996). This is referred to herein as the "Alport mouse" and is available from Jackson Laboratories at Bar Harbor, Me. under Accession No. 2908. This $\alpha$3(IV) knockout mouse, which is in a 129 Sv/J background, was crossed (five successive backcrosses with pure 129 Sv, then with the integrin $\alpha$1 null mouse, which is pure 129 Sv), to produce a "double knockout" mouse, which is over 97.5% pure 129 Sv. The $\alpha$1 knockout mouse was provided by Humphrey Gardner of the Scripps Institute in LaJolla, Calif. and is described in Gardner et al., *Dev. Biol.*, 175:301–313, 1996.

Example 2

Assessment of Alport Renal Disease Progression in Mouse Models

The mice studied in this example included Alport mice, which do not express collagen $\alpha$3(IV) and are normal for $\alpha$1 integrin (available from Jackson Laboratories of Bar Harbor, Me.), and double knockouts (i.e., double mutants), which do not express collagen $\alpha$3(IV) or integrin $\alpha$1. The double mutants were 97.5% 129 Sv and 2.5% Sv/J backgrounds.

Urine was collected from the mice at weekly intervals and protein analysis was carried out as described in the Methods Section. As shown in FIG. 1, for animals that did not express collagen $\alpha$3(IV) and were normal for $\alpha$1 integrin, the mean age for Alport renal disease onset (based on a study of 6 individuals), as measured by the onset of proteinuria, was 3.5 weeks to 4 weeks. Proteinuria progressed rapidly, reaching peak levels at between 6 weeks and 6.5 weeks of age. The mean age of death due to renal failure was between 8 weeks and 9 weeks of age. No animal of this genotype (9 were tested) lived beyond 9 weeks of age. Blood urea nitrogen levels (BUN) became elevated at 7 weeks to 7.5 weeks of age. In the double mutants (four were tested for these measurements), onset of proteinuria was between 5 weeks and 5.5 weeks of age, and progressed more slowly, reaching peak levels at 9 weeks to 9.5 weeks. The mean age of death due to renal failure was between 15 weeks and 16.5 weeks. Animals developed elevated BUN at between 10 weeks and 11 weeks of age.

Example 3

Characterization of Double Knockout Mouse Model

Three different sets of animals (normal controls, animals not expressing the $\alpha$3(IV) gene and normal for $\alpha$1 integrin (Alport mice), and double mutants) were analyzed at 4 and 7 weeks of age using a number of different techniques.

Transmission electron microscopy was performed to assess basement membrane integrity. At 4 weeks of age (data not shown), the Alport littermates showed rarefied basement membranes in 100% of the glomerular capillary loops. The double mutants showed some glomerular basement membrane (GBM) rarefication (i.e., irregular thickening, thinning, and splitting), however it was infrequent and rarely extensive. About 20% of the glomeruli in the double mutants showed no apparent basement membrane rarefication at all. About 5% of the glomeruli in the Alport mice at this time point were fibrotic, while there were no fibrotic glomeruli found in the double mutant littermates. FIG. 2 illustrates the degree of glomerular basement membrane damage characteristic of these different mice by seven weeks of age. A typical glomerular capillary loop is illustrated. The glomerular basement membrane in the Alport mice at this developmental timepoint is badly damaged in virtually all glomeruli. Evident in FIG. 2B is gross irregular thickening and thinning, and extensive effacement of the podocyte foot processes. In the double knockout, however (FIG. 2C) the GBM is, for the most part, ultrastructurally normal, with the exception of a few small irregularities, and the foot processes of the podocytes maintain a normal architecture (compare regions denoted by arrows for the normal mouse in FIG. 2A with the double knockout mouse in FIG. 2C). At this timepoint between 30% and 50% of the glomeruli in the Alport mouse were fibrotic, while less than 5% were fibrotic in the double mutants.

Scanning electron microscopy of the 7-week old mice (data not shown) indicated that the Alport mice showed significant swelling of the foot processes of the podocytes, destroying the normally elegant and complex structure of these cells. This foot process effacement has been described for Alport glomerulonephritis. In the double mutants, while the architecture was not perfect, it was very close to that observed in glomeruli from control mice. The swelling of these foot processes is responsible for blocking the glomerular filter and leads to uremia. Therefore this finding is significant with regard to the improved glomerular function in the double mutant relative to the Alport littermates.

Paraffin embedded mounts of whole kidneys from the 7-week old mice were stained using Jones' Method and the total number of fibrotic glomeruli counted (data not shown). Virtually all of the glomeruli from the Alport mice were affected to some degree. Most showed glomerular hypercellularity and expansion of the mesangial matrix, and about a third were fibrotic. In contrast, the glomeruli from the double mutant mice were largely normal with respect to mesangial matrix and cellularity. About 25% did show evidence of mesangial cell proliferation, and 5% were fibrotic. The analyses were repeated on two different sets of mice with very similar results.

Immunofluorescence analysis was performed using frozen renal cortex taken from these same animals. The tissue was reacted with antibodies specific for proteins known to accumulate in the GBM as a function of Alport renal disease progression. These included laminin-1 (Lam-1) (used at a 1:200 dilution), collagen $\alpha 1(IV)$ and $\alpha 2(IV)$ chains (COL 4A1,2) (used at a 1:15 dilution), fibronectin (Fib) (used at a 1:200 dilution), heparin sulfate proteoglycan (HSP) (used at a 1:100 dilution), and entactin (ent) (used at a 1:200 dilution). All antibodies were diluted into 7% nonfat dry milk in PBS. The results are shown in FIG. 3. At seven weeks of age, all of these components were significantly elevated in the GBM of the Alport mice relative to controls. In the fibrotic glomeruli, all of these components were abundant. In the double mutant, immunostaining for collagen $\alpha 1(IV)$ and $\alpha 2(IV)$ chains was comparable to that for the Alport mouse in non-fibrotic glomeruli. This is expected, since the type IV collagen composition of the GBM in the double mutant is the same as that in the Alport mouse (i.e., comprised entirely of collagen $\alpha 1(IV)$ and $\alpha 2(IV)$ chains). Staining for laminin-1 and heparin sulfate proteoglycan were significantly reduced in the GBM of the double mutants relative to Alport mice (compare FIG. 3F with 3E, and FIG. 3L with FIG. 3K, respectively), and there was no apparent staining for fibronectin in the GBM of the double mutants (FIG. 3I), which is abundant in the GBM of the Alport mice (FIG. 3H). Immunostaining in the mesangial matrix for these proteins was comparable between double mutant and Alport mice, however, for heparin sulfate proteoglycan, mesangial staining was reduced in the double mutants (FIG. 3L) relative to either normal controls (FIG. 3J) or Alport mice (FIG. 3K).

Northern blot analysis was performed using RNA isolated from total renal cortex from normal, Alport, and double mutant mice at 7 weeks of age. Twenty micrograms of each RNA sample was fractionated on an agarose gel, transferred to nylon by capillary blot, and hybridized to a radiolabeled probe corresponding to a portion of the mouse TGF-$\beta 1$ cDNA. Following a series of high stringency washes, the membrane was exposed to X-ray film. FIG. 9 shows that, while TGF-$\beta 1$ is induced in the Alport mouse (Fourth lane from the left compared with second lane from the left, which is a control), it is not induced in Alport mice that harbor the $\alpha 1$ integrin mutation (double knockouts) (third lane from the left compared with second lane from the left, which is a control). It is this data that led the investigators to speculate whether the effect of $\alpha 1$ inhibitors might be mediated by the suppression of TGF-$\beta 1$. Thus the TGF-$\beta 1$ inhibitor experiments that follow were carried out to clarify this issue.

Example 4

Role of TGF-$\beta 1$ in Post-Proteinuric Alport Renal Disease Progression

Tissues were harvested from F-2 backcrosses of 129 Sv/J founder animals onto the C57 B1/6 background (see above). Experiments were performed at least twice (on specimen from two different sets of animals). Results for data presented herein were clear and consistent.

These experiments were performed to illustrate two points. First, is there a temporal correlation between induction of TGF-$\beta 1$ mRNA and the mRNAs encoding matrix proteins that accumulate as a function of Alport renal disease progression, and second, are these mRNAs actually induced in the glomeruli? (Since only 5% of the wet weight of the kidney is glomeruli, induction of specific mRNAs in total renal cortex relates more to the issue of progressive fibrosis that glomerulonephritis.)

Total RNA was isolated from kidneys of Alport animals and control littermates at two week intervals starting at 6 weeks and ending at 12 weeks of age. Proteinuria in the F2 mice used in this study begins when the mice are approximately 5.5 to 6 weeks of age (data not shown). The RNA was fractionated on denaturing agarose gels, transferred to nylon supports, and probed with radiolabeled probes specific for either the $\alpha 1(IV)$ or $\alpha 2(IV)$ collagen chains, entactin, the laminin $\beta 1$ or $\beta 2$ chain, fibronectin, or TGF-$\beta 1$. The results in FIG. 4 illustrate that the mRNAs for all of these proteins with the exception of laminin $\beta 1$ are induced following the onset of proteinuria in the Alport mouse model.

Northern blots for this same timecourse were also performed for laminin $\alpha 1$, laminin $\beta 2$, laminin $\gamma 1$, heparin sulfate proteoglycan core protein, and the collagen $\alpha 4(IV)$, and $\alpha 5(IV)$ chains (data not shown). No significant differences in mRNA levels for these other basement membrane proteins were apparent when comparing the control to the mutant.

The results of the northern analyses were analyzed using a phosphorimager to directly quantify the relative changes in specific mRNA expression during the timecourse. FIG. 5 illustrates that induction of the specific mRNA levels is first apparent at six weeks of age, or about the time when protein in the urinary space reaches the maximum levels in the F2 mice (Cosgrove et al., Genes Dev., 10:2981–2992, 1996). By 8 weeks, mRNA levels peak, with the mRNAs encoding TGF-$\beta 1$ and fibronectin induced 6.6- and 9.4-fold over that of control mice, respectively. The mRNA levels for collagen $\alpha 1(IV)$, $\alpha 2(IV)$, and entactin were all about 3-fold induced by week 8. In contrast, no significant changes in mRNAs encoding the laminin $\beta 1$ and $\beta 2$ chains, as determined by these same total RNA northern blots, were observed at any point in renal disease progression.

To examine whether the mRNAs encoding TGF-$\beta 1$, or the different basement membrane components were induced in a particular glomerular cell type, in situ hybridization was performed using digoxygenin-labeled antisense probes specific for the mRNAs. Kidneys were harvested from 10 week old F2 Alport mice and normal control littermates following heart perfusion with 4% paraformaldehyde in PBS, and processed for in situ hybridization analysis as described in the Methods Section. Antisense probes were specific for the NC1 domain of collagen α1(IV), TGF-β1, Fibronectin, entactin, or the laminin β1 chain. A probe specific for bacterial β-galactosidase was used as a control for non-specific binding (a negative control), as this probe did not hybridize to total mouse kidney RNA on northern blots (data not shown). The control probe was hybridized at the same time as each specific probe, and treated with the same concentration of RNase A following the hybridization procedure. RNase A treatment was carried out at 0.25 μg/ml for α1(IV), TGF-β1, and fibronectin, and at 3 μg/ml for entactin and laminin β1. The results are shown in FIG. 6.

The results in FIG. 6 illustrate that, for all specific mRNAs examined, elevated levels are clearly observed in the visceral epithelial cells (podocytes) of the glomerulus in the COL4A3 knockout mice (Alport mice). For the collagen α1(IV) chain, expression of the mRNA in the control is observed in both the mesangial cells and the endothelial cells of the glomerulus (FIG. 6A), which is consistent with where this molecule localizes in the mature animal. In the mutant, expression in the mesangial matrix may be elevated, as evidenced by much darker staining when compared to the mesangial cell staining in the control sample, however the most obvious difference between the control and the mutant is the ring of stained cells lining the outer circumference of the glomerulus, corresponding to the podocytes (FIG. 6B). Fibronectin expression in the control glomerulus is observed primarily in the mesangial cells (FIG. 6D). While staining in the mesangial cells is also observed in the mutant, the podocytes are clearly expressing significant levels of fibronectin mRNA (FIG. 6E). Expression of TGF-β1 is very weak in the glomeruli of the control animals, however, some specific staining is observed in the mesangial cells of the control animals (FIG. 6G). In the mutant, TGF-β1 mRNA levels are significantly elevated in the mesangial cells, the endothelial cells, and again in the podocytes (FIG. 6H). For entactin, the mRNA localized to the podocytes of the control, which is not unexpected since this protein localizes specifically to the GBM. Unexpectedly, some mesangial cell-specific staining is observed in the control animal. While the staining in the visceral epithelial cells in the mutant seems to indicate elevated expression, this is not a quantitative assay, and the difference between the control and the mutant is too small to be definitive (Compare FIGS. 6J with 6K).

Northern blots revealed that mRNA levels for the laminin β1 chain were unchanged in the control versus the mutant throughout the timecourse. In situ hybridization analysis for this same message illustrated the expected mesangial cell-specific localization in glomeruli from control kidneys (FIG. 6M). In the glomeruli from mutant mice, however, the mRNA is clearly induced in the visceral epithelial cells (FIG. 6N).

Tissue samples were harvested at 3 and 5 weeks of age, and analyzed by in situ hybridization using these same probes. The staining pattern in these glomeruli were indistinguishable from those of normal littermates (data not shown). This suggest that activation of these genes in the podocytes occurs after the onset of proteinuria.

TGF-β1 protein data based on immunoperoxidase detection using antibodies specific for the active isoform of the cytokine corroborate data obtained by in situ hybridization analysis for TGF-β1 messenger RNA (compare immunostaining of FIG. 7B with FIG. 7A). This illustrates that elevated expression of TGF-β1 messenger RNA in the podocytes translates into elevated protein.

RNase protection analysis was performed to determine if mRNA levels for the cytokine are also elevated in human renal cortex from Alport versus control patients. Human Alport renal cortex was removed from a 15 year old boy during transplant surgery. The specimen had a moderate level of scarification, with about 50% of the glomeruli fibrotic. The speciman was immediately removed and snap frozen in liquid nitrogen. Normal human kidney RNA was purchased from Clonetech (Palo Alto, Calif.) and was a pooled sample from a collection of normal human sources. RNA from the Alport specimen was isolated using the same procedure that was used for mouse kidneys. The RNA was examined for its integrity by fractionating 10 micrograms on an agarose gel, and staining the gel with ethidium bromide (10 micrograms per ml in water). Both the normal and Alport samples were intact based on the relative quantity of 28S and 18S ribosomal RNA bands. The RNase protection experiment was carried out according to the methods. Data in FIG. 8 illustrate a 3–4 fold elevation of TGF-β1 messenger RNA in human Alport renal cortex relative to control. This proves that the cytokine is also overexpressed in human Alport kidneys. This data substantiates the expectation that this technology will work in humans.

Example 5

Use of a Neutralizing Antibody to Block α1β1 Integrin

As an example to illustrate that a soluble agent capable of blocking the interaction of α1β1 integrin with its ligand would produce the same effects on Alport renal disease pathogenesis as the α1 gene knockout mutation, the antibody described in Fabbri et al., *Tissue Antigens,* 48:47–51, 1996 was obtained. This antibody was injected (400 ng/injection, three times weekly, intraperitonealy) into Alport mice starting at 2 weeks of age. Animals were collected at six weeks of age and the basement membranes analyzed by transmission electron microscopy. As evident in FIG. 10, the basement membranes in these treated animals were largely regular, having the normal trilaminar appearance. Endothelial cell swelling was observed due to immune response to the antibody. These results illustrate that a soluble agent that blocks the integrin α1β1 receptor will slow Alport GBM disease progression in much the same way as is observed in the double knockout mouse line.

Example 6

Effects of TGF-β1 Inhibition Alone in the Alport (129 Sv/J) Mouse Model

The experimental protocol was to inject with either FK506 (2 μg/g body weight, injected intraperitoneally, Fujisawa Pharmaceutical Co., Ltd., Osaka, Japan), or a soluble TGF-B1 receptor (25 μg/injection, intravenously through the tail vein, Biogen Inc., Cambridge, Mass.) twice weekly starting at 3 weeks of age. Kidneys were harvested at 7 weeks of age and subjected to the described analyses.

Figure 11:
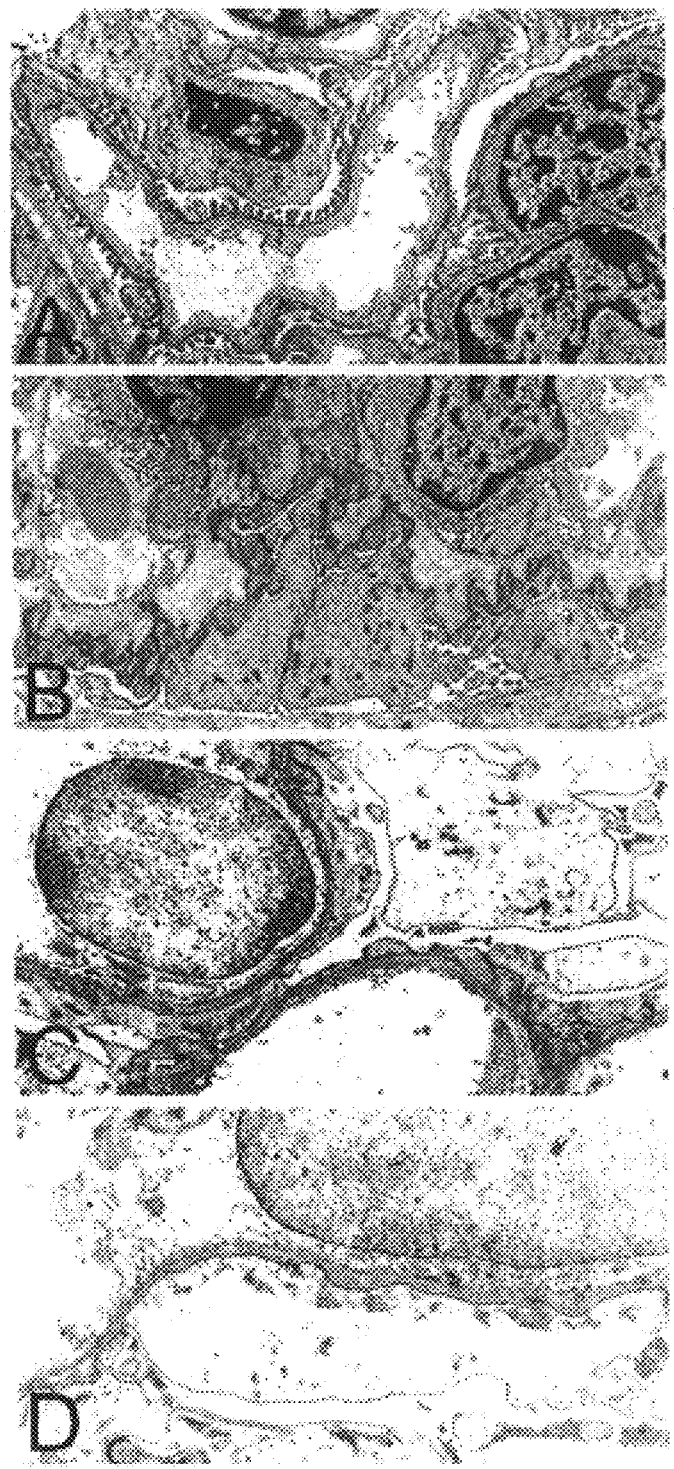
FIG. 11 illustrates the affect of TGF-β1 inhibitors on GBM ultrastructure in the 129 Sv/J Alport mouse. Animals were treated with either FK506 or the TGF-β1 soluble receptor. Renal cortex was embedded in epoxy, cut, stained with uranyl acetate and lead citrate, and analyzed by transmission electron microscopy. A=control; B=untreated Alport; C=Alport treated with FK506; D=Alport treated with the soluble TGF-β1 receptor. Magnification is 11,000×.

Transmission electron microscopic analysis of the basement membrane ultrastructure under various conditions is illustrated in FIG. 11. FIG. 11A shows a glomerular capillary loop from a normal untreated animal. Note the regular foot processes and the trilaminar basement membrane staining. FIG. 11B shows a capillary loop from a typical 7 week old 129 Sv/J Alport mouse. Note the swollen foot processes and gross focal thickening of the GBM. FIG. 11C illustrates a typical capillary loop from a 7 week old Alport animal treated with FK506. There is an obvious lack of basement membrane thickening, suggesting that the drug reduces the rate of matrix accumulation in the GBM. There is, however, a significant degree of swelling in the foot processes, with a notable lack of foot process architecture. This same observation is made in mice injected with the TGF-β1 soluble receptor (FIG. 11D). These data illustrate that TGF-β1 inhibitors can prevent irregular GBM thickening, but cannot prevent changes in foot process architecture associated with advanced Alport GBM disease.

Some of the kidney specimen was processed for scanning electron microscopy. Glomeruli were exposed by freeze fracture of renal cortex, which removes the Bowman's capsule, exposing the outer layer of podocytes as they cover the capillary loops of the glomerulus. A normal glomerulus is illustrated in FIG. 12A, where the complex architecture of the podocytes is very evident as the branching foot processes wrap around the capillary loops. In a typical 7 week old Alport mouse, the surface of the podocytes in the glomeruli are notably lacking in the fine filamentous branches, which have been obliterated by swelling (FIG. 12B). In the Alport animal treated with either FK506 or the soluble receptor for TGF-β1, the surface of the glomerulus looks much the same as that in the untreated Alport mouse (FIG. 12C). This figure clearly demonstrates that blocking TGF-β1 alone does not protect against the changes in foot process architecture associated with advanced Alport glomerular disease.

Proteinuria was measured by polyacrylamide gel electrophoresis of lyophilized urine collected at weekly time points during the course of drug treatment. As previously mentioned, the presence and abundance of albumin in the urine provides a comprehensive assessment of the integrity of the glomerular filter. FIG. 13 illustrates that while the administration of TGF-β1 inhibitors delay the onset of proteinuria, progression to high levels of albumin in the urine occurs very rapidly (1 week). These results imply that the TGF-β1 inhibitors, when used alone, do not improve the glomerular filter although they delay the onset of proteinuria. This property is likely to be directly related to the inability of these inhibitors to prevent foot process effacement of the podocytes described above and illustrated in FIGS. 11 and 12.

It should be noted that drug administration to normal littermates resulted in no discernible differences when compared to uninjected normal mice.

Example 7

Effects of TGF-β1 Inhibitors on the Double Knockout (DKO) Mice

Figure 14:
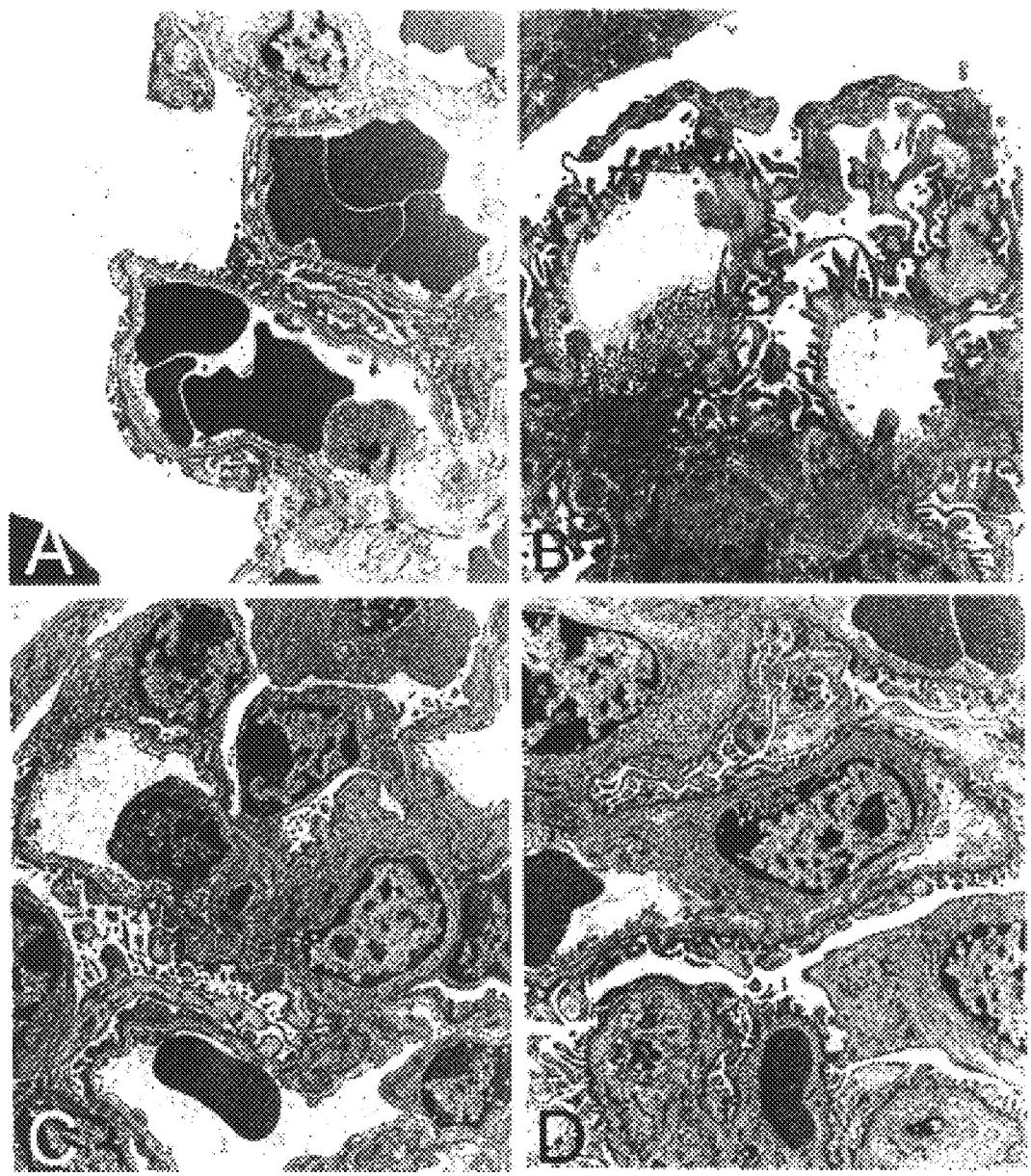
FIG. 14 illustrates the affect of TGF-β1 inhibitors on GBM ultrastructure in the double knockout mice. Animals were not treated, or treated with either FK506 or the TGF-β1 soluble receptor. Renal cortex was embedded in epoxy, cut, stained with uranyl acetate and lead citrate, and analyzed by transmission electron microscopy. A=uninjected control; B=uninjected double knockout; C=double knockout treated with FK506; D=double knockout treated with the soluble receptor for TGF-β1. Magnification is 8000x.

Mice (DKO mice are null for both the collagen α3(IV) and integrin α1 genes) were injected with TGF-β1 inhibitors FK506 (2 μg/gram body weight, twice weekly, intraperitoneal injections) or Biogen's TGF-β1 soluble receptor (25 μg per injection, twice weekly, intravenous injections) starting at four weeks of age. The kidneys were taken at 10 weeks of age and analyzed. The 10 week time point was chosen since, in the double knockouts, the disease typically progresses to the point where significant irregular thickening of the GBM is observed, and the animals are beginning to progress towards end stage renal failure. Thus, if the TGF-β1 inhibitors are to provide additional protective benefits, those benefits should be evident at this stage in GBM disease progression. Transmission electron microscopic analysis showed very clear and consistent differences between mice injected with the inhibitors and untreated double knockout mice. A typical example of these differences is illustrated in FIG. 14. FIG. 14B illustrates the typical profile of a glomerular capillary loop in the double knockout mouse at 10 weeks of age. Notable are the significant pockets of basement membrane thickening characteristic of progressing Alport glomerulonephritis. The foot processes of the podocytes possess a high degree of regular architecture with well developed slit diaphragms even in the advancing diseased state. This characteristic of double knockout mice was not shared by the Alport mice (compare foot processes with those shown in FIG. 12B).

When double knockout mice were treated with TGF-β1 inhibitors, there was a marked reduction of both focal GBM thickening and foot process effacement (FIG. 14C was treated with FK506, and FIG. 14D was treated with the soluble TGF-β1 receptor). While the GBM of most glomeruli do not have completely normal ultrastructure (note the moderate GBM irregularity apparent in FIG. 14D), completely lacking are the significant pockets of GBM thickening apparent in most glomerular capillary loops of untreated double knockout animals (as in FIG. 14B) at this developmental stage. In about 25% of the glomeruli examined in this way, TGF-β1 inhibitors restored glomerular ultrastructure to a degree where the DKO glomeruli were indistinguishable from those of normal mice (FIG. 15A shows the GBM of a ten week old normal mouse; FIG. 15B shows the GBM of a 10 week old double knockout treated with FK506). Considering that this is 2 weeks past the mean age of end stage renal failure in the unmanipulated Alport animal model, this is truly a unique and remarkable finding.

Figure 16:
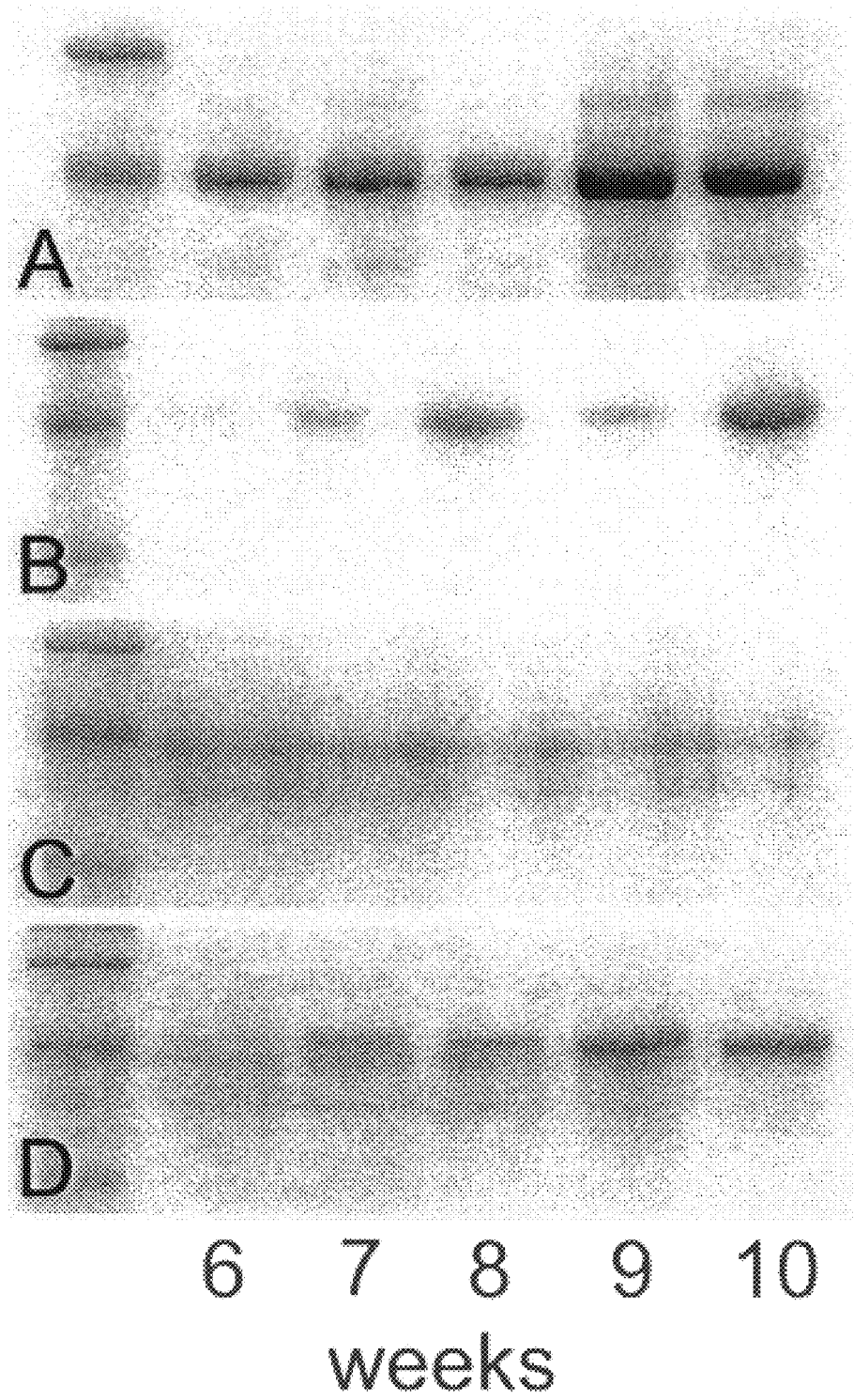
FIG. 16 demonstrates the affect of drug treatment on urinary albumin in double knockout mice. During the time-course of drug treatment, urine was collected, lyophilized, and the equivalent of 0.5 μl fractionated on a polyacrylamide gel. The gel was stained with coomassie blue and visualized. The age of the mice at the time of urine collection is indicated at the bottom of the figure (in weeks). A=uninjected double knockout; B=Double knockout injected with the soluble receptor; C=Control mouse injected with FK506; D=double knockout injected with FK506.

Proteinuria was examined in these same mice collected weekly during the course of treatment. Samples (equivalent to approximately one half of one microliter) were analyzed by electrophoresis on polyacrylamide gels. Albumin was visualized by staining with coomassie blue. The results in FIG. 16 illustrate that both treatment with either FK506 (FIG. 16D) or the soluble receptor for TGF-β1 (FIG. 16B) markedly improved the performance of the glomerular filter relative to untreated double knockout mice (FIG. 16A). FIG. 16C shows the urinary protein for a normal mouse treated with FK506. Notable is the diffuse group of bands evident at every timepoint in both the normal and the DKO (FIG. 16D) mice treated with FK506. This is always observed in mice treated with the drug, and probably related to the nephrotoxic effects reported in some patients treated with the drug following transplant (Solez et al., *Transplantation*, 66:1736–1740, 1998).

Example 8

Figure 12:
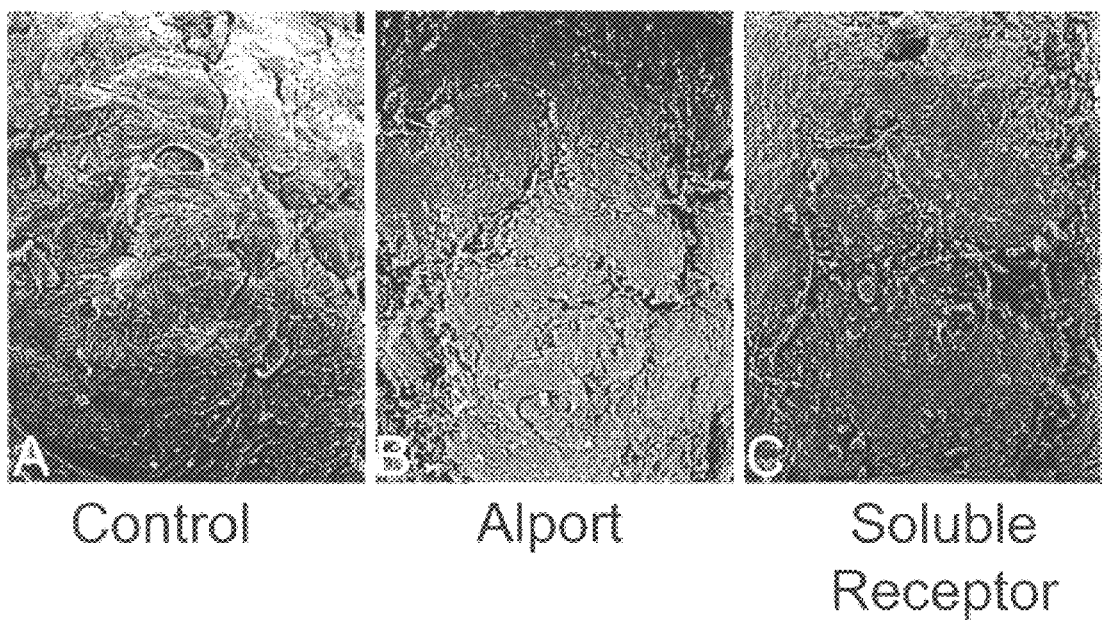
FIG. 12 is a scanning electron micrograph of glomeruli from treated versus untreated 129 Sv/J Alport mice. Renal cortex from mice used in FIG. 11 was freeze dried, cracked, stained with uranyl acetate and lead citrate, and exposed glomeruli identified and photographed using a scanning electron microscope. A=control; B=uninjected Alport; C=Alport mouse treated with the TGF-β1 soluble receptor. Magnification is 2500×.
Figure 13:
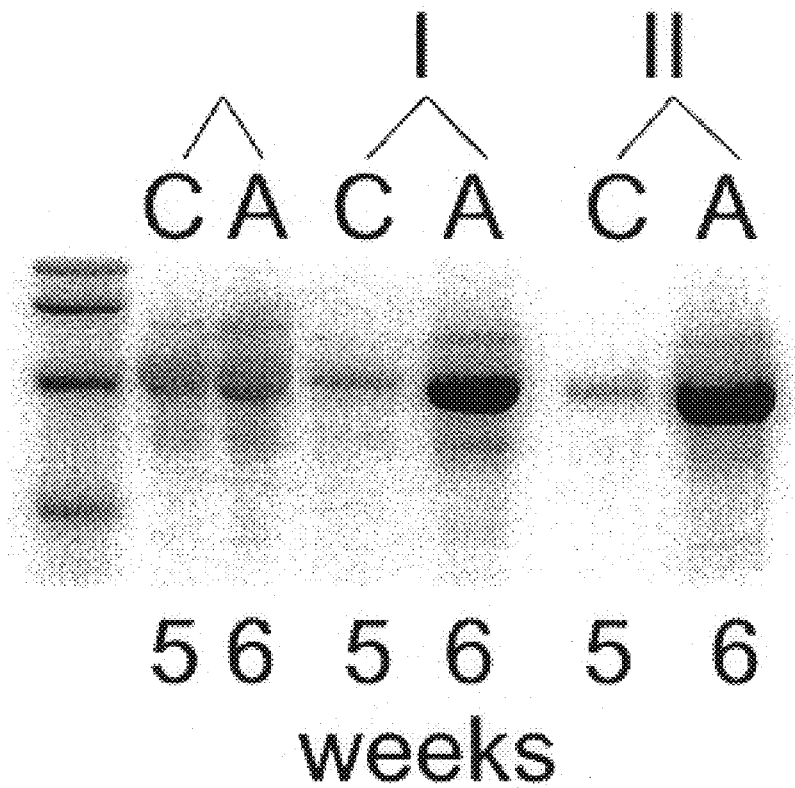
FIG. 13 demonstrates the affect of drug treatment on urinary albumin in 129 Sv/J mice Alport mice. During the timecourse of drug treatment, urine was collected, lyophilized, and the equivalent of 0.5 μl fractionated on a polyacrylamide gel. The gel was stained with coomassie blue and visualized. The first two lanes were uninjected controls, the next two (group I) were injected with FK506, and the third group (group II) were injected with the soluble TGF-β1 receptor. Numbers at the bottom represent the age of the mice at the time of urine collection in weeks. C=control; A=Alport.
Figure 17:
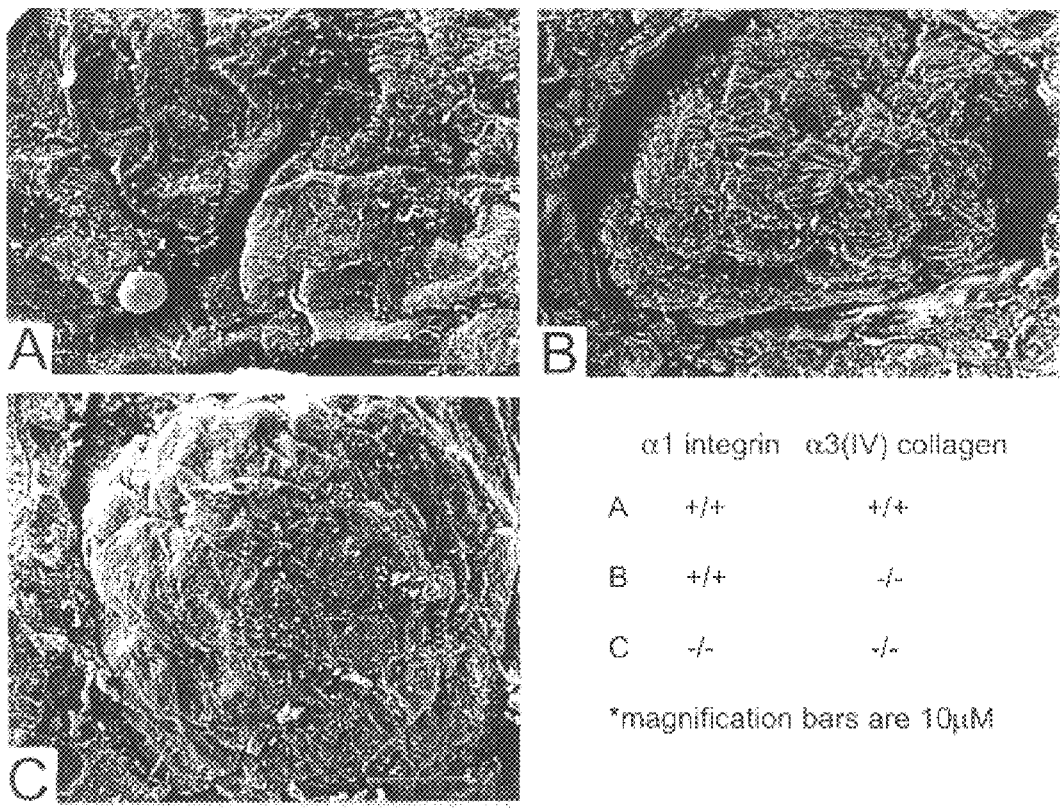
FIG. 17 is a scanning electron micrograph of glomeruli from Alport versus double knockout mice. Renal cortex from 7 week old animals was freeze dried, cracked, stained with uranyl acetate and lead citrate, and exposed glomeruli identified and photographed using a scanning electron microscope. A=control; B=Alport; C=Double knockout.

Mechanisms for the Synergistic Effects of α1 Integrin Blockers and TGF-β1 Inhibitors in Slowing Onset and Progression of Alport Glomerulonephritis Data illustrated in FIGS. 11, 12, and 14 collectively suggest that the reason α1 integrin blockers are synergistic with TGF-β1 blockers is that the α1 inhibition results in improved podocyte foot process architecture while TGF-β1 inhibition results in reduced matrix deposits in the GBM. FIG. 17 is provided to further substantiate the role of α1 integrin blockers in improving the podocyte foot process architecture. Renal cortex was prepared the same way as that illustrated in FIG. 12. FIG. 17A illustrates the surface of a glomerulus from a 7 week old normal mouse. FIG. 17B illustrates a glomerulus from a 7 week old Alport mouse. Note the loss of podocyte architecture due to effacement of the foot processes. FIG. 17C illustrates the surface of a glomerulus from a 7 week old double knockout mouse. Note the near total restoration of normal foot process architecture. These data are consistent with the cross sectional view provided by transmission electron microscopy shown in FIG. 14B, where foot processes have excellent morphology in the double knockout mouse.

Example 9

The α1 Integrin Blocking Effect

In examining a plausible mechanism for this phenomenon, the laminin chains were evaluated. Since it is known that the primary laminin found in the glomerular basement membrane is laminin 11 (Miner et al., *J. Cell Biol.*, 137:65–701, 1997), it was believed that the appearance of a new laminin in the Alport GBM might contribute to loss of podocyte attachment to the GBM. Indeed, upon examining the laminin composition of Alport GBM, the laminin α2 chain, which normally localizes exclusively to the mesangial matrix in normal mice, was found in the GBM of Alport mice. FIG. 18 illustrates a series of panels of glomeruli immunostained using a dual fluorescence labeling protocol.

In dual fluorescence analysis, fresh renal cortex was embedded in Tissue Tek aqueous embedding compound, snap frozen, and cut at 4 microns on a cryostat. Slides were postfixed in cold (−20° C.) 100% acetone for 10 minutes, and then air dried overnight. Tissue was rehydrated by three washes in PBS for 10 minutes each. The primary antibodies were diluted together in 7% non-fat dry milk (BioRad). An anti-entactin antibody (Chemicon Inc.) was used as a known marker for glomerular basement membrane at a dilution of 1:200. The laminin α2 chain-specific antibody was a gift from Dr. Peter Yurchenco (Robert Wood Johnson Medical School, Piscataway, N.J.). The specificity of this antibody for the laminin α2 chain was illustrated in Cheng et al., *J. Biol. Chem.*, 272:31525–31532, 1997. The antibody was used at a concentration of 1:10. Primary antibodies were allowed to react overnight at 4° C. in a humidified dish. Slides were washed three times for 10 minutes each in cold PBS then reacted with the secondary antibodies, which were also added together. Secondary antibodies were a Texas red-conjugated anti-rabbit for laminin α2, and an FITC-conjugated anti-rat for entactin, both used at a 1:100 dilution (Vector Laboratories, Burlingame, Calif.). Secondary reagents were allowed to react for 4 hours at 4° C. Slides were washed 3 times for ten minutes each with PBS, and a drop of Vectashield anti-fade mounting media (Vector Laboratories, Burlingame, Calif.) applied before sealing under glass coverslips. Images for each antibody were digitally overlayed using a BH-2 epifluorescence microscope interfaced with a Cytovision Ultra image analysis system (Applied Imaging, Inc.).

A glomerular basement membrane specific antigen (entactin) is in green, while the laminin α2 chain is in red. In places where the entactin and laminin α2 co-localize staining is yellow. In FIG. 18 group I, panel A represents immunostaining of a glomerulus from a 7 week old normal mouse. Here laminin α2 localizes exclusively to the mesangial matrix. Panel B illustrates staining in a 7 week old Alport littermate. Indicated by the arrows, the capillary loops stain predominantly in yellow, illustrating that in the Alport mouse, laminin α2 localizes to both the mesangial matrix and the glomerular basement membrane. Panel C shows immunostaining in the glomerulus from a 129 Sv/J Alport mouse treated with FK506 (cortex was taken from animals used in experiments described above and represented in FIGS. 11, 12, and 13). Here, again, most of the glomerular capillary loops are yellow, indicating that inhibition of TGF-β1 activity does not prevent the accumulation of laminin α2 in the GBM of Alport mice. In a 7 week old double knockout mouse, however, there is no laminin α2 immunostaining in the glomerular capillary loops (Panel D, arrows). The predominant integrin receptor on the surface of the podocytes is integrin α3β1 (Patey et al., *Cell Adhesion and Communication*, 2:159–167, 1994). This integrin is widely believed to play a key role in podocyte attachment to the GBM and maintenance of normal foot process architecture (Smoyer and Mundel, *J. Mol. Med.*, 76:172–183, 1998). As an example, it was recently shown that knocking out the integrin α3 gene resulted in complete obliteration of podocyte foot process architecture (Kreidberg et al., *Development*, 122:3537–3547, 1996). More recently, a soluble α3β1 integrin receptor was produced and shown to bind with high affinity to laminin α5 chain containing laminins (like laminin-11 which is a heterotrimer comprised of an α5, β2, and γ1 chain), but not to α2 chain containing laminins (Eble et al., *Biochemistry*, 37:10945–10955, 1998). Taken together with this information, the data presented herein support a model where, in the Alport mouse, progressive deposition of laminin α2 containing laminins in the GBM results in reduced adhesion via integrin α3β1 receptors, resulting in foot process effacement. Blocking the integrin α1 chain results in reduced or absent deposition of the laminin α2 chain in the GBM, preventing the loss of normal foot process architecture.

Figure 19:
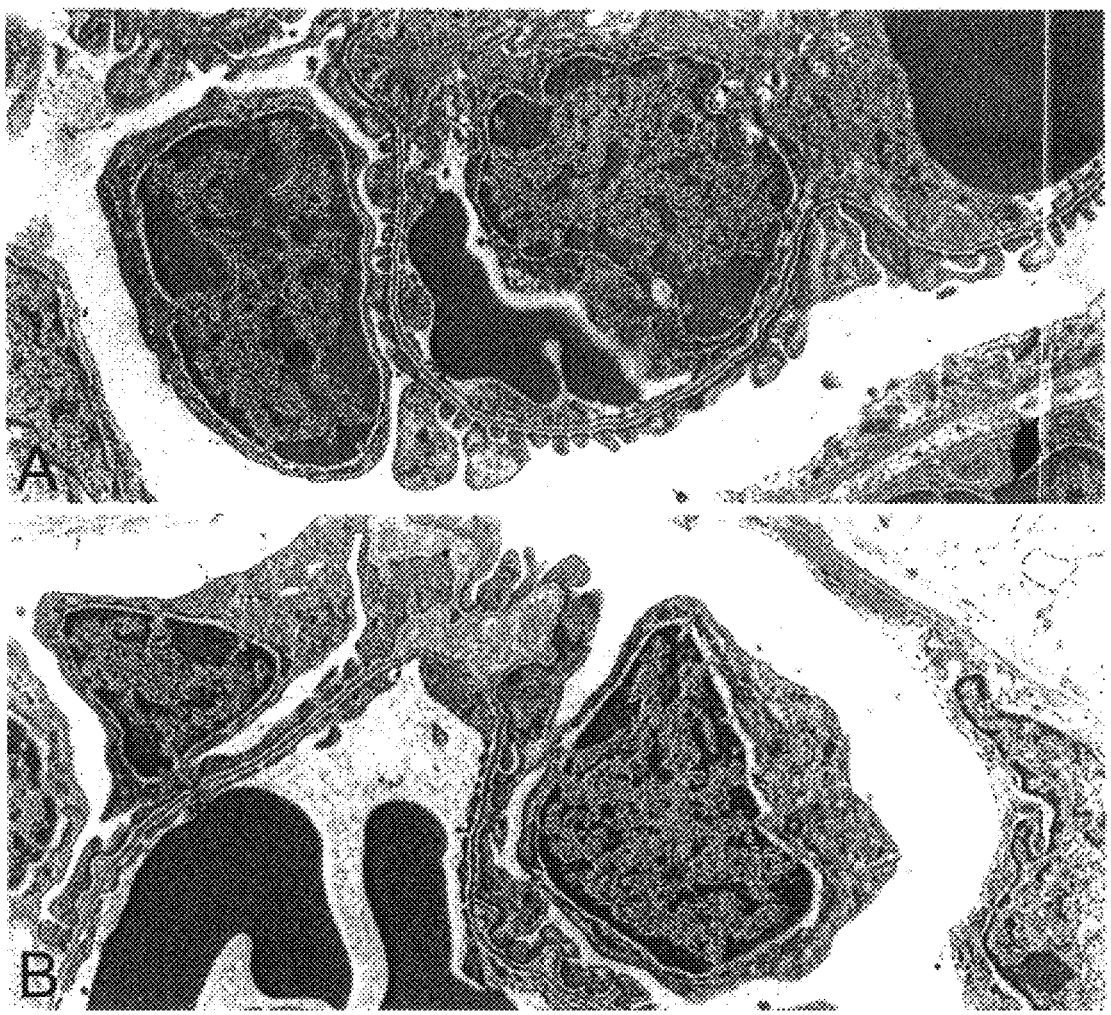
FIG. 19 is a transmission electron micrograph of the GBM of a 2 week old normal versus Alport mouse. Renal cortex was embedded in epoxy, cut, stained with uranyl acetate and lead citrate, and analyzed by transmission electron microscopy. A=control; B=Alport.

To further substantiate this point, laminin α2 chain distribution in the 2 week old Sv/J Alport mouse compared with a normal littermate was evaluated. At this very early stage in GBM disease progression, there were notable "pockets" of GBM thickening sparsely distributed on about half of the glomeruli. One such pocket of GBM thickening is shown in FIG. 19B. The GBM and podocyte foot processes are morphologically normal in unaffected regions of the glomeruli at this developmental stage, however, at the regions of focal thickening, the foot processes are swollen and effaced, much like the more generalized changes recognized later in GBM disease development. It was surmised that if laminin α2 deposition results in loss of focal adhesion contact with the podocytes, focal deposits of laminin α2 in the GBM of 2 week old Alport mice should be seen. This is indeed the case as illustrated in FIG. 18 Group II. The arrows on panel B denote focal deposition of laminin α2 in the GBM of 2 week old Alport mice. This is the earliest molecular change (other than change in type IV collagen composition, which results from the inborn genetic mutation) ever detected in the Alport mouse model, and corresponds exactly with the onset of detectable GBM damage.

Example 10

Synergistic Effect of TGF-β1 Inhibitors with α1 Integrin Blockers

Figure 20:
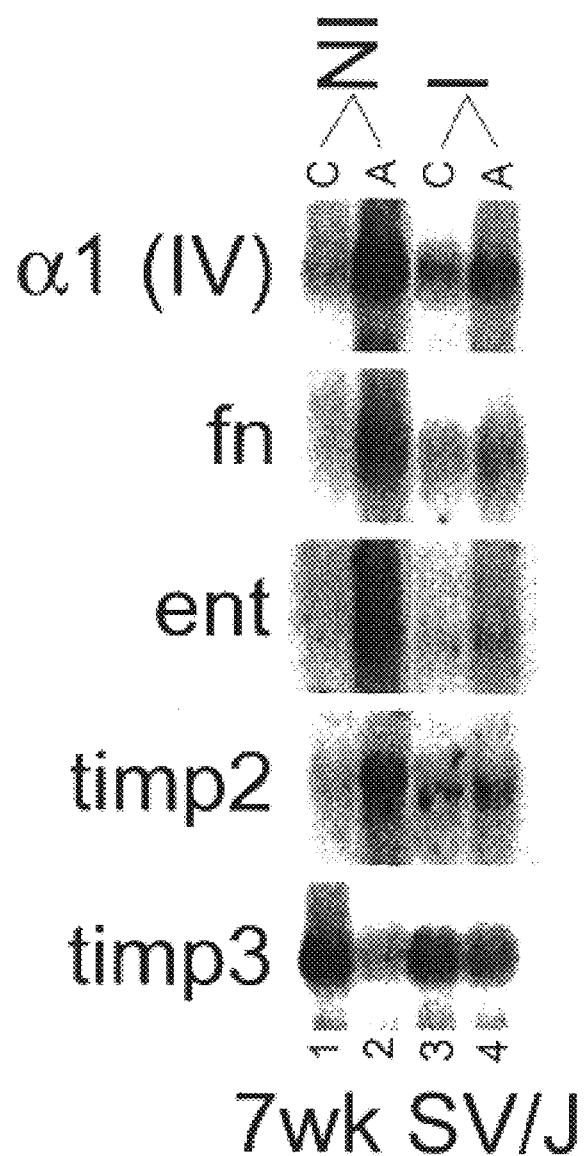
FIG. 20 demonstrates the effect of TGF-β1 inhibitors on expression, in the kidney, of RNAs encoding cell matrix molecules or metalloproteinase inhibitors in normal versus Alport mice. Total RNA was isolated from kidneys of 7 week old normal (C) or Alport (A) mice, that were either treated with FK506 (I), or not treated (NI). RNAs were fractionated on denaturing agarose gels, and analyzed by hybridization to radiolabeled probes encoding either extra-cellular matrix molecules or metalloproteinase inhibitors. Following hybridization, membranes were washed and exposed to X-ray film. Probes used are indicated to the left of the panels. α1(IV)=collagen α1(IV); fn=fibronectin; ent=entactin; Timp2=metalloproteinase inhibitor Timp-2; Timp3=metalloproteinase inhibitor Timp-3.

As illustrated in FIG. 3, the matrix that accumulates in the GBM and the interstitium as a function of Alport renal disease pathogenesis includes collagen α1(IV) and α2(IV) chains, fibronectin, and entactin. As illustrated in FIG. 20 (first two lanes of each gel), the messenger RNAs encoding each of these proteins is induced in the Alport kidney relative to normal controls. Injection of TGF-β1 inhibitors reduces the degree of induction substantially (FIG. 20 last two lanes of the gel). This may account for the reduction in basement membrane thickening observed in the Sv/J Alport mice treated with TGF-β1 inhibitors (illustrated in FIG. 11).

This similar set of northern blots were performed using RNA from kidneys from double knockout mice that were either not treated, or injected with TGF-β1 inhibitors. These were the same mice used to derive data presented in FIG. 14, thus the drug injection protocol is described in Example 7. It is evident from the data presented in FIG. 21 that the administration of TGF-β1 inhibitors does not significantly change the levels of mRNAs encoding matrix proteins as compared to non-injected control versus double knockout mice. There is, however, a marked effect on expression of mRNA encoding the metalloproteinase inhibitor Timp-3 will add to probes (FIG. 21, bottom row). As evidenced in lanes 1 and 2, there is a marked reduction in Timp-3 expression in the kidney of 10 week old untreated double knockout mice relative to control mice (a nine-fold difference based on phosphorimage analysis). This reduction in Timp-3 expression is not observed in the double knockout mice injected with either FK506 (lanes 3 and 4) or the TGF-β1 soluble receptor (lanes 5 and 6). This same effect on Timp-3 expression was observed in Sv/J mice (FIG. 20, bottom row), illustrating that the ability to inhibit the suppression of Timp-3 mRNA in Alport mice is a result of TGF-β1 inhibition inhibitors, rather than a result of dual inhibition of α1 integrin and TGF-β1.

Figure 15:
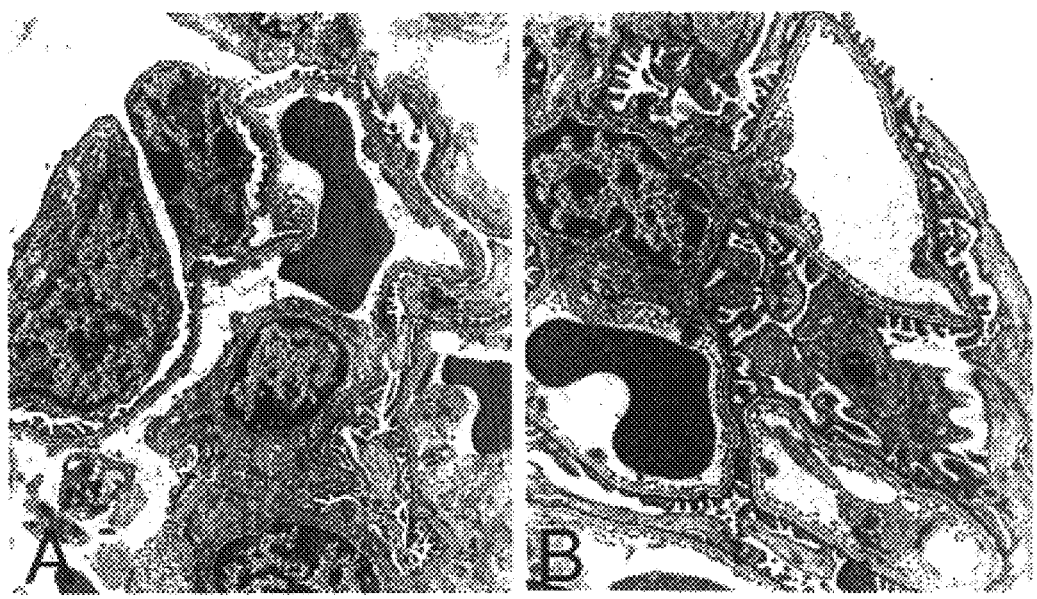
FIG. 15 illustrates an example of normal glomerular architecture in a 10 week old double knockout mouse treated with TGF-β1 inhibitors. Approximately 25% of glomeruli in mice treated with either TGF-β1 inhibitor were morphologically indistinguishable form that in control animals. Animals were not treated, or treated with FK506. Renal cortex was embedded in epoxy, cut, stained with uranyl acetate and lead citrate, and analyzed by transmission electron microscopy. A=uninjected control; B=double knockout treated with FK506.

The functional importance of this observation is based on the fact that Timp-3 is a modulator of matrix metalloproteinases, and has been suggested to be a key player in renal basement membrane homeostasis and loss of homeostasis in disease (Esposito et al., *Kidney Int.*, 50:506–514, 1996; and Elliot et al., *J. Am. Soc. Nephrol.*, 10:62–68, 1999). A reduction in the expression of Timp-3 metalloproteinase inhibitor will result in a corresponding increase in metalloproteinase activity. Such an increase could cause basement membrane damage, resulting in the activation of TGF-β1 with concomitant accumulation of matrix. Breaking this cycle would thus result in the restoration of basement membrane homeostasis, which should be manifest by restoration of GBM morphology, which is what was observed (FIGS. 11, 14, and 15).

Example 11

Figure 22:
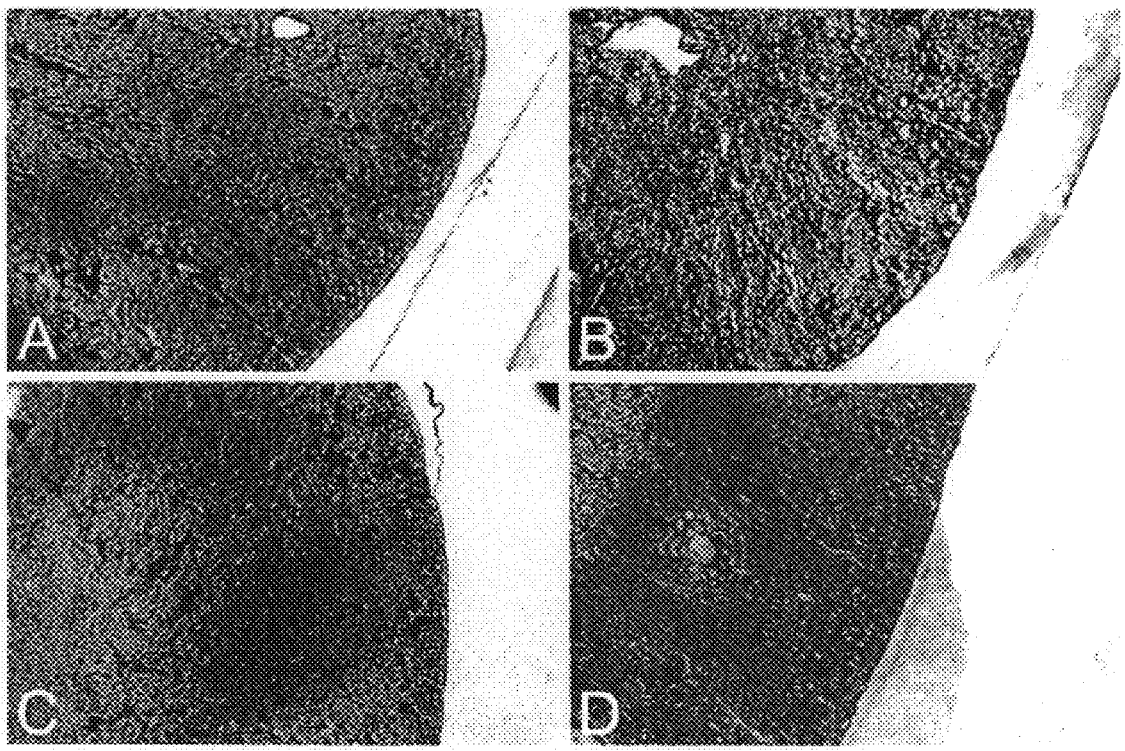
FIG. 22 illustrates the inhibition of matrix accumulation in the tubulointerstitium of double knockout mice using TGF-β1 inhibitors. Kidneys from ten week old normal or double knockout mice were embedded in plastic, and 1 μM sections were stained using the Jones silver methenamine method. A=normal kidney; B=double knockout kidney, uninjected; C=double knockout kidney treated with FK506; D=double knockout kidney treated with the TGF-β1 soluble receptor.
Figure 23:
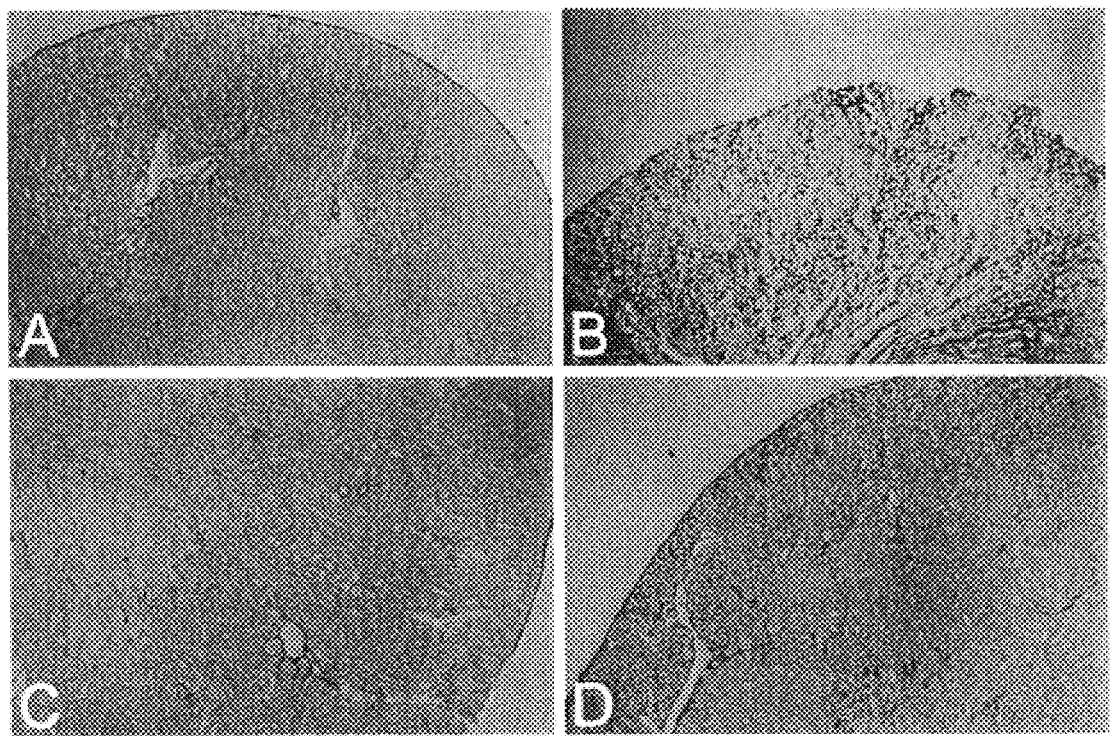
FIG. 23 illustrates the inhibition of collagen type I accumulation in the tubulointerstitium of double knockout mice using TGF-β1 inhibitors. Kidneys from ten week old normal or double knockout mice were embedded in plastic, and 1 μM sections were immunostained using antibodies specific for collagen type I. Staining was developed using the streptavidin AEC staining kit from Vector laboratories. A=normal kidney; B=double knockout kidney, uninjected; C=double knockout kidney treated with FK506; D=double knockout kidney treated with the TGF-β1 soluble receptor.
Figure 24:
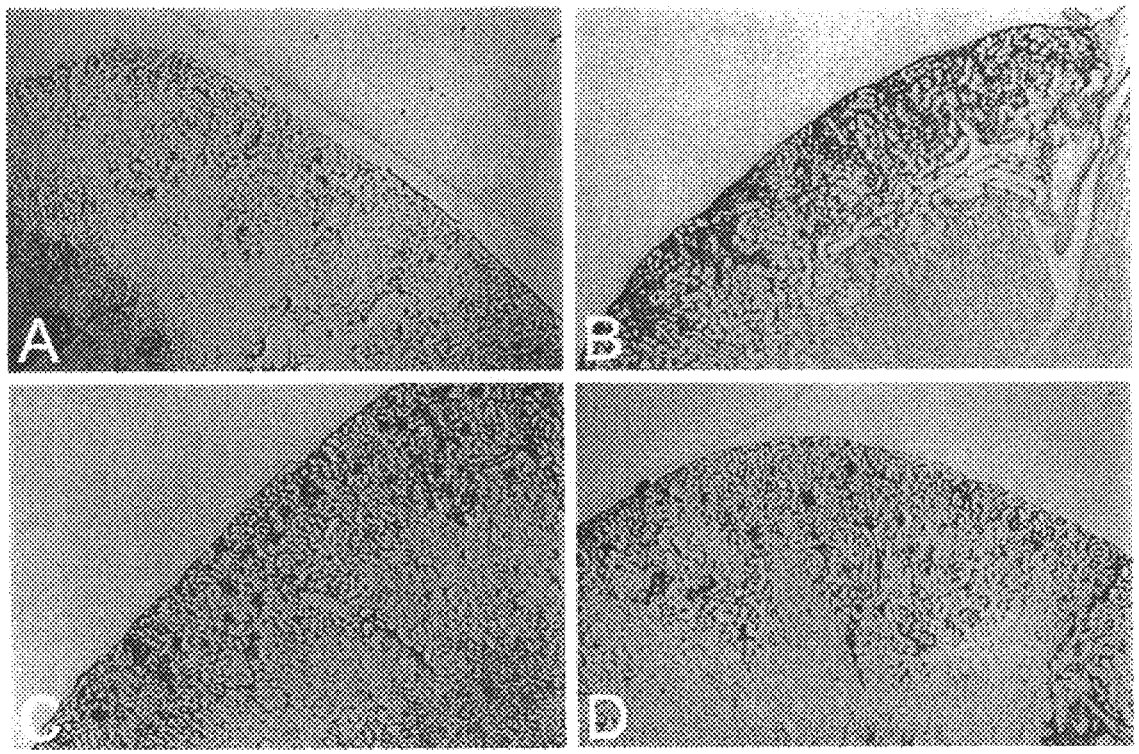
FIG. 24 illustrates the inhibition of fibronectin accumulation in the tubulointerstitium of double knockout mice using TGF-β1 inhibitors. Kidneys from ten week old normal or double knockout mice were embedded in plastic, and 1 μM sections were immunostained using antibodies specific for fibronectin. Staining was developed using the streptavidin AEC staining kit from Vector laboratories. A=normal kidney; B=double knockout kidney, uninjected; C=double knockout kidney treated with FK506; D=double knockout kidney treated with the TGF-β1 soluble receptor.

Inhibition of Interstitial Fibrosis in Double Knockout Mice Treated with TGF-β1 Inhibitors The role of TGF-β1 in upregulation of matrix proteins and in renal fibrosis has been well established (Yang et al., *J. Am. Soc. Nephrol.*, 5:1610–1617, 1995; Border and Ruoslahti, *J. Clin. Invest.*, 90:1–7, 1992). In the double knockout mouse, renal interstitial fibrosis is delayed, but does become wide spread at about 10 weeks of age, and progresses through end stage renal failure at approximately 15 weeks of age. Animals injected with TGF-β1 inhibitors were analyzed using three markers for interstitial fibrosis and compared directly with 10 week old double knockout animals that were not treated with inhibitors. Animals were injected using the same protocol as those used to generate FIG. 14 in Example 7. For FIGS. 22, 23, and 24, panel A is a control, Panel B is an untreated double knockout, panel C is a double knockout treated with FK506, and panel D is a double knockout treated with the TGF-β soluble receptor. All of these figures represent low magnification 50× views of the renal cortex. FIG. 22 is a Jones silver methenamine stain, which is a standard histochemical stain for matrix. It is evident that matrix is accumulating in the interstitium of the renal cortex in the untreated mouse (compare panel B with Panel A). The renal cortex from animals treated with either TGF-β1 inhibitor, however, were indistinguishable from the controls, indicating little to no fibrosis. Commonly used molecular markers for renal interstitial fibrosis include collagen type I and fibronectin (Yamamoto et al., *Kidney Int.*, 45:916–927, 1994). FIG. 23 illustrates immunostaining for collagen type I. Clearly, collagen type I is accumulating in the interstitium of the renal cortex of untreated animals (compare panel B to control in panel A). FIG. 23 panels B and C illustrate a relative absence of collagen type I accumulation in kidneys from double knockout mice treated with FK506 or the soluble receptor, respectively. The same scenario holds true for fibronectin, which is abundant in the cortex of untreated double knockouts (FIG. 24B), and much like controls in the renal cortex of mice injected with the TGF-β1 inhibitors (FIG. 24 panels C and D). Collectively, these data indicate that TGF-β1 inhibitors in combination with integrin alpha 1 blockers are affective at preventing (or delaying) interstitial fibrosis in the Alport mouse model.

All references, patents, patent applications, and publications cited herein are expressly incorporated by reference into this disclosure. It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method of treating irregularities in the glomerular basement membrane in a patient suffering from a kidney disorder comprising administering to the patient an effective amount of an α1β1 integrin receptor inhibitor.

2. The method of claim 1 further comprising administering to the patient an affective amount of a TGF-β1 inhibitor.

3. The method of claim 2 wherein the α1β1 integrin receptor inhibitor and the TGF-β1 inhibitor are administered simultaneously.

4. The method of claim 2 wherein the TGF-β1 inhibitor is a calcineurin inhibitor.

5. The method of claim 4 wherein the calcineurin inhibitor is tacrolimus.

6. The method of claim 2 wherein the α1β1 integrin receptor inhibitor comprises a peptide.

7. The method of claim 6 wherein the peptide is an antibody.

8. A method of delaying the onset of and/or slowing the progression of Alport syndrome in a patient, the method comprising administering to the patient an effective amount of an α1β1 integrin receptor inhibitor.

9. The method of claim 8 wherein the α1β1 integrin receptor inhibitor comprises a peptide.

10. The method of claim 9 wherein the peptide is an antibody.

11. The method of claim 8 further comprising administering to the patient an effective amount of a TGF-β1 inhibitor.

12. The method of claim 11 wherein the TGF-β1 inhibitor is a calcineurin inhibitor.

13. The method of claim 1 wherein the irregularities in the glomerular basement membrane result in effacement of podocyte foot processes.

14. The method of claim 2 wherein the TGF-β1 inhibitor is a chimeric murine fusion protein.

15. The method of claim 8 wherein the TGF-β1 inhibitor is a chimeric murine fusion protein.

16. The method of claim 12 wherein the TGF-β1 inhibitor is a calcineurin inhibitor.

* * * * *

UNITED STATES PATENT AND TRADEMARK OFFICE
CERTIFICATE OF CORRECTION

PATENT NO. : 6,492,325 B1
DATED : December 10, 2002
INVENTOR(S) : Cosgrove

It is certified that error appears in the above-identified patent and that said Letters Patent is hereby corrected as shown below:

Column 46,
Line 62, please delete "claim 2 wherein" and insert -- claim 1 wherein --;

Column 48,
Line 8, please delete "wherein the TGF-β1 inhibitor is a calcineurin inhibitor" and insert -- wherein the calcineurin inhibitor is tacrolimus --.

Signed and Sealed this

Thirtieth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,492,325 B1
APPLICATION NO. : 09/292534
DATED : December 10, 2002
INVENTOR(S) : Cosgrove It is certified that error appears in the above-identified patent and that said Letters Patent is hereby corrected as shown below:

In column 1, under the heading "STATEMENT OF GOVERNMENT RIGHTS", delete "This invention was made with government support under a grant from the National Institutes of Health, Grant No. RO1DK55000. The U.S. Government may have certain rights in this invention." and insert --The present invention was made with government support under Grant No. R01DK55000, awarded by the National Institutes of Health. The Government has certain rights in the invention.--

Signed and Sealed this

Third Day of March, 2009

JOHN DOLL
*Acting Director of the United States Patent and Trademark Office*

SEQUENCE LISTING

<160> NUMBER OF SEQ ID NOS: 26

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 1
tctgtggacc atggcttc                                            18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 2
ttctcatgca cacttggc                                            18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 3
ggctacctcc tggtgaag                                            18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 4
ttcatgcaca cttggcag                                            18

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 5
cgggccacat tctcc                                               15

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 6
ggagtggccg ttgcatt                                             17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 7
accagtacca aggcgga                                             17

<210> SEQ ID NO 8
<211> LENGTH: 18
<212> TYPE: DNA
<213> ORGANISM: Artificial Sequence

```
<220> FEATURE:
<223> OTHER INFORMATION: Description of Artificial Sequence: primer

<400> SEQUENCE: 8
tcattgagct tgttcagg                                                     18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
tagaggttat tttgcagcag a                                                 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
ttggatatcc tcatcagctt g                                                 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
gtggtttact ggacagacat c                                                 21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 12
ccaatctgtc caataaagg                                                    19

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 13
acacactcca agcccacaaa agcaag                                            26

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 14
gagggaagac tccttgtagg tcaa                                              24
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 15
gcagagcggg cacggagc                                          18

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
tgtacctgcc atcctctcct g                                      21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 17
cccctatcta cacctacacc a                                      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 18
tgtcactgtc cgccaaataa a                                      21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 19
cagaagaaga gcctgaacca ca                                     22

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 20
gtaccacgcg caagaacc                                          18

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: primer

```
<400> SEQUENCE: 21
ggtctacact attaagcaga tgaag                                                25

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 22
aaaattggag agcatgtcgg t                                                   21

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 23
gcagaagttg gcatggtag                                                      19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 24
ggacatcaac gggttcacta                                                     20

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 25
gcagaagttg gcatggtag                                                      19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 26
ggacatcaac gggttcacta                                                     20
```